(12) United States Patent
Woodley et al.

(10) Patent No.: US 11,051,983 B2
(45) Date of Patent: Jul. 6, 2021

(54) LASER EYE SURGERY SYSTEM CALIBRATION

(71) Applicant: AMO Development, LLC, Santa Ana, CA (US)

(72) Inventors: Bruce Woodley, Palo Alto, CA (US); Javier Gonzalez, Palo Alto, CA (US)

(73) Assignee: AMO Development, LLC, Santa Ana, CA (US)

( * ) Notice: Subject to any disclaimer, the term of this patent is extended or adjusted under 35 U.S.C. 154(b) by 0 days.

(21) Appl. No.: 16/377,760

(22) Filed: Apr. 8, 2019

(65) Prior Publication Data

US 2019/0231590 A1 Aug. 1, 2019

Related U.S. Application Data

(63) Continuation of application No. 15/924,121, filed on Mar. 16, 2018, now Pat. No. 10,251,784, which is a continuation of application No. 14/509,850, filed on Oct. 8, 2014, now Pat. No. 9,918,873.

(60) Provisional application No. 61/888,065, filed on Oct. 8, 2013.

(51) Int. Cl.
*A61F 9/008* (2006.01)
*A61B 3/10* (2006.01)
*G01B 9/02* (2006.01)

(52) U.S. Cl.
CPC .............. *A61F 9/008* (2013.01); *A61B 3/102* (2013.01); *A61F 9/0084* (2013.01); *A61F 9/00804* (2013.01); *A61F 9/00827* (2013.01); *G01B 9/02091* (2013.01); *A61F 2009/00851* (2013.01); *A61F 2009/00855* (2013.01); *A61F 2009/00882* (2013.01)

(58) Field of Classification Search
CPC ....................................................... A61F 9/008
See application file for complete search history.

(56) References Cited

U.S. PATENT DOCUMENTS

| | | | |
|---|---|---|---|
| 5,019,472 A | 5/1991 | Benack et al. | |
| 5,262,646 A | 11/1993 | Booker et al. | |
| 5,454,761 A | 10/1995 | Takahashi et al. | |
| 5,720,894 A | 2/1998 | Neev et al. | |
| 5,957,915 A | 9/1999 | Trost | |
| 5,984,916 A | 11/1999 | Lai | |

(Continued)

OTHER PUBLICATIONS

International Search Report and Written Opinion for Application No. PCT/US20141059740, dated Dec. 16, 2014, 9 pages.

*Primary Examiner* — John R Downey
(74) *Attorney, Agent, or Firm* — Johnson & Johnson Surgical Vision, Inc.

(57) ABSTRACT

A laser system is calibrated with a tomography system capable of measuring locations of structure within an optically transmissive material such as a tissue of an eye. Alternatively or in combination, the tomography system can be used to track the location of the eye and adjust the treatment in response to one or more of the location or an orientation of the eye. In many embodiments, in situ calibration and tracking of an optically transmissive tissue structure such as an eye can be provided. The optically transmissive material may comprise one or more optically transmissive structures of the eye, or a non-ocular optically transmissive material such as a calibration gel in a container or an optically transmissive material of a machined part.

9 Claims, 30 Drawing Sheets

(56) References Cited

U.S. PATENT DOCUMENTS

| | | |
|---|---|---|
| 7,655,002 B2 | 2/2010 | Myers et al. |
| 7,717,907 B2 | 5/2010 | Ruiz et al. |
| 8,350,183 B2 | 1/2013 | Vogel et al. |
| 8,382,745 B2 | 2/2013 | Naranjo-Tackman et al. |
| 8,414,564 B2 | 4/2013 | Goldshleger et al. |
| 2005/0215986 A1 | 9/2005 | Chernyak et al. |
| 2007/0050165 A1 | 3/2007 | Gray et al. |
| 2009/0069794 A1* | 3/2009 | Kurtz .................. A61F 9/00825 606/4 |
| 2010/0324542 A1* | 12/2010 | Kurtz .................... A61F 9/008 606/6 |
| 2010/0324543 A1* | 12/2010 | Kurtz .................. A61F 9/00825 606/6 |
| 2011/0319873 A1 | 12/2011 | Raksi et al. |
| 2011/0319875 A1 | 12/2011 | Loesel et al. |
| 2014/0058367 A1* | 2/2014 | Dantus ................ A61F 9/00802 606/6 |

* cited by examiner

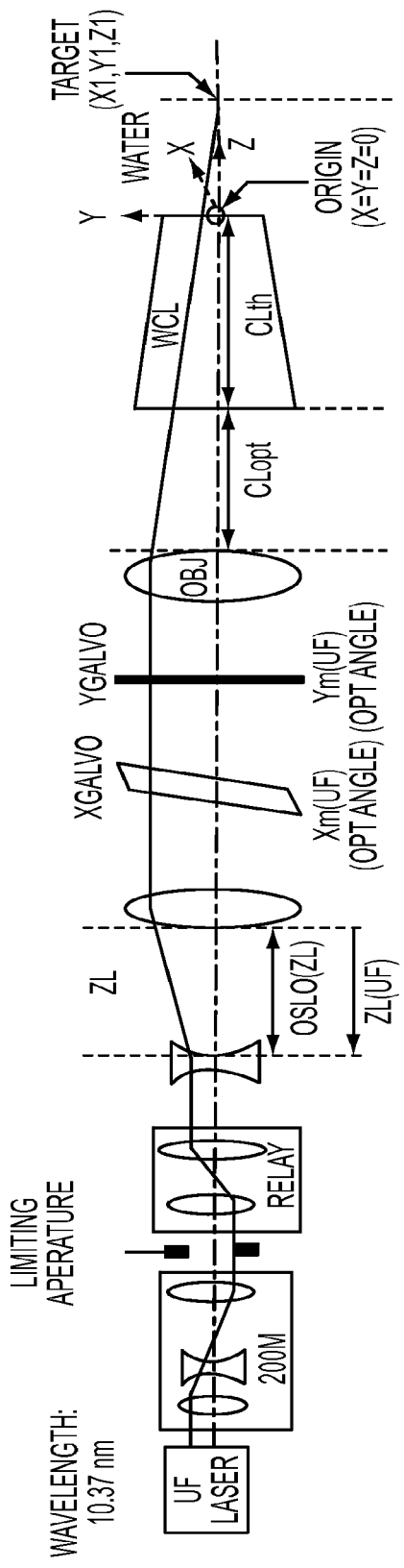
FIG. 7A1
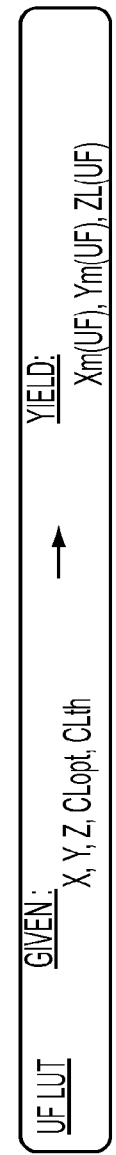
FIG. 7A2

HEADER

OF LUT,      Xm(UF) [OPTDOG], Xm(UF) [OPTDOG], ZL (UF) [mm] @1031nm GIVEN X[mm], Y[mm], Z[mm] CLopt[mm], CLth[mm]

| BASE CASES | NA | OSLO(ZL) | OPL(UF) | X | Y | Z | CLopt | CLth | XM(UF) | YM(UF) | ZL(UF) | ZED [UF] | DZ | STROHL |
|---|---|---|---|---|---|---|---|---|---|---|---|---|---|---|
| 1-ORIGIN | 0.115, | 31.9856, | 1803.1556, | 0.000, | -0.003, | 0.000, | 21.720, | 12.000, | 0.0000, | 0.0000, | 4.3104, | 0.0002, | 0.000, | 0.827 |
| 2-ORIGIN | 0.125, | 29.3254, | 1808.7800, | 0.000, | -0.002, | 6.000, | 21.720, | 12.000, | 0.0000, | 0.0000, | 6.9806, | 3.3124, | 0.000, | 0.971 |
| 3-LIMBOS X | 0.138, | 27.1908, | 1813.6048, | 6.000, | -0.000, | 8.000, | 21.720, | 12.000, | 6.8589, | 0.0000, | 9.1055, | 5.2248, | -0.000, | 0.619 |
| 4-LIMBOS Y | 0.138, | 27.1980, | 1813.7198, | 0.000, | 6.000, | 8.000, | 21.720, | 12.000, | 0.0000, | 5.9588, | 9.0980, | 5.2823, | 0.000, | 0.690 |

UF LUT: (AT LOW LOW RESOLUTION (3.5mm INCREMENTS XY, 3mm IN Z, 1um IN CLopt, 150mm IN CLth): 900 ENTRIES)

| Xmin | Xmax | Ymin | Ymax | Zmin | Zmax | CLoptmin | CLoptmax | CLthmin | CLthmax |
|---|---|---|---|---|---|---|---|---|---|
| -7.00, | 7.00, | -7.00, | 7.00, | 5.00, | 14.00, | 20.72, | 22.72, | 11.85, | 12.15 |

| Xinc | Yinc | Zinc | CLoptinc | CLthinc | FLAG |
|---|---|---|---|---|---|
| 3.3, | 3.5, | 3.0, | 1.0, | 0.15, | |

BODY

| STEP | OSLO(IL) | OPL(-) | X | Y | Z | CLopt | CLth | Xm(UF) | Ym(UF) | ZL(UF) | ZED(-) | Dz | STROHL | |
|---|---|---|---|---|---|---|---|---|---|---|---|---|---|---|
| 1, | 29.7342, | 1, | -7.000, | -7.000, | 5.000, | 20.72, | 11.850, | -6.7679, | -7.0116, | 6.5618, | 1, | 0.0020, | 0.01, | 1 |
| 2, | 29.8844, | 1, | -3.500, | -7.000, | 5.000, | 20.72, | 11.850, | -3.3682, | -6.9626, | 6.4116, | 1, | 0.0041, | 0.07, | 1 |
| 3, | 29.9327, | 1, | 0.000, | -7.000, | 5.000, | 20.72, | 11.850, | 0.0000, | -6.9466, | 6.3633, | 1, | 0.0011, | 0.20, | 1 |
| 4, | 29.8844, | 1, | 3.500, | -7.000, | 5.000, | 20.72, | 11.850, | 3.3682, | -6.9626, | 6.4116, | 1, | 0.0014, | 0.07, | 1 |
| 5, | 29.7337, | 1, | 7.000, | -7.000, | 5.000, | 20.72, | 11.850, | 6.7679, | -7.0116, | 6.5623, | 1, | 0.0028, | 0.01, | 1 |
| 6, | 29.8861, | 1, | -7.000, | -3.500, | 5.000, | 20.72, | 11.850, | -6.7045, | -3.4652, | 6.4089, | 1, | 0.0008, | 0.15, | 1 |
| 7, | 30.0310, | 1, | -3.500, | -3.500, | 5.000, | 20.72, | 11.850, | -3.3372, | -3.4572, | 6.2650, | 1, | 0.0003, | 0.59, | 1 |
| 8, | 30.0775, | 1, | 0.000, | -3.500, | 5.000, | 20.72, | 11.850, | 0.0000, | -3.4572, | 6.2185, | 1, | 0.0003, | 0.74, | 1 |
| 9, | 30.0310, | 1, | 3.500, | -3.500, | 5.000, | 20.72, | 11.850, | 3.3372, | -3.4652, | 6.2650, | 1, | 0.0002, | 0.59, | 1 |
| 10, | 29.8862, | 1, | 7.000, | -3.500, | 5.000, | 20.72, | 11.850, | 6.7045, | -3.4897, | 6.4098, | 1, | 0.0007, | 0.15, | 1 |
| 11, | 29.9340, | 1, | -7.000, | -0.000, | 5.000, | 20.72, | 11.850, | -6.6828, | 0.0000, | 6.3620, | 1, | 0.0001, | 0.53, | 1 |
| 12, | 30.0769, | 1, | -3.500, | -0.002, | 5.000, | 20.72, | 11.850, | -3.3266, | 0.0000, | 6.2191, | 1, | 0.0001, | 0.97, | 1 |
| 13, | 30.1229, | 1, | 0.000, | -0.002, | 5.000, | 20.72, | 11.850, | 0.0000, | 0.0000, | 6.1731, | 1, | -0.0000, | 0.95, | 1 |
| 14, | 30.0770, | 1, | 3.500, | -0.002, | 5.000, | 20.72, | 11.850, | 3.3266, | 0.0000, | 6.2190, | 1, | -0.0002, | 0.97, | 1 |
| 15, | 29.9340, | 1, | 7.000, | -0.000, | 5.000, | 20.72, | 11.850, | 6.6828, | 0.0000, | 6.3620, | 1, | 0.0005, | 0.53, | 1 |
| 16, | 29.8812, | 1, | -7.000, | 3.500, | 5.000, | 20.72, | 11.850, | -6.7014, | 3.4148, | 6.4148, | 1, | 0.0005, | 0.17, | 1 |
| 17, | 30.0259, | 1, | -3.500, | 3.500, | 5.000, | 20.72, | 11.850, | -3.3357, | 3.4652, | 6.2701, | 1, | 0.0002, | 0.64, | 1 |
| 18, | 30.0724, | 1, | 0.000, | 3.500, | 5.000, | 20.72, | 11.850, | 0.0000, | 3.4579, | 6.2236, | 1, | 0.0002, | 0.79, | 1 |
| 19, | 30.0259, | 1, | -3.500, | 3.500, | 5.000, | 20.72, | 11.850, | -3.3357, | 3.4652, | 6.2701, | 1, | 0.0001, | 0.64, | 1 |
| 20, | 29.8812, | 1, | 7.000, | 3.500, | 5.000, | 20.72, | 11.850, | -6.7014, | 3.4874, | 6.4248, | 1, | 0.0005, | 0.17, | 1 |

15 COLUMNS

FIG. 7A3

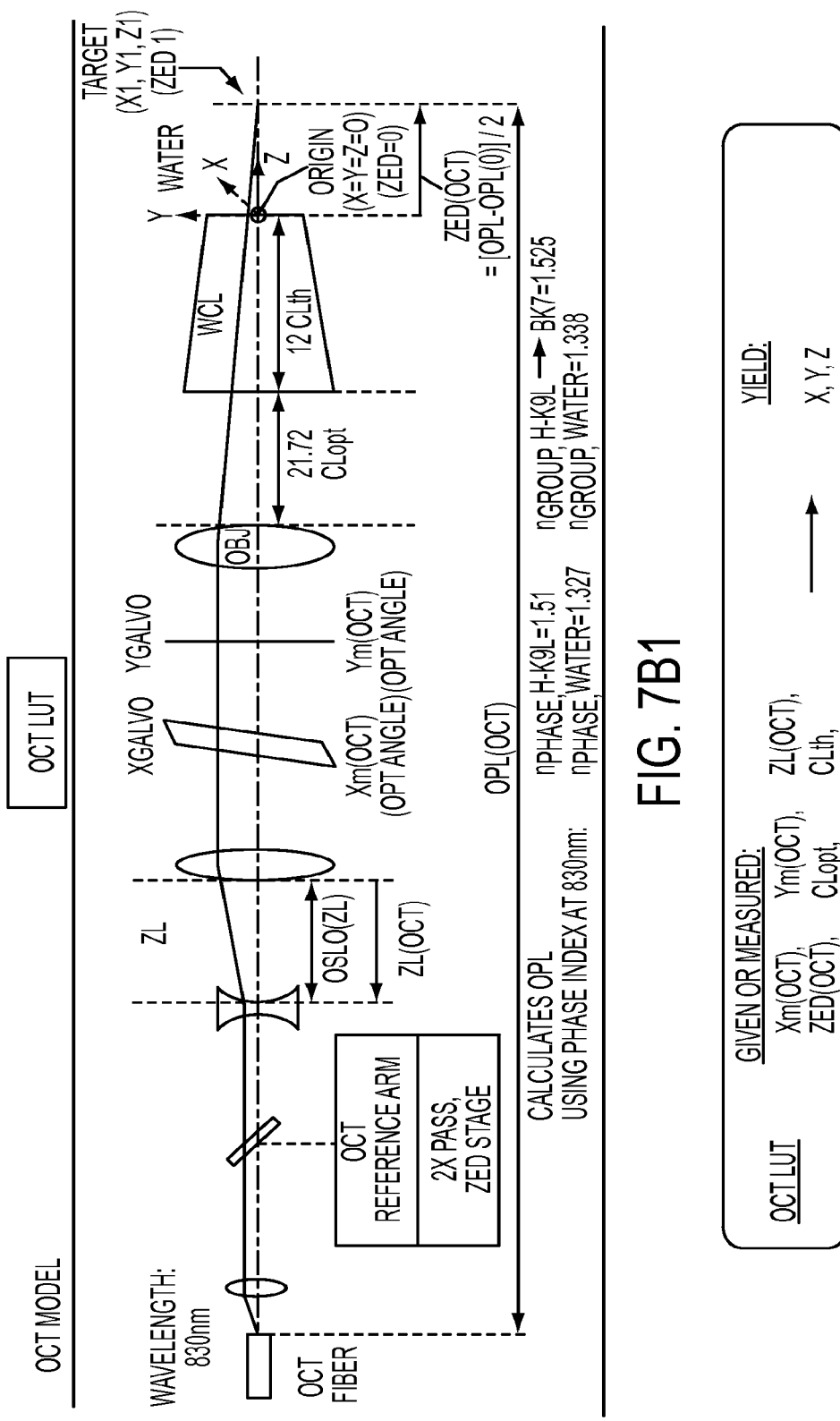
FIG. 7B1
FIG. 7B2

FIG. 7B3

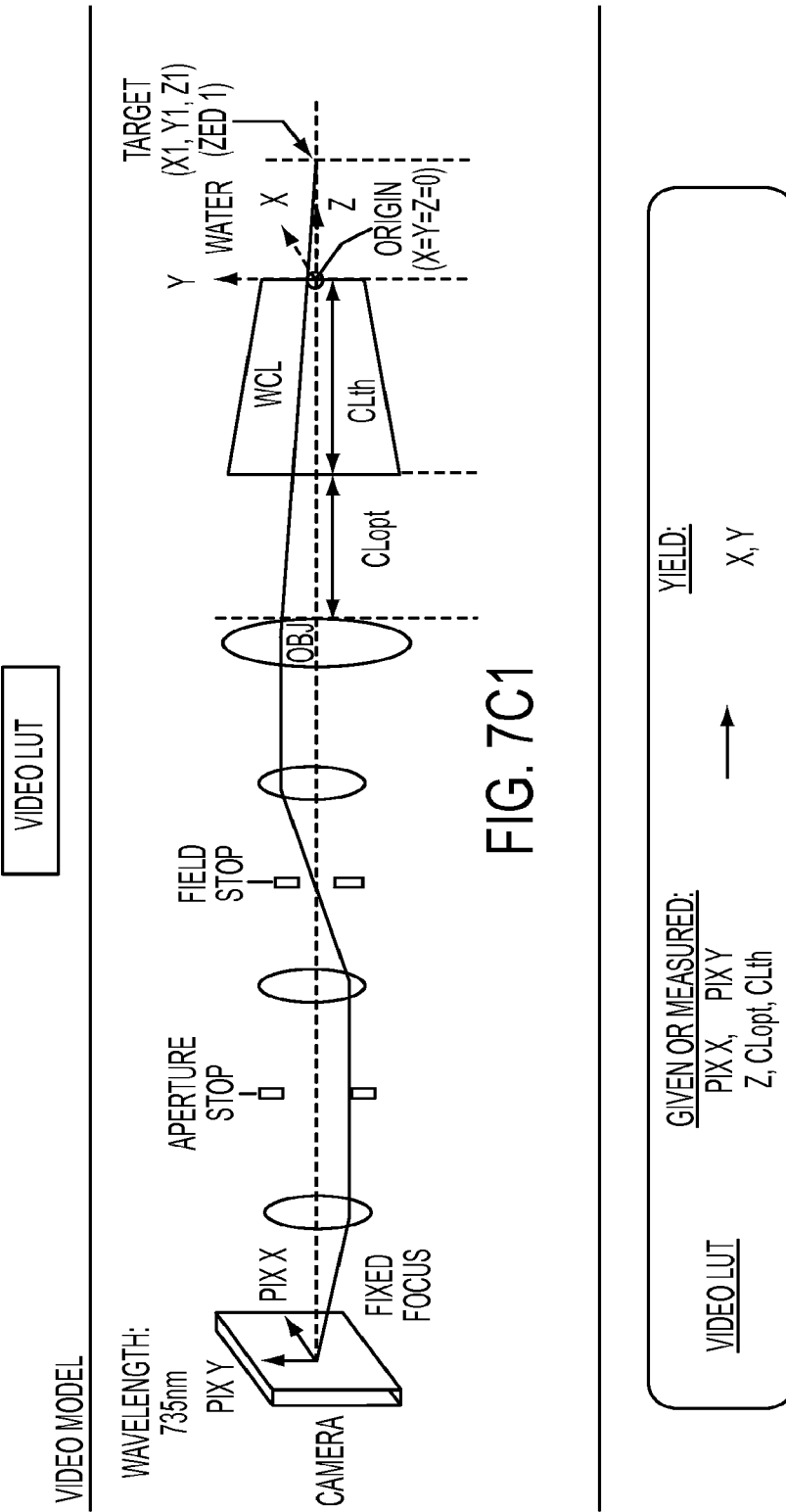
FIG. 7C1
FIG. 7C2

FIG. 7C3

HEADER

VIDEO LUT1, 735nm GIVEN Z, Y, Z, CLopt, CLth

| BASE CASE | X | Y | Z | CLopt | CLth | PIX X | PIX Y |
|---|---|---|---|---|---|---|---|
| 1, | 0.000, | 0.000, | 8.000, | 21.720, | 12.000, | 0.00, | 0.00, |
| 2, | 5.000, | 0.000, | 8.000, | 21.720, | 12.000, | 303.10, | 0.00, |
| 3, | 0.000, | 5.000, | 8.000, | 21.720, | 12.000, | 0.00, | 303.10, |

VIDEO LUT, (AT LOW RESOLUTION; 675 ENTRIES)

| Xmin | Xinc | Xmax | Ymin | Yinc | Ymax | Zmin | Zinc | Zmax | CLoptmin | CLoptinc | CLoptmax | CLthmin | CLthinc | CLthmax |
|---|---|---|---|---|---|---|---|---|---|---|---|---|---|---|
| -7.00, | 3.50, | 7.00, | -7.00, | 3.50, | 7.00, | 5.00, | 3.00, | 11.00, | 20.72, | 1.00, | 22.72, | 11.85, | 0.15, | 12.15 |

BODY

| STEP | X | Y | Z | CLopt | CLth | PIX X | PIX Y | SPOTDIA(PIX) | FLAG |
|---|---|---|---|---|---|---|---|---|---|
| 1, | -7.000, | -7.000, | 5.000, | 20.72, | 11.85, | -418.27, | -418.27, | 0.89, | 1 |
| 2, | -3.500, | -7.000, | 5.000, | 20.72, | 11.85, | -210.53, | -421.06, | 2.79, | 0 |
| 3, | 0.000, | -7.000, | 5.000, | 20.72, | 11.85, | 0.00, | -422.04, | 3.53, | 0 |
| 4, | 3.500, | -7.000, | 5.000, | 20.72, | 11.85, | 210.53, | -421.06, | 2.79, | 0 |
| 5, | 7.000, | -7.000, | 5.000, | 20.72, | 11.85, | 418.27, | -418.27, | 0.89, | 1 |
| 6, | -7.000, | -3.500, | 5.000, | 20.72, | 11.85, | -421.06, | -210.53, | 2.79, | 0 |
| 7, | -3.500, | -3.500, | 5.000, | 20.72, | 11.85, | -212.03, | -212.03, | 5.10, | 0 |
| 8, | -0.000, | -3.500, | 5.000, | 20.72, | 11.85, | 0.00, | -212.55, | 5.92, | 0 |
| 9, | 3.500, | -3.500, | 5.000, | 20.72, | 11.85, | 212.03, | -212.03, | 5.10, | 0 |
| 10, | 7.000, | -3.500, | 5.000, | 20.72, | 11.85, | 421.06, | -210.53, | 2.79, | 0 |
| 11, | -7.000, | 0.000, | 5.000, | 20.72, | 11.85, | -422.04, | 0.00, | 3.53, | 0 |
| 12, | -3.500, | 0.000, | 5.000, | 20.72, | 11.85, | -212.55, | 0.00, | 5.92, | 0 |
| 13, | 0.000, | 0.000, | 5.000, | 20.72, | 11.85, | 0.00, | 0.00, | 6.77, | 0 |
| 14, | 3.500, | 0.000, | 5.000, | 20.72, | 11.85, | 212.55, | 0.00, | 5.92, | 0 |
| 15, | 7.000, | 0.000, | 5.000, | 20.72, | 11.85, | 422.04, | 0.00, | 3.53, | 0 |
| 16, | -7.000, | 3.500, | 5.000, | 20.72, | 11.85, | -421.06, | 210.53, | 2.79, | 0 |
| 17, | -3.500, | 3.500, | 5.000, | 20.72, | 11.85, | -212.03, | 212.03, | 5.10, | 0 |
| 18, | -0.000, | 3.500, | 5.000, | 20.72, | 11.85, | 0.00, | 212.55, | 5.22, | 0 |
| 19, | 3.500, | 3.500, | 5.000, | 20.72, | 11.85, | 212.03, | 212.03, | 5.10, | 0 |
| 20, | 7.000, | 3.500, | 5.000, | 20.72, | 11.85, | -421.06, | 210.53, | 2.79, | 0 |

10 COLUMNS

LASER EYE SURGERY SYSTEM CALIBRATION

CROSS-REFERENCES TO RELATED APPLICATIONS

This application is a continuation of U.S. patent application Ser. No. 15/924,121, filed Mar. 16, 2018, allowed, which is a continuation of U.S. patent application Ser. No. 14/509,850, filed Oct. 8, 2014, now U.S. Pat. No. 9,918,873, issued Mar. 20, 2018, which claims priority to U.S. provisional application No. 61/888,065, filed on Oct. 8, 2013, the entire contents of which are incorporated herein by reference.

BACKGROUND

The present disclosure relates generally to photodisruption induced by a pulsed laser beam and the location of the photodisruption so as to treat a material, such as a tissue of an eye. Although specific reference is made to cutting tissue for surgery such as eye surgery, embodiments as described herein can be used in many ways with many materials to treat one or more of many materials, such as cutting of optically transparent materials.

Cutting of materials can be done mechanically with chisels, knives, scalpels and other tools such as surgical tools. However, prior methods and apparatus of cutting can be less than desirable and provide less than ideal results in at least some instances. For example, at least some prior methods and apparatus for cutting materials such as tissue may provide a somewhat rougher surface than would be ideal. Pulsed lasers can be used to cut one or more of many materials and have been used for laser surgery to cut tissue.

The prior methods and apparatus to incise tissue with laser beams can be less than ideal in at least some instances. For example, the laser beam may not incise tissue at the target location, and the actual location of the laser beam incision may vary from the targeted position. Although calibration can be used to improve the accuracy of the prior laser surgery systems, calibration can be time consuming and the alignment of the system components may drift over time so as to require additional calibration in at least some instances. Also, the prior methods and apparatus of calibrating laser systems can be less than ideal. For example, after calibration of the laser system, the targeted incision location can vary from the actual location of the incision.

In light of the above, it would be desirable to have improved methods and apparatus of treating materials with laser beams, such as the surgical cutting of tissue to treat cataracts and refractive errors of the eye. At least some of the above deficiencies of the prior methods and apparatus are overcome by the embodiments described herein.

SUMMARY

Embodiments as described herein provide improved treatment of materials such as tissue. In many embodiments, a laser system is calibrated with a tomography system capable of measuring locations of structure within an optically transmissive material such as a tissue of an eye. Alternatively or in combination, the tomography system can be used to track the location of the eye and adjust the treatment in response to one or more of the location or an orientation of the eye. In many embodiments, in situ calibration and tracking of an optically transmissive tissue structure such as an eye can be provided. The optically transmissive material may comprise one or more optically transmissive structures of the eye, or a non-ocular optically transmissive material such as a calibration gel in a container or an optically transmissive material of a machined part. In many embodiments, the one or more target locations comprises a plurality of target locations and the one or more marks comprises a plurality of marks, and each of the plurality of marks is identified has having a corresponding target location. The plurality of marks can be distributed so as to define a three dimensional volume in order to improve accuracy, and in many embodiments the three dimensional volume comprises a plurality of materials, each having a different index of refraction. As the tomography system may comprise one or more wavelengths different from the laser treatment system, the calibration and eye tracking can both provide improved accuracy for target tissue structures identified and measured with the tomography system. In many embodiments, the volume comprises a plurality of tissue structures in which each tissue structure comprises a different index of refraction for the tomography beam and the measurement beam. The measurement of the location of each mark and comparison with the corresponding target location for a plurality of locations of the volume can provide substantially improved accuracy, such as when the volume comprises the plurality of tissue structures having different indices of refraction.

In many embodiments, a laser system is calibrated in response to measured locations of the one or more marks. In many embodiments, a difference between the measured location and the corresponding target location and is determined for each of the plurality of marks so as to determine calibration of the laser eye surgery system. Machine parameters of the laser eye surgery system can be adjusted to as to correct errors of the plurality of marks and the corresponding target locations. The machine parameters may comprise one or more of calibration coefficients, values of look up tables, coefficients of polynomials, or mapping parameters to map from a target location of an eye coordinate reference system to a machine coordinate reference system.

Alternatively or in combination with calibration, the locations of the marks can be measured to determine movement of the eye. The location of one or more marks can be compared with prior locations of the one or more marks and the locations of the laser beam pulses adjusted in response to the measured locations. In many embodiments, each of the measured locations is compared with a reference location such as a target location or a prior location of the mark. In many embodiments, the locations of the plurality of marks are used to determine movement of the eye, rotational movement or translational movement, or both. In many embodiments, the one or more locations comprises a plurality of measured locations of the marks in order to determine the rotational and translational movement of the eye. The locations of the plurality of points can be used to determine rotation and translation of the eye in relation to the eye coordinate reference system to adjust the locations of the laser beam pulses. In many embodiments, the rotation around one or more axes of the eye and the translation along one or more axis of the eye can be used to adjust the target locations of the laser beam pulses. In many embodiments, the plurality of marks comprises three or more marks and the rotational and translational movement of the eye in relation to each of three dimensions of the eye determined, so as to correct for three translational degrees of freedom of the eye and three rotational degrees of freedom of the eye. In many embodiments, the eye comprises a plurality of tissue structures each having a different index of refraction, and the targeted locations of the eye can be adjusted in response to locations of the tissue structures having the different indices of refraction An aspect of the disclosure provides a laser system to treat an object with a laser beam. The laser system comprises a laser, a tomography system, an optical delivery system, and a processor. The laser generates the laser beam. The tomography system generates a measurement beam and measures an optically transmissive material of the object. The optical delivery system is coupled to the laser and the tomography system to deliver the laser beam and the measurement beam to the object. The processor is coupled to the laser, the tomography system, and the optical delivery system. The processor comprises a tangible medium embodying instructions to place a mark on the object with the laser beam in response to a target location and measure a location of the mark with the measurement beam.

The object to be treated with the laser beam may comprise one or more of an eye, an optically transmissive material, a gel, a liquid, a viscous material, a solid optically transmissive material, or a fluid of a patient interface above the eye. The fluid of the patient interface may comprise one or more of saline or viscoelastic fluid. The fluid may be marked with the laser beam.

The processor may comprise instructions to mark the eye at a plurality of locations corresponding to a plurality of target locations. The plurality of locations may comprise locations of one or more of a cornea, an aqueous humor, an iris, an anterior lens capsule, an anterior lens capsule, a posterior lens capsule, a cortex, or a nucleus. The processor may comprise instructions to mark the eye at the plurality of locations prior to incising the eye with a plurality of laser beam pulses to one or more of incise or treat the eye with the laser beam pulses. The plurality of marks can define a volume and laser beam pulses to incise the tissue can be delivered at a plurality of locations within the volume. The processor may further comprise instructions to identify a corresponding target location for each of the plurality of marks measured with the tomography system. The processor may comprises instructions to compare the corresponding target location with measured location for each of the plurality of marks in order to determine one or more of calibration or eye position. The volume may comprise at least a portion of a tissue structure of the eye comprising one or more of a tear film, a cornea, an aqueous humor, an iris, an anterior lens capsule, the posterior lens capsule, a lens cortex, a lens nucleus, a vitreous humor, a Berger's space or an anterior hyaloid membrane of the vitreous. The tissue structure of the eye may comprise a plurality of tissue structures. Each of the plurality of tissue structures may have a different index of refraction for the laser beam than another of the plurality of tissue structures. Each tissue structure may comprise a first index of refraction for the laser beam and a second index of refraction for a measurement beam of the tomography system. The first index of refraction may be different from the second index of refraction. The laser beam and measurement beam may comprise one or more wavelengths of light different from each other.

The processor may further comprise instructions to compare the location of the mark with the target location and calibrate the laser in response to the location of the mark and the targeted location of the mark. The processor may comprise instructions to perform in situ calibration to correct for drift of an optical delivery system to deliver the laser beam to the object. The processor may comprise instructions to perform a daily calibration to correct for drift of an optical delivery system to deliver the laser beam to the object. The processor may comprises instructions to adjust one or more machine parameters related to one or more of the laser, the optical delivery system, or the tomography system in response to a comparison of the corresponding target location with measured location for said each of the plurality of marks in order to calibrate the laser system.

The processor may comprise instructions to track the object in response to the measured location of the mark. The processor may comprise instructions to adjust positions of the laser beam pulses in response to a comparison of the corresponding target location with measured location for said each of the plurality of marks in order to track and correct for eye movement with the laser system. The location of each of the plurality of marks can be compared with a prior location of said each of the plurality of marks in order to determine movement of the eye. The plurality of marks may comprise three or more marks. The movement of the eye may comprise rotation of the eye around one or more dimensions of a coordinate reference system of the eye. The treatment can be adjusted in response to translation along the one or more dimensions. The movement of the eye can comprise translation of the eye along one or more dimensions of the coordinate reference system of the eye. The treatment can be adjusted in response to translation along the one or more dimensions. The one or more dimensions may comprise three dimensions. The treatment can be adjusted in response to rotation around the three dimensions and translation along the three dimensions. The optically transmissive material may comprise a plurality of optically transmissive structures having a plurality of indices of refraction. Positions of laser beam pulses to treat one or more of the optically transmissive structures can be adjusted in response to locations of the optically transmissive structures having the plurality of indices of refraction. The processor can comprise instructions to mark the material in each of the optically transmissive structures to define a volume comprising the plurality of optically transmissive structures having the plurality of indices of refraction. The processor can comprises instructions to mark the material in a first of the optically transmissive structures and to adjust positions of the laser beam pulses for treatment in a second of the optically transmissive structures without placing marks for tracking in the second of the optically transmissive structures. The second of the plurality of optically transmissive structures can comprise an index of refraction different than the index of refraction of the first of the optically transmissive structures.

The processor can comprise instructions to mark the material with one or more bubbles. The processor can comprise instructions to correct for optical aberrations in response to locations of the one or more bubbles.

The tomography system can comprise one or more of an optical coherence tomography system, a spectral domain optical coherence tomography system, a time domain optical coherence tomography system, a Scheimpflug tomography system, a confocal tomography system, or a low coherence reflectometry system.

The laser system may further comprise an acoustic transducer to detect optical breakdown in response to an amount of energy of the laser beam.

Another aspect of the disclosure provides a method of treating an object with a laser beam. A mark is placed on the object in response to a target location. A location of the mark is measured with a measurement beam. The laser beam can be generated by a laser and delivered by an optical delivery system. The measurement beam can be generated by a tomography system and delivered by an optical delivery system.

The tomography system may comprise one or more of an optical coherence tomography system, a spectral domain optical coherence tomography system, a time domain optical coherence tomography system, a Scheimpflug tomography system, a confocal tomography system, or a low coherence reflectometry system.

The object to be treated may comprise one or more of an eye, an optically transmissive material, a gel, a liquid, a viscous material, a solid optically transmissive material, or a fluid of a patient interface above the eye. The fluid of the patient interface may comprise one or more of saline or viscoelastic fluid. The fluid may be marked with the laser beam.

Placing the mark on the object in response to a target location may comprise marking the eye at a plurality of locations corresponding to a plurality of target locations. The plurality of locations may comprise locations of one or more of a cornea, an aqueous humor, an iris, an anterior lens capsule, an anterior lens capsule, a posterior lens capsule, a cortex or a nucleus. The eye may further be incised with a plurality of laser beam pulses to one or more of incise or treat the eye with the laser beam pulses subsequent to placing the mark on the object. The eye may be marked at the plurality of location to define a volume. The volume may comprise at least a portion of a tissue structure of the eye comprising one or more of a tear film, a cornea, an aqueous humor, an iris, an anterior lens capsule, the posterior lens capsule, a lens cortex, a lens nucleus, a vitreous humor, a Berger's space or an anterior hyaloid membrane of the vitreous humor. Laser beam pulses to incise the tissue can be delivered at a plurality of locations within the volume. A corresponding target location for each of the plurality of marks measured with the tomography system can be identified. The corresponding target location can be compared with the measured location for each of the plurality of marks in order to determine one or more of calibration or eye position. The tissue structure of the eye may comprise a plurality of tissue structures. Each of the plurality of tissue structures may have a different index of refraction for the laser beam than another of the plurality of tissue structures. Each tissue structure may comprise a first index of refraction for the laser beam and a second index of refraction for a measurement beam of the tomography system. The first index of refraction may be different from the second index of refraction. The laser beam and measurement beam may comprise one or more wavelengths of light different from each other.

Further, the location of the mark may be compared with the target location and the laser can be calibrated in response to the location of the mark and the targeted location of the mark. In situ calibration can be performed to correct for drift of an optical delivery system to deliver the laser beam to the object. A daily calibration can be performed to correct for drift of an optical delivery system to deliver the laser beam to the object. One or more machine parameters related to one or more of the laser, the optical delivery system, or the tomography system can be adjusted in response to a comparison of the corresponding target location with measured location for said each of the plurality of marks in order to calibrate the laser system.

Further, the object can be tracked in response to the measured location of the mark. The positions of the laser beam pulses can be adjusted in response to a comparison of the corresponding target location with measured location for said each of the plurality of marks in order to track and correct for eye movement with the laser system. The location of each of the plurality of marks can be compared with a prior location of said each of the plurality of marks in order to determine movement of the eye. The plurality of marks can comprise three or more marks. The movement of the eye can comprise rotation of the eye around one or more dimensions of a coordinate reference system of the eye. The treatment can be adjusted in response to translation along the one or more dimensions. The movement of the eye may comprise translation of the eye along one or more dimensions of the coordinate reference system of the eye. The treatment can be adjusted in response to translation along the one or more dimensions. The one or more dimensions may comprise three dimensions and the treatment can be adjusted in response to rotation around the three dimensions and translation along the three dimensions.

The optically transmissive material may comprise a plurality of optically transmissive structures having a plurality of indices of refraction. The positions of laser beam pulses to treat one or more of the optically transmissive structures can be adjusted in response to locations of the optically transmissive structures having the plurality of indices of refraction. The material in each of the optically transmissive structures can be marked to define a volume comprising the plurality of optically transmissive structures having the plurality of indices of refraction. The material in a first of the optically transmissive structures can be marked and the positions of the laser beam pulses can be adjusted for treatment in a second of the optically transmissive structures without placing marks for tracking in the second of the optically transmissive structures. The second of the plurality of optically transmissive structures can comprise an index of refraction different than the index of refraction of the first of the optically transmissive structures.

The material may be marked with one or more bubbles and optical aberrations can be corrected for in response to locations of the one or more bubbles.

Optical breakdown can be detected in response to an amount of energy of the laser beam with an acoustic transducer.

Additional aspects are provided in the claims below, and incorporated herein by reference.

BRIEF DESCRIPTION OF THE DRAWINGS

FIG. 7A1 shows an optical schematic of the components corresponding to the look up table summary of FIG. 7A;

FIG. 7A2 shows input and output of the look up table as in FIGS. 7A and 7A1;

FIG. 7A3 shows structure and excerpt of a look up table as in FIGS. 7A to 7A2;

FIG. 7B1 shows an optical schematic of the components corresponding to the look up table summary of FIG. 7B;

FIG. 7B2 shows input and output of the look up table as in FIGS. 7B and 7B1

FIG. 7B3 shows structure and excerpt of the look up table as in FIGS. 7B to 7B2;

FIG. 7C 1 shows an optical schematic of the components corresponding to the look up table of FIG. 7C;

FIG. 7C2 shows the input and output of the look up table as in FIGS. 7C and 7C1

FIG. 7C3 shows structure and excerpt of the look up table as in FIGS. 7C to 7C2;

DETAILED DESCRIPTION

Figure 1:
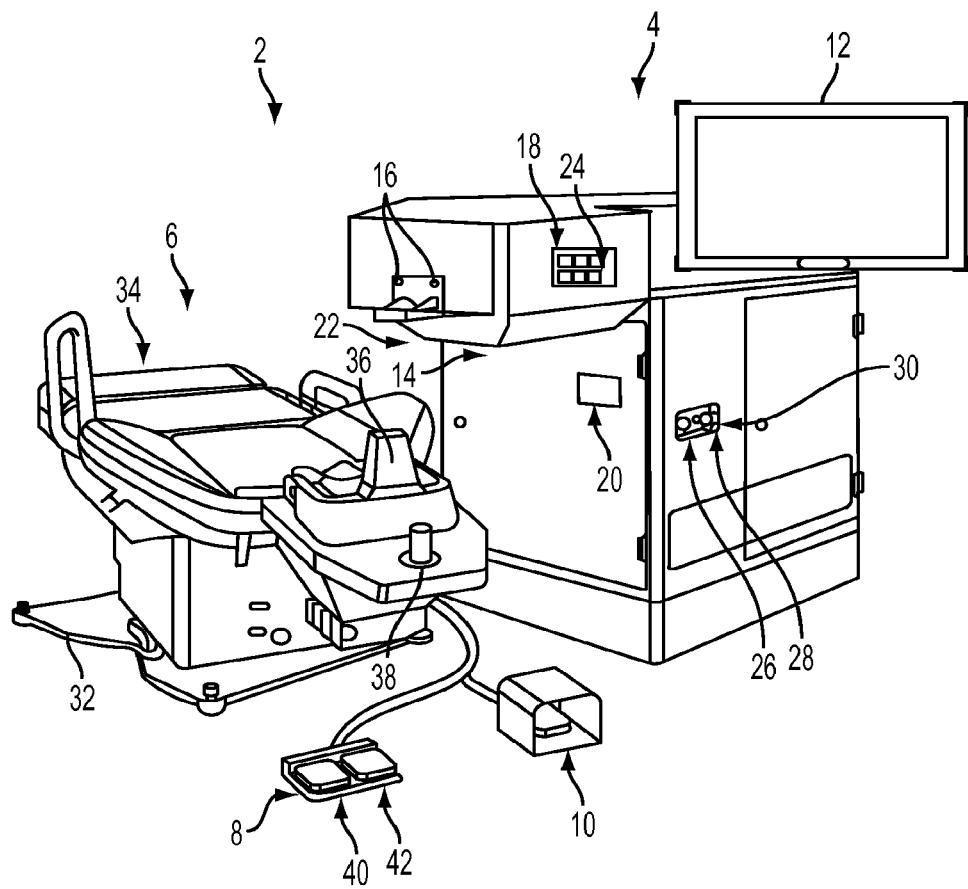
FIG. 1 shows a perspective view showing a laser eye surgery system, in accordance with many embodiments.

Methods and systems related to laser eye surgery are disclosed. In many embodiments, a laser is used to form precise incisions in the cornea, in the lens capsule, and/or in the crystalline lens nucleus. Although specific reference is made to tissue treatment for laser eye surgery, embodiments as described herein can be combined in one or more of many ways with many surgical procedures and devices, such as orthopedic surgery, robotic surgery, and microkeratomes.

The embodiments as describe herein are particularly well suit for treating tissue, such as with the surgical treatment of tissue. In many embodiments, the tissue comprises an optically transmissive tissue, such as tissue of an eye. The embodiments as described herein can be combined in many ways with one or more of many known surgical procedures such as cataract surgery, laser assisted in situ keratomileusis (hereinafter "LASIK"), laser assisted sub-epithelial keratectomy (hereinafter "LASEK"). The embodiments as described herein are also particularly well suited for retinal surgery, for example.

The embodiments as described herein are particularly well suited for calibrating laser surgery systems capable of providing a treatment within a three dimensional volume, and the target locations and marks can be defined such that as least a portion of the treatment is within the three dimensional volume defined with the plurality of target locations.

In many embodiments, the laser eye surgery system comprises a processor having a tangible medium embodying instructions to track the location of the eye in response to marks of the eye provided with pulses of the laser beam The present disclosure provides methods and apparatus for providing adjustment to compensate for variations in disposable elements and other attachments, tolerances in hardware and alignment, and patient anatomy. The methods and apparatus may comprise closed loop control combined with software calibration parameters such a calibration coefficients, or a software look up table (hereinafter "LUT") embodied in a tangible medium. The LUT may generalize a regression network, a neural network, splines, and the like. The closed loop control may comprise marking the eye at a targeted location, measuring the location of the mark with a tomography system, and correcting for the location with subsequent laser beam pulses for improved calibration or eye-tracking, and combinations thereof, for example.

The LUT may comprise a map of locations of the cutting volume in order to the control of actuators that direct the ranging (target detection) and the cutting modalities. A baseline LUT can be generated for a generalized system using optical based rules and physics, detailed modeling of components, and anchoring (one time) to a finite data set as described herein. The expected variations can be reduced into a set of finite and manageable variables that are applied to modify the tables subsequent to the original generation of the tables. For a constructed system having constructed components with manufacturing tolerances, fine tuning and modification of the LUTs can be achieved thru simple modifications of the tables based on individual system and automated measurements. These individualized measurements of a constructed system can be applied to variations due to one or more of: tool-to-tool variation, tool to itself variation (for example align variations), output attachment variations (for example disposable contact lenses), or patient to patient (for example individual patient anatomy), and combinations thereof, for example.

In many embodiments, one or more of the following steps can be performed with the processor and methods as described herein. For example, baseline LUT generation can be performed comprising mapping and position detection in order to provide actuator commands to evaluate system output performance. A baseline transfer function can be generated for a patient coordinate reference system such as XYZ to detect actuators of the system, for example. Baseline LUT generation can be performed to map cutting to actuators. A transfer function can be generated for XYZ to cutting actuators, for example. Baseline LUTs (transfer functions) can be generated via model (ray trace), data, or a combination, for example. The baseline LUTs can be modified given variations in the system, disposable, eye, and/or application, for example. The baseline LUT modification may comprise an adjustment to the baseline LUT, for example. The baseline LUT modification may comprise a software (hereinafter "SW") adjustment to compensate for hardware (hereinafter "HW") variations, for example. The LUT modification as described herein can extend surgical volume, so as to treat the cornea, the limbus and the posterior capsule, either in lateral extent, axial extent, and resolution, for example. The LUT methods and apparatus can enable switching in tools for calibration and other optical components to accessorize—output attachments, for example. The LUT can be set up so that the system is capable of measuring location of attachments at two surfaces and then can accurately place cuts in targeted material volume based on modifying the baseline LUT using this the locations of the two surfaces, for example. The LUTS can provide more cuts ranging from lens, capsule, corneal incisions for cataract, cornea flaps, for example. The different sub-systems as described herein can have separate LUTS, which can be combined with calibration process as described herein, for example.

Alternatively, or in combination, the same sub-system can be used for both ranging and cutting, for example. The UF system can be used at a low power level to find surfaces and then used at high power for cutting, for example. The LUTs can be used such that the location mode differs from the cutting mode. For example, the cut locations can differ based on changes with power level. The cut location may not occur at focus, for example when the energy per pulse substantially exceeds the threshold amount of energy, for example.

In many embodiments, the LUTs of the methods and apparatus as described herein follow these principles. The baseline LUT can generated by ray tracing and data anchoring using specific tooling, for example. In many embodiments, each optically transmissive structure of the patient interface, for example a lens, is read by the system to determine its thickness and location. These numbers can be used to modify the LUTS to attain <100 um accuracy, for example.

In many embodiments, the LUTs of the methods and apparatus as described herein are also modified to account for alignment tilts, contact lens mounting, contact lens variations so as to achieve <100 um accuracy on cuts, for example. In many embodiments, bubbles in plastic flatness test with the calibration apparatus as described herein generates offset and tilt adjustments of baseline UF LUT.

In many embodiments, the baseline component specifications may be less than ideal for delivering an appropriate system performance, and the final performance can be refined using SW corrections and factors based on the components of the individual system which can be determined from optically-grounded data-anchored baseline LUTs further modified for enhanced performance, for example.

A feedback loop can be used to build the enhanced or modified LUTs for the individual laser system, for example. The feedback methods and apparatus as described herein can allow SW adjustments based on LUTs and other SW factors that may not be corrected with hardware alignment, for example.

The LUTs and the methods an apparatus configured to modify the look up tables so as to enhance system performance can provide an improvement within the 3D surgical volume as described herein. The methods and apparatus as described herein can provide improved surgery for more patients with a level of high performance. The methods and apparatus as described herein can provide high performance using off-the-shelf components, such as high volume low cost components, such that the surgical procedures as described herein can be available to many patients.

As used herein, the terms anterior and posterior refers to known orientations with respect to the patient. Depending on the orientation of the patient for surgery, the terms anterior and posterior may be similar to the terms upper and lower, respectively, such as when the patient is placed in a supine position on a bed. The terms distal and anterior may refer to an orientation of a structure from the perspective of the user, such that the terms proximal and distal may be similar to the terms anterior and posterior when referring to a structure placed on the eye, for example. A person of ordinary skill in the art will recognize many variations of the orientation of the methods and apparatus as described herein, and the terms anterior, posterior, proximal, distal, upper, and lower are used merely by way of example.

As used herein, the terms first and second are used to describe structures and methods without limitation as to the order of the structures and methods which can be in any order, as will be apparent to a person of ordinary skill in the art based on the teachings provided herein.

As used herein light encompasses electromagnetic radiation having one or more wavelengths in one or more of the ultraviolet, visible or infrared portions of the electromagnetic spectrum.

As used herein in situ encompasses in position and refers to measurements and treatments made with an object located in substantially the same position.

FIG. 1 shows a laser eye surgery system 2, in accordance with many embodiments, operable to form precise incisions in the cornea, in the lens capsule, and/or in the crystalline lens nucleus. The system 2 includes a main unit 4, a patient chair 6, a dual function footswitch 8, and a laser footswitch 10.

The main unit 4 includes many primary subsystems of the system 2. For example, externally visible subsystems include a touch-screen control panel 12, a patient interface assembly 14, patient interface vacuum connections 16, a docking control keypad 18, a patient interface radio frequency identification (RFID) reader 20, external connections 22 (e.g., network, video output, footswitch, USB port, door interlock, and AC power), laser emission indicator 24, emergency laser stop button 26, key switch 28, and USB data ports 30.

The patient chair 6 includes a base 32, a patient support bed 34, a headrest 36, a positioning mechanism, and a patient chair joystick control 38 disposed on the headrest 36. The positioning control mechanism is coupled between the base 32 and the patient support bed 34 and headrest 36. The patient chair 6 is configured to be adjusted and oriented in three axes (x, y, and z) using the patient chair joystick control 38. The headrest 36 and a restrain system (not shown, e.g., a restraint strap engaging the patient's forehead) stabilize the patient's head during the procedure. The headrest 36 includes an adjustable neck support to provide patient comfort and to reduce patient head movement. The headrest 36 is configured to be vertically adjustable to enable adjustment of the patient head position to provide patient comfort and to accommodate variation in patient head size.

The patient chair 6 allows for tilt articulation of the patient's legs, torso, and head using manual adjustments. The patient chair 6 accommodates a patient load position, a suction ring capture position, and a patient treat position. In the patient load position, the chair 6 is rotated out from under the main unit 4 with the patient chair back in an upright position and patient footrest in a lowered position. In the suction ring capture position, the chair is rotated out from under the main unit 4 with the patient chair back in reclined position and patient footrest in raised position. In the patient treat position, the chair is rotated under the main unit 4 with the patient chair back in reclined position and patient footrest in raised position.

The patient chair 6 is equipped with a "chair enable" feature to protect against unintended chair motion. The patient chair joystick 38 can be enabled in either of two ways. First, the patient chair joystick 38 incorporates a "chair enable" button located on the top of the joystick. Control of the position of the patient chair 6 via the joystick 38 can be enabled by continuously pressing the "chair enable" button. Alternately, the left foot switch 40 of the dual function footswitch 8 can be continuously depressed to enable positional control of the patient chair 6 via the joystick 38.

In many embodiments, the patient control joystick 38 is a proportional controller. For example, moving the joystick a small amount can be used to cause the chair to move slowly. Moving the joystick a large amount can be used to cause the chair to move faster. Holding the joystick at its maximum travel limit can be used to cause the chair to move at the maximum chair speed. The available chair speed can be reduced as the patient approaches the patient interface assembly 14.

The emergency stop button 26 can be pushed to stop emission of all laser output, release vacuum that couples the patient to the system 2, and disable the patient chair 6. The stop button 26 is located on the system front panel, next to the key switch 28.

The key switch 28 can be used to enable the system 2. When in a standby position, the key can be removed and the system is disabled. When in a ready position, the key enables power to the system 2.

The dual function footswitch 8 is a dual footswitch assembly that includes the left foot switch 40 and a right foot switch 42. The left foot switch 40 is the "chair enable" footswitch. The right footswitch 42 is a "vacuum ON" footswitch that enables vacuum to secure a liquid optics interface suction ring to the patient's eye. The laser footswitch 10 is a shrouded footswitch that activates the treatment laser when depressed while the system is enabled.

In many embodiments, the system 2 includes external communication connections. For example, the system 2 can include a network connection (e.g., an RJ45 network connection) for connecting the system 2 to a network. The network connection can be used to enable network printing of treatment reports, remote access to view system performance logs, and remote access to perform system diagnostics. The system 2 can include a video output port (e.g., HDMI) that can be used to output video of treatments performed by the system 2. The output video can be displayed on an external monitor for, for example, viewing by family members and/or training. The output video can also be recorded for, for example, archival purposes. The system 2 can include one or more data output ports (e.g., USB) to, for example, enable export of treatment reports to a data storage device. The treatments reports stored on the data storage device can then be accessed at a later time for any suitable purpose such as, for example, printing from an external computer in the case where the user without access to network based printing.

Figure 2:
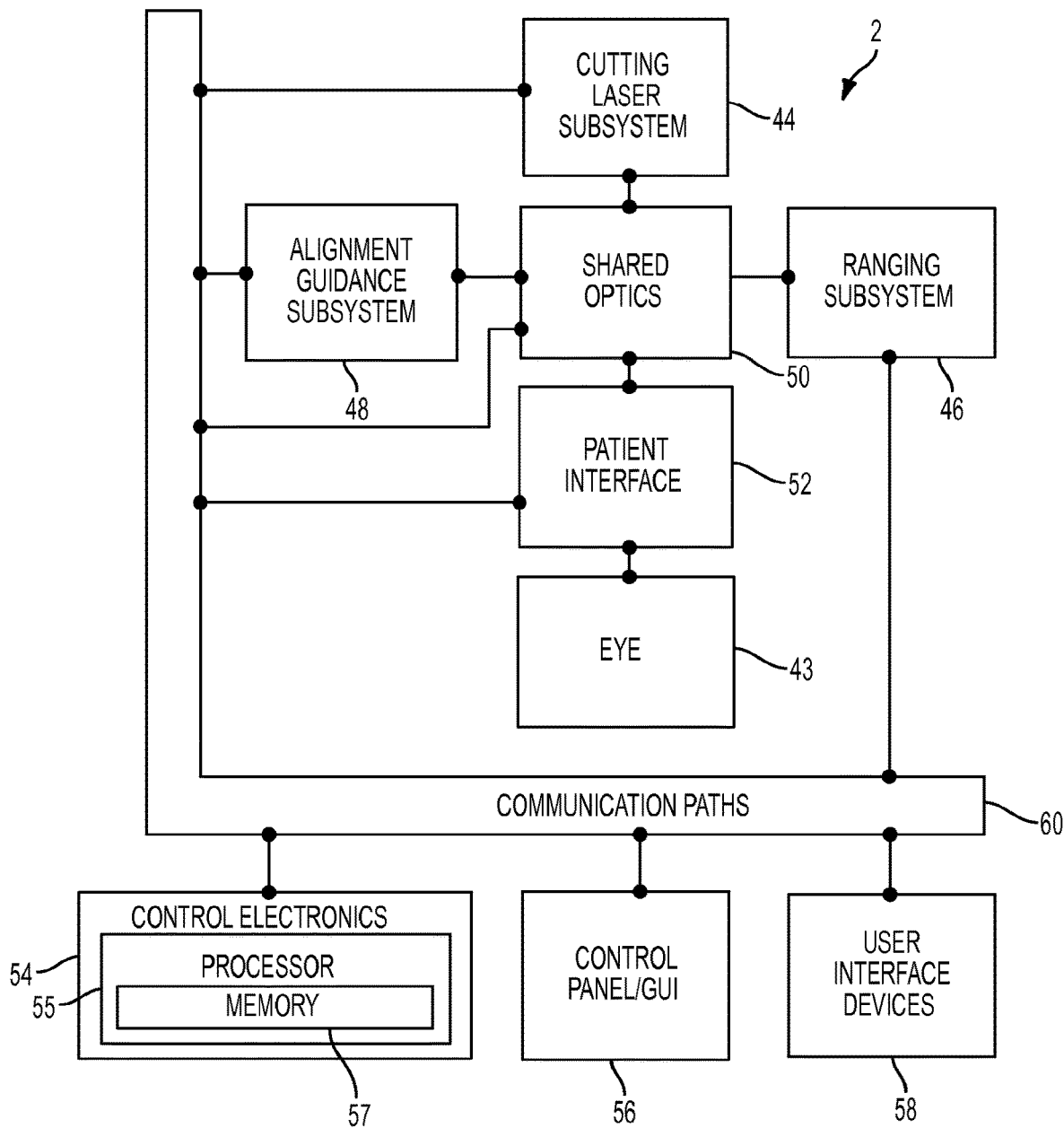
FIG. 2 shows a simplified block diagram showing a top level view of the configuration of a laser eye surgery system, in accordance with many embodiments.

FIG. 2 shows a simplified block diagram of the system 2 coupled with a patient eye 43. The patient eye 43 comprises a cornea 43C, a lens 43L and an iris 43I. The iris 43I defines a pupil of the eye 43 that may be used for alignment of eye 43 with system 2. The system 2 includes a cutting laser subsystem 44, a ranging subsystem 46, an alignment guidance system 48, shared optics 50, a patient interface 52, control electronics 54, a control panel/GUI 56, user interface devices 58, and communication paths 60. The control electronics 54 is operatively coupled via the communication paths 60 with the cutting laser subsystem 44, the ranging subsystem 46, the alignment guidance subsystem 48, the shared optics 50, the patient interface 52, the control panel/GUI 56, and the user interface devices 58.

In many embodiments, the cutting laser subsystem 44 incorporates femtosecond (FS) laser technology. By using femtosecond laser technology, a short duration (e.g., approximately $10^{-13}$ seconds in duration) laser pulse (with energy level in the micro joule range) can be delivered to a tightly focused point to disrupt tissue, thereby substantially lowering the energy level required as compared to the level required for ultrasound fragmentation of the lens nucleus and as compared to laser pulses having longer durations.

The cutting laser subsystem 44 can produce laser pulses having a wavelength suitable to the configuration of the system 2. As a non-limiting example, the system 2 can be configured to use a cutting laser subsystem 44 that produces laser pulses having a wavelength from 1020 nm to 1050 nm. For example, the cutting laser subsystem 44 can have a diode-pumped solid-state configuration with a 1030 (+/−5) nm center wavelength.

The cutting laser subsystem 44 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly to adapt the beam containing the laser pulses to the characteristics of the system 2 and a fixed optical relay to transfer the laser pulses over a distance while accommodating laser pulse beam positional and/or directional variability, thereby providing increased tolerance for component variation.

The ranging subsystem 46 is configured to measure the spatial disposition of eye structures in three dimensions. The measured eye structures can include the anterior and posterior surfaces of the cornea, the anterior and posterior portions of the lens capsule, the iris, and the limbus. In many embodiments, the ranging subsystem 46 utilizes optical coherence tomography (OCT) imaging. As a non-limiting example, the system 2 can be configured to use an OCT imaging system employing wavelengths from 780 nm to 970 nm. For example, the ranging subsystem 46 can include an OCT imaging system that employs a broad spectrum of wavelengths from 810 nm to 850 nm. Such an OCT imaging system can employ a reference path length that is adjustable to adjust the effective depth in the eye of the OCT measurement, thereby allowing the measurement of system components including features of the patient interface that lie anterior to the cornea of the eye and structures of the eye that range in depth from the anterior surface of the cornea to the posterior portion of the lens capsule and beyond.

The alignment guidance subsystem 48 can include a laser diode or gas laser that produces a laser beam used to align optical components of the system 2. The alignment guidance subsystem 48 can include LEDs or lasers that produce a fixation light to assist in aligning and stabilizing the patient's eye during docking and treatment. The alignment guidance subsystem 48 can include a laser or LED light source and a detector to monitor the alignment and stability of the actuators used to position the beam in X, Y, and Z. The alignment guidance subsystem 48 can include a video system that can be used to provide imaging of the patient's eye to facilitate docking of the patient's eye 43 to the patient interface 52. The imaging system provided by the video system can also be used to direct via the GUI the location of cuts. The imaging provided by the video system can additionally be used during the laser eye surgery procedure to monitor the progress of the procedure, to track movements of the patient's eye 43 during the procedure, and to measure the location and size of structures of the eye such as the pupil and/or limbus.

The shared optics 50 provides a common propagation path that is disposed between the patient interface 52 and each of the cutting laser subsystem 44, the ranging subsystem 46, and the alignment guidance subsystem 48. In many embodiments, the shared optics 50 includes beam combiners to receive the emission from the respective subsystem (e.g., the cutting laser subsystem 44, and the alignment guidance subsystem 48) and redirect the emission along the common propagation path to the patient interface. In many embodiments, the shared optics 50 includes an objective lens assembly that focuses each laser pulse into a focal point. In many embodiments, the shared optics 50 includes scanning mechanisms operable to scan the respective emission in three dimensions. For example, the shared optics can include an XY-scan mechanism(s) and a Z-scan mechanism. The XY-scan mechanism(s) can be used to scan the respective emission in two dimensions transverse to the propagation direction of the respective emission. The Z-scan mechanism can be used to vary the depth of the focal point within the eye 43. In many embodiments, the scanning mechanisms are disposed between the laser diode and the objective lens such that the scanning mechanisms are used to scan the alignment laser beam produced by the laser diode. In contrast, in many embodiments, the video system is disposed between the scanning mechanisms and the objective lens such that the scanning mechanisms do not affect the image obtained by the video system.

The patient interface 52 is used to restrain the position of the patient's eye 43 relative to the system 2. In many embodiments, the patient interface 52 employs a suction ring that is vacuum attached to the patient's eye 43. The suction ring is then coupled with the patient interface 52, for example, using vacuum to secure the suction ring to the patient interface 52. In many embodiments, the patient interface 52 includes an optically transmissive structure having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the patient interface lens posterior surface and the patient's cornea and forms part of a transmission path between the shared optics 50 and the patient's eye 43. The optically transmissive structure may comprise a lens 96 having one or more curved surfaces. Alternatively, the patient interface 22 may comprise an optically transmissive structure having one or more substantially flat surfaces such as a parallel plate or wedge. In many embodiments, the patient interface lens is disposable and can be replaced at any suitable interval, such as before each eye treatment.

The control electronics 54 controls the operation of and can receive input from the cutting laser subsystem 44, the ranging subsystem 46, the alignment guidance subsystem 48, the patient interface 52, the control panel/GUI 56, and the user interface devices 58 via the communication paths 60. The communication paths 60 can be implemented in any suitable configuration, including any suitable shared or dedicated communication paths between the control electronics 54 and the respective system components. The control electronics 54 can include any suitable components, such as one or more processor, one or more field-programmable gate array (FPGA), and one or more memory storage devices. In many embodiments, the control electronics 54 controls the control panel/GUI 56 to provide for pre-procedure planning according to user specified treatment parameters as well as to provide user control over the laser eye surgery procedure.

The user interface devices 58 can include any suitable user input device suitable to provide user input to the control electronics 54. For example, the user interface devices 58 can include devices such as, for example, the dual function footswitch 8, the laser footswitch 10, the docking control keypad 18, the patient interface radio frequency identification (RFID) reader 20, the emergency laser stop button 26, the key switch 28, and the patient chair joystick control 38.

Figure 3A:
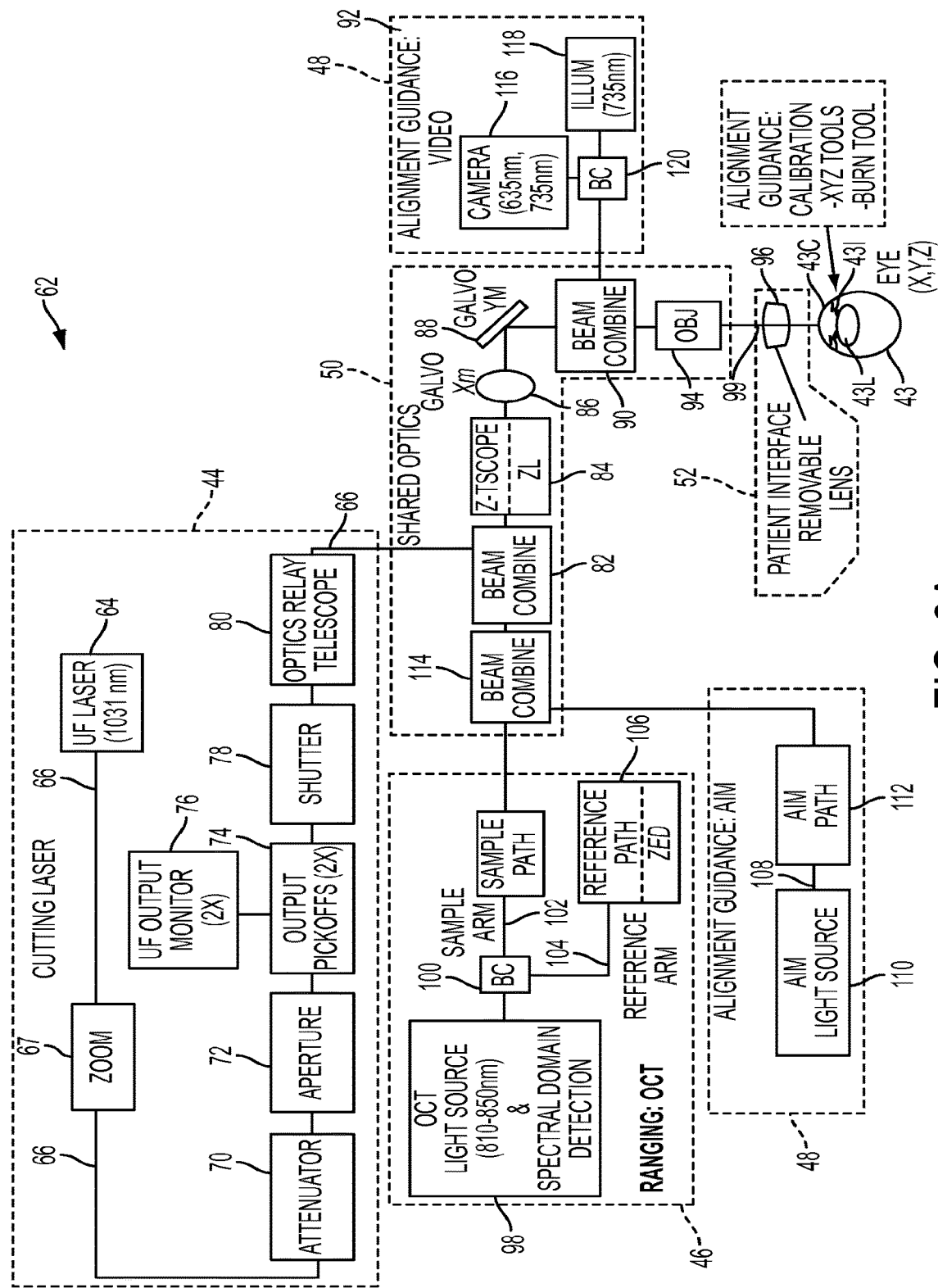
FIG. 3A shows a simplified block diagram illustrating the configuration of an optical assembly of a laser eye surgery system, in accordance with many embodiments.

FIG. 3A is a simplified block diagram illustrating an assembly 62, in accordance with many embodiments, that can be included in the system 2. The assembly 62 is a non-limiting example of suitable configurations and integration of the cutting laser subsystem 44, the ranging subsystem 46, the alignment guidance subsystem 48, the shared optics 50, and the patient interface 52. Other configurations and integration of the cutting laser subsystem 44, the ranging subsystem 46, the alignment guidance subsystem 48, the shared optics 50, and the patient interface 52 may be possible and may be apparent to a person of skill in the art.

The assembly 62 is operable to project and scan optical beams into the patient's eye 43. The cutting laser subsystem 44 includes an ultrafast (UF) laser 64 (e.g., a femtosecond laser). Using the assembly 62, optical beams can be scanned in the patient's eye 43 in three dimensions: X, Y, Z. For example, short-pulsed laser light generated by the UF laser 64 can be focused into eye tissue to produce dielectric breakdown to cause photodisruption around the focal point (the focal zone), thereby rupturing the tissue in the vicinity of the photo-induced plasma. In the assembly 62, the wavelength of the laser light can vary between 800 nm to 1200 nm and the pulse width of the laser light can vary from 10 fs to 10000 fs. The pulse repetition frequency can also vary from 10 kHz to 500 kHz. Safety limits with regard to unintended damage to non-targeted tissue bound the upper limit with regard to repetition rate and pulse energy. Threshold energy, time to complete the procedure, and stability can bound the lower limit for pulse energy and repetition rate. The peak power of the focused spot in the eye 43 and specifically within the crystalline lens and the lens capsule of the eye is sufficient to produce optical breakdown and initiate a plasma-mediated ablation process. Near-infrared wavelengths for the laser light are preferred because linear optical absorption and scattering in biological tissue is reduced for near-infrared wavelengths. As an example, the laser 64 can be a repetitively pulsed 1031 nm device that produces pulses with less than 600 fs duration at a repetition rate of 120 kHz (+/−5%) and individual pulse energy in the 1 to 20 micro joule range.

The cutting laser subsystem 44 is controlled by the control electronics 54 and the user, via the control panel/GUI 56 and the user interface devices 58, to create a laser pulse beam 66. The control panel/GUI 56 is used to set system operating parameters, process user input, display gathered information such as images of ocular structures, and display representations of incisions to be formed in the patient's eye 43.

The generated laser pulse beam 66 proceeds through a zoom assembly 68. The laser pulse beam 66 may vary from unit to unit, particularly when the UF laser 64 may be obtained from different laser manufacturers. For example, the beam diameter of the laser pulse beam 66 may vary from unit to unit (e.g., by +/−20%). The beam may also vary with regard to beam quality, beam divergence, beam spatial circularity, and astigmatism. In many embodiments, the zoom assembly 68 is adjustable such that the laser pulse beam 66 exiting the zoom assembly 68 has consistent beam diameter and divergence unit to unit.

After exiting the zoom assembly 68, the laser pulse beam 66 proceeds through an attenuator 70. The attenuator 70 is used to adjust the transmission of the laser beam and thereby the energy level of the laser pulses in the laser pulse beam 66. The attenuator 70 is controlled via the control electronics 54.

After exiting the attenuator 70, the laser pulse beam 66 proceeds through an aperture 72. The aperture 72 sets the outer useful diameter of the laser pulse beam 66. In turn the zoom determines the size of the beam at the aperture location and therefore the amount of light that is transmitted. The amount of transmitted light is bounded both high and low. The upper is bounded by the requirement to achieve the highest numerical aperture achievable in the eye. High NA promotes low threshold energies and greater safety margin for untargeted tissue. The lower is bound by the requirement for high optical throughput. Too much transmission loss in the system shortens the lifetime of the system as the laser output and system degrades over time. Additionally, consistency in the transmission through this aperture promotes stability in determining optimum settings (and sharing of) for each procedure. Typically to achieve optimal performance the transmission through this aperture as set to be between 88% to 92%.

After exiting the aperture 72, the laser pulse beam 66 proceeds through two output pickoffs 74. Each output pickoff 74 can include a partially reflecting mirror to divert a portion of each laser pulse to a respective output monitor 76. Two output pickoffs 74 (e.g., a primary and a secondary) and respective primary and secondary output monitors 76 are used to provide redundancy in case of malfunction of the primary output monitor 76.

After exiting the output pickoffs 74, the laser pulse beam 66 proceeds through a system-controlled shutter 78. The system-controlled shutter 78 ensures on/off control of the laser pulse beam 66 for procedural and safety reasons. The two output pickoffs precede the shutter allowing for monitoring of the beam power, energy, and repetition rate as a pre-requisite for opening the shutter.

After exiting the system-controlled shutter 78, the optical beam proceeds through an optics relay telescope 80. The optics relay telescope 80 propagates the laser pulse beam 66 over a distance while accommodating positional and/or directional variability of the laser pulse beam 66, thereby providing increased tolerance for component variation. As an example, the optical relay can be a keplerian afocal telescope that relays an image of the aperture position to a conjugate position near to the XY galvo mirror positions. In this way, the position of the beam at the XY galvo location is invariant to changes in the beams angle at the aperture position. Similarly the shutter does not have to precede the relay and may follow after or be included within the relay.

After exiting the optics relay telescope 80, the laser pulse beam 66 is transmitted to the shared optics 50, which propagates the laser pulse beam 66 to the patient interface 52. The laser pulse beam 66 is incident upon a beam combiner 82, which reflects the laser pulse beam 66 while transmitting optical beams from the ranging subsystem 46 and the alignment guidance subsystem: AIM 48.

Following the beam combiner 82, the laser pulse beam 66 continues through a Z-telescope 84, which is operable to scan focus position of the laser pulse beam 66 in the patient's eye 43 along the Z axis. For example, the Z-telescope 84 can include a Galilean telescope with two lens groups (each lens group includes one or more lenses). One of the lens groups moves along the Z axis about the collimation position of the Z-telescope 84. In this way, the focus position of the spot in the patient's eye 43 moves along the Z axis. In general, there is a relationship between the motion of lens group and the motion of the focus point. For example, the Z-telescope can have an approximate 2× beam expansion ratio and close to a 1:1 relationship of the movement of the lens group to the movement of the focus point. The exact relationship between the motion of the lens and the motion of the focus in the z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. The Z-telescope 84 functions as z-scan device for scanning the focus point of the laser-pulse beam 66 in the patient's eye 43. The Z-telescope 84 can be controlled automatically and dynamically by the control electronics 54 and selected to be independent or to interplay with the X and Y scan devices described next.

After passing through the Z-telescope 84, the laser pulse beam 66 is incident upon an X-scan device 86, which is operable to scan the laser pulse beam 66 in the X direction, which is dominantly transverse to the Z axis and transverse to the direction of propagation of the laser pulse beam 66.

The X-scan device 86 is controlled by the control electronics 54, and can include suitable components, such as a motor, galvanometer, or any other well-known optic moving device. The relationship of the motion of the beam as a function of the motion of the X actuator does not have to be fixed or linear. Modeling or calibrated measurement of the relationship or a combination of both can be determined and used to direct the location of the beam.

After being directed by the X-scan device 86, the laser pulse beam 66 is incident upon a Y-scan device 88, which is operable to scan the laser pulse beam 66 in the Y direction, which is dominantly transverse to the X and Z axes. The Y-scan device 88 is controlled by the control electronics 54, and can include suitable components, such as a motor, galvanometer, or any other well-known optic moving device. The relationship of the motion of the beam as a function of the motion of the Y actuator does not have to be fixed or linear. Modeling or calibrated measurement of the relationship or a combination of both can be determined and used to direct the location of the beam. Alternatively, the functionality of the X-Scan device 86 and the Y-Scan device 88 can be provided by an XY-scan device configured to scan the laser pulse beam 66 in two dimensions transverse to the Z axis and the propagation direction of the laser pulse beam 66. The X-scan and Y-scan devices 86, 88 change the resulting direction of the laser pulse beam 66, causing lateral displacements of UF focus point located in the patient's eye 43.

After being directed by the Y-scan device 88, the laser pulse beam 66 passes through a beam combiner 90. The beam combiner 90 is configured to transmit the laser pulse beam 66 while reflecting optical beams to and from a video subsystem 92 of the alignment guidance subsystem 48.

After passing through the beam combiner 90, the laser pulse beam 66 passes through an objective lens assembly 94. The objective lens assembly 94 can include one or more lenses. In many embodiments, the objective lens assembly 94 includes multiple lenses. The complexity of the objective lens assembly 94 may be driven by the scan field size, the focused spot size, the degree of telecentricity, the available working distance on both the proximal and distal sides of objective lens assembly 94, as well as the amount of aberration control.

After passing through the objective lens assembly 94, the laser pulse beam 66 passes through the patient interface 52. As described above, in many embodiments, the patient interface 52 includes a patient interface lens 96 having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the posterior surface of the patient interface lens 96 and the patient's cornea and forms part of an optical transmission path between the shared optics 50 and the patient's eye 43.

The shared optics 50 under the control of the control electronics 54 can automatically generate aiming, ranging, and treatment scan patterns. Such patterns can be comprised of a single spot of light, multiple spots of light, a continuous pattern of light, multiple continuous patterns of light, and/or any combination of these. In addition, the aiming pattern (using the aim beam 108 described below) need not be identical to the treatment pattern (using the laser pulse beam 66), but can optionally be used to designate the boundaries of the treatment pattern to provide verification that the laser pulse beam 66 will be delivered only within the desired target area for patient safety. This can be done, for example, by having the aiming pattern provide an outline of the intended treatment pattern. This way the spatial extent of the treatment pattern can be made known to the user, if not the exact locations of the individual spots themselves, and the scanning thus optimized for speed, efficiency, and/or accuracy. The aiming pattern can also be made to be perceived as blinking in order to further enhance its visibility to the user. Likewise, the ranging beam 102 need not be identical to the treatment beam or pattern. The ranging beam needs only to be sufficient enough to identify targeted surfaces. These surfaces can include the cornea and the anterior and posterior surfaces of the lens and may be considered spheres with a single radius of curvature. Also the optics shared by the alignment guidance: video subsystem does not have to be identical to those shared by the treatment beam. The positioning and character of the laser pulse beam 66 and/or the scan pattern the laser pulse beam 66 forms on the eye 43 may be further controlled by use of an input device such as a joystick, or any other appropriate user input device (e.g., control panel/GUI 56) to position the patient and/or the optical system.

The control electronics 54 can be configured to target the targeted structures in the eye 43 and ensure that the laser pulse beam 66 will be focused where appropriate and not unintentionally damage non-targeted tissue. Imaging modalities and techniques described herein, such as those mentioned above, or ultrasound may be used to determine the location and measure the thickness of the lens and lens capsule to provide greater precision to the laser focusing methods, including 2D and 3D patterning. Laser focusing may also be accomplished by using one or more methods including direct observation of an aiming beam, or other known ophthalmic or medical imaging modalities, such as those mentioned above, and/or combinations thereof. Additionally the ranging subsystem such as an OCT can be used to detect features or aspects involved with the patient interface. Features can include fiducials places on the docking structures and optical structures of the disposable lens such as the location of the anterior and posterior surfaces.

In the embodiment of FIG. 3A, the ranging subsystem 46 includes an OCT imaging device. Additionally or alternatively, imaging modalities other than OCT imaging can be used. An OCT scan of the eye can be used to measure the spatial disposition (e.g., three dimensional coordinates such as X, Y, and Z of points on boundaries) of structures of interest in the patient's eye 43. Such structure of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, and/or the limbus. The spatial disposition of the structures of interest and/or of suitable matching geometric modeling such as surfaces and curves can be generated and/or used by the control electronics 54 to program and control the subsequent laser-assisted surgical procedure. The spatial disposition of the structures of interest and/or of suitable matching geometric modeling can also be used to determine a wide variety of parameters related to the procedure such as, for example, the upper and lower axial limits of the focal planes used for cutting the lens capsule and segmentation of the lens cortex and nucleus, and the thickness of the lens capsule among others.

The ranging subsystem 46 in FIG. 3A includes an OCT light source and detection device 98. The OCT light source and detection device 98 includes a light source that generates and emits light with a suitable broad spectrum. For example, in many embodiments, the OCT light source and detection device 98 generates and emits light with a broad spectrum from 810 nm to 850 nm wavelength. The generated and emitted light is coupled to the device 98 by a single mode fiber optic connection.

The light emitted from the OCT light source and detection device 98 is passed through a beam combiner 100, which divides the light into a sample portion 102 and a reference portion 104. A significant portion of the sample portion 102 is transmitted through the shared optics 50. A relative small portion of the sample portion is reflected from the patient interface 52 and/or the patient's eye 43 and travels back through the shared optics 50, back through the beam combiner 100 and into the OCT light source and detection device 98. The reference portion 104 is transmitted along a reference path 106 having an adjustable path length. The reference path 106 is configured to receive the reference portion 104 from the beam combiner 100, propagate the reference portion 104 over an adjustable path length, and then return the reference portion 106 back to the beam combiner 100, which then directs the returned reference portion 104 back to the OCT light source and detection device 98. The OCT light source and detection device 98 then directs the returning small portion of the sample portion 102 and the returning reference portion 104 into a detection assembly, which employs a time domain detection technique, a frequency detection technique, or a single point detection technique. For example, a frequency-domain technique can be used with an OCT wavelength of 830 nm and bandwidth of 10 nm.

Once combined with the UF laser pulse beam 66 subsequent to the beam combiner 82, the OCT sample portion beam 102 follows a shared path with the UF laser pulse beam 66 through the shared optics 50 and the patient interface 52. In this way, the OCT sample portion beam 102 is generally indicative of the location of the UF laser pulse beam 66. Similar to the UF laser beam, the OCT sample portion beam 102 passes through the Z-telescope 84, is redirected by the X-scan device 86 and by the Y-scan device 88, passes through the objective lens assembly 94 and the patient interface 52, and on into the eye 43. Reflections and scatter off of structures within the eye provide return beams that retrace back through the patient interface 52, back through the shared optics 50, back through the beam combiner 100, and back into the OCT light source and detection device 98. The returning back reflections of the sample portion 102 are combined with the returning reference portion 104 and directed into the detector portion of the OCT light source and detection device 98, which generates OCT signals in response to the combined returning beams. The generated OCT signals that are in turn interpreted by the control electronics to determine the spatial disposition of the structures of interest in the patient's eye 43. The generated OCT signals can also be interpreted by the control electronics to measure the position and orientation of the patient interface 52, as well as to determine whether there is liquid disposed between the posterior surface of the patient interface lens 96 and the patient's eye 43.

The OCT light source and detection device 98 works on the principle of measuring differences in optical path length between the reference path 106 and the sample path. Therefore, different settings of the Z-telescope 84 to change the focus of the UF laser beam do not impact the length of the sample path for a axially stationary surface in the eye of patient interface volume because the optical path length does not change as a function of different settings of the Z-telescope 84. The ranging subsystem 46 has an inherent Z range that is related to light source and the detection scheme, and in the case of frequency domain detection the Z range is specifically related to the spectrometer, the wavelength, the bandwidth, and the length of the reference path 106. In the case of ranging subsystem 46 used in FIG. 3A, the Z range is approximately 4-5 mm in an aqueous environment. Extending this range to at least 20-25 mm involves the adjustment of the path length of the reference path 106 via a stage ZED within ranging subsystem 46. Passing the OCT sample portion beam 102 through the Z-telescope 84, while not impacting the sample path length, allows for optimization of the OCT signal strength. This is accomplished by focusing the OCT sample portion beam 102 onto the targeted structure. The focused beam both increases the return reflected or scattered signal that can be transmitted through the single mode fiber and increases the spatial resolution due to the reduced extent of the focused beam. The changing of the focus of the sample OCT beam can be accomplished independently of changing the path length of the reference path 106.

Because of the fundamental differences in how the sample portion 102 (e.g., 810 nm to 850 nm wavelengths) and the UF laser pulse beam 66 (e.g., 1020 nm to 1050 nm wavelengths) propagate through the shared optics 50 and the patient interface 52 due to influences such as immersion index, refraction, and aberration, both chromatic and monochromatic, care must be taken in analyzing the OCT signal with respect to the UF laser pulse beam 66 focal location. A calibration or registration procedure as a function of X, Y, and Z can be conducted in order to match the OCT signal information to the UF laser pulse beam focus location and also to the relative to absolute dimensional quantities.

There are many suitable possibilities for the configuration of the OCT interferometer. For example, alternative suitable configurations include time and frequency domain approaches, single and dual beam methods, swept source, etc., are described in U.S. Pat. Nos. 5,748,898; 5,748,352; 5,459,570; 6,111,645; and 6,053,613.

The system 2 can be set to locate the anterior and posterior surfaces of the lens capsule and cornea and ensure that the UF laser pulse beam 66 will be focused on the lens capsule and cornea at all points of the desired opening. Imaging modalities and techniques described herein, such as for example, Optical Coherence Tomography (OCT), and such as Purkinje imaging, Scheimpflug imaging, confocal or nonlinear optical microscopy, fluorescence imaging, ultrasound, structured light, stereo imaging, or other known ophthalmic or medical imaging modalities and/or combinations thereof may be used to determine the shape, geometry, perimeter, boundaries, and/or 3-dimensional location of the lens and lens capsule and cornea to provide greater precision to the laser focusing methods, including 2D and 3D patterning. Laser focusing may also be accomplished using one or more methods including direct observation of an aiming beam, or other known ophthalmic or medical imaging modalities and combinations thereof, such as but not limited to those defined above.

Optical imaging of the cornea, anterior chamber and lens can be performed using the same laser and/or the same scanner used to produce the patterns for cutting. Optical imaging can be used to provide information about the axial location and shape (and even thickness) of the anterior and posterior lens capsule, the boundaries of the cataract nucleus, as well as the depth of the anterior chamber and features of the cornea. This information may then be loaded into the laser 3-D scanning system or used to generate a three dimensional model/representation/image of the cornea, anterior chamber, and lens of the eye, and used to define the cutting patterns used in the surgical procedure.

Observation of an aim beam can also be used to assist in positioning the focus point of the UF laser pulse beam 66. Additionally, an aim beam visible to the unaided eye in lieu of the infrared OCT sample portion beam 102 and the UF laser pulse beam 66 can be helpful with alignment provided the aim beam accurately represents the infrared beam parameters. The alignment guidance subsystem 48 is included in the assembly 62 shown in FIG. 3A. An aim beam 108 is generated by an aim beam light source 110, such as a laser diode in the 630-650 nm range.

Once the aim beam light source 110 generates the aim beam 108, the aim beam 108 is transmitted along an aim path 112 to the shared optics 50, where it is redirected by a beam combiner 114. After being redirected by the beam combiner 114, the aim beam 108 follows a shared path with the UF laser pulse beam 66 through the shared optics 50 and the patient interface 52. In this way, the aim beam 108 is indicative of the location of the UF laser pulse beam 66. The aim beam 108 passes through the Z-telescope 84, is redirected by the X-scan device 86 and by the Y-scan device 88, passes through the beam combiner 90, passes through the objective lens assembly 94 and the patient interface 52, and on into the patient's eye 43.

The video subsystem 92 is operable to obtain images of the patient interface and the patient's eye. The video subsystem 92 includes a camera 116, an illumination light source 118, and a beam combiner 120. The video subsystem 92 gathers images that can be used by the control electronics 54 for providing pattern centering about or within a predefined structure. The illumination light source 118 can be generally broadband and incoherent. For example, the light source 118 can include multiple LEDs. The wavelength of the illumination light source 118 is preferably in the range of 700 nm to 750 nm, but can be anything that is accommodated by the beam combiner 90, which combines the light from the illumination light source 118 with the beam path for the UF laser pulse beam 66, the OCT sample beam 102, and the aim beam 108 (beam combiner 90 reflects the video wavelengths while transmitting the OCT and UF wavelengths). The beam combiner 90 may partially transmit the aim beam 108 wavelength so that the aim beam 108 can be visible to the camera 116. An optional polarization element can be disposed in front of the illumination light source 118 and used to optimize signal. The optional polarization element can be, for example, a linear polarizer, a quarter wave plate, a half-wave plate or any combination. An additional optional analyzer can be placed in front of the camera. The polarizer analyzer combination can be crossed linear polarizers thereby eliminating specular reflections from unwanted surfaces such as the objective lens surfaces while allowing passage of scattered light from targeted surfaces such as the intended structures of the eye. The illumination may also be in a dark-filed configuration such that the illumination sources are directed to the independent surfaces outside the capture numerical aperture of the image portion of the video system. Alternatively the illumination may also be in a bright field configuration. In both the dark and bright field configurations, the illumination light source can be used as a fixation beam for the patient. The illumination may also be used to illuminate the patient's pupil to enhance the pupil iris boundary to facilitate iris detection and eye tracking. A false color image generated by the near infrared wavelength or a bandwidth thereof may be acceptable.

The illumination light from the illumination light source 118 is transmitted through the beam combiner 120 to the beam combiner 90. From the beam combiner 90, the illumination light is directed towards the patient's eye 43 through the objective lens assembly 94 and through the patient interface 94. The illumination light reflected and scattered off of various structures of the eye 43 and patient interface travel back through the patient interface 94, back through the objective lens assembly 94, and back to the beam combiner 90. At the beam combiner 90, the returning light is directed back to the beam combiner 120 where the returning light is redirected toward the camera 116. The beam combiner can be a cube, plate or pellicle element. It may also be in the form of a spider mirror whereby the illumination transmits past the outer extent of the mirror while the image path reflects off the inner reflecting surface of the mirror. Alternatively, the beam combiner could be in the form of a scraper mirror where the illumination is transmitted through a hole while the image path reflects off of the mirrors reflecting surface that lies outside the hole. The camera 116 can be a suitable imaging device, for example but not limited to, any silicon based detector array of the appropriately sized format. A video lens forms an image onto the camera's detector array while optical elements provide polarization control and wavelength filtering respectively. An aperture or iris provides control of imaging NA and therefore depth of focus and depth of field and resolution. A small aperture provides the advantage of large depth of field that aids in the patient docking procedure. Alternatively, the illumination and camera paths can be switched. Furthermore, the aim light source 110 can be made to emit infrared light that would not be directly visible, but could be captured and displayed using the video subsystem 92.

Figure 3B:
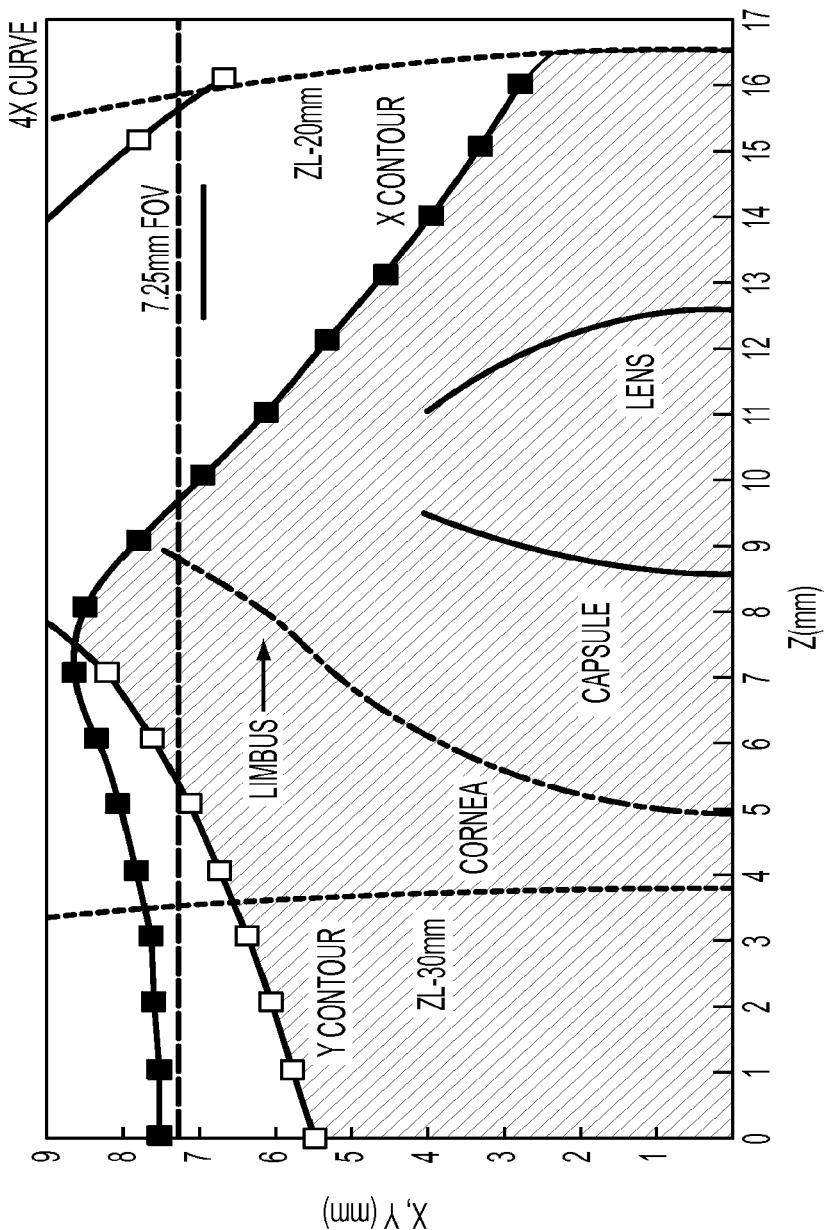
FIG. 3B shows a mapped treatment region of the eye comprising the cornea, the posterior capsule, and the limbus, in accordance with many embodiments.

FIG. 3B shows a mapped treatment region of the eye comprising the cornea, the posterior capsule, and the limbus. The treatment region can be mapped with computer modeling, for example ray tracing and phased based optical modeling to incorporate factors such as laser beam quality, pulse width, system transmission, numerical aperture, polarization, aberration correction, and alignment. The treatment volume is shown extending along the Z-axis from the posterior surface of the optically transmissive structure of the patient interface a distance of over 15 mm, such that the treatment volume includes the cornea, and the lens in which the treatment volume of the lens includes the anterior capsule, the posterior capsule, the nucleus and the cortex. The treatment volume extends laterally from the center of the cornea to beyond the limbus. The lateral dimensions of the volume are defined by a Y contour anterior to the limbus and by an X contour posterior to the limbus. The treatment volume shown can be determined by a person of ordinary skill in the art based on the teachings described herein. The lateral positions of predicted optical breakdown for ZL fixed to 30 mm and ZL fixed to 20 mm are shown. These surfaces that extend transverse to the axis 99 along the Z-dimension correspond to locations of optical scanning of the X and Y galvos to provide optical breakdown at lateral locations away from the axis 99. The curved non-planar shape of the scan path of optical breakdown for ZL-30 mm and ZL-20 mm can be corrected with the mapping and look up tables as described herein. The curved shape of the focus can be referred to as a warping of the optical breakdown depth and the look up tables can be warped oppositely or otherwise adjusted so as to compensate for the warping of the treatment depth, for example. Additionally, the warping inherent in the prediction from the model can be incorporated in the generic look-up table and any further error from this predicted form as indicated by measurement and application of a correction factor to offset this error may also be called a warping of the look up table.

The treatment region is shown for setting the laser beam energy about four times the threshold amount for optical breakdown empirically determined for a beam near the limbus of the system. The increased energy or margin above ensures that the beam system will be able to treat given variability in contributing factors. Theses contributing factors may include degradation over lifetime of the laser with regard to energy, beam quality, transmission of the system, and alignment.

The placement of the posterior surface of the optically transmissive structure of the patient interface away from the surface of the cornea can provide the extended treatment range as shown, and in many embodiments the optically transmissive structure comprises the lens. In alternative embodiments, the posterior surface of the optically transmissive structure can be placed on the cornea, for example, and the mapping and look up tables as described herein can be used to provide the patient treatment with improved accuracy.

The optically transmissive structure of the patient interface may comprise one or more of many known optically transmissive materials used to manufactures lenses, plates and wedges, for example one or more of glass, BK-7, plastic, acrylic, silica or fused silica for example.

The computer mapping of the treatment volume may optionally be adjusted with mapping based on measurements of a constructed system as described herein.

Figure 3C:
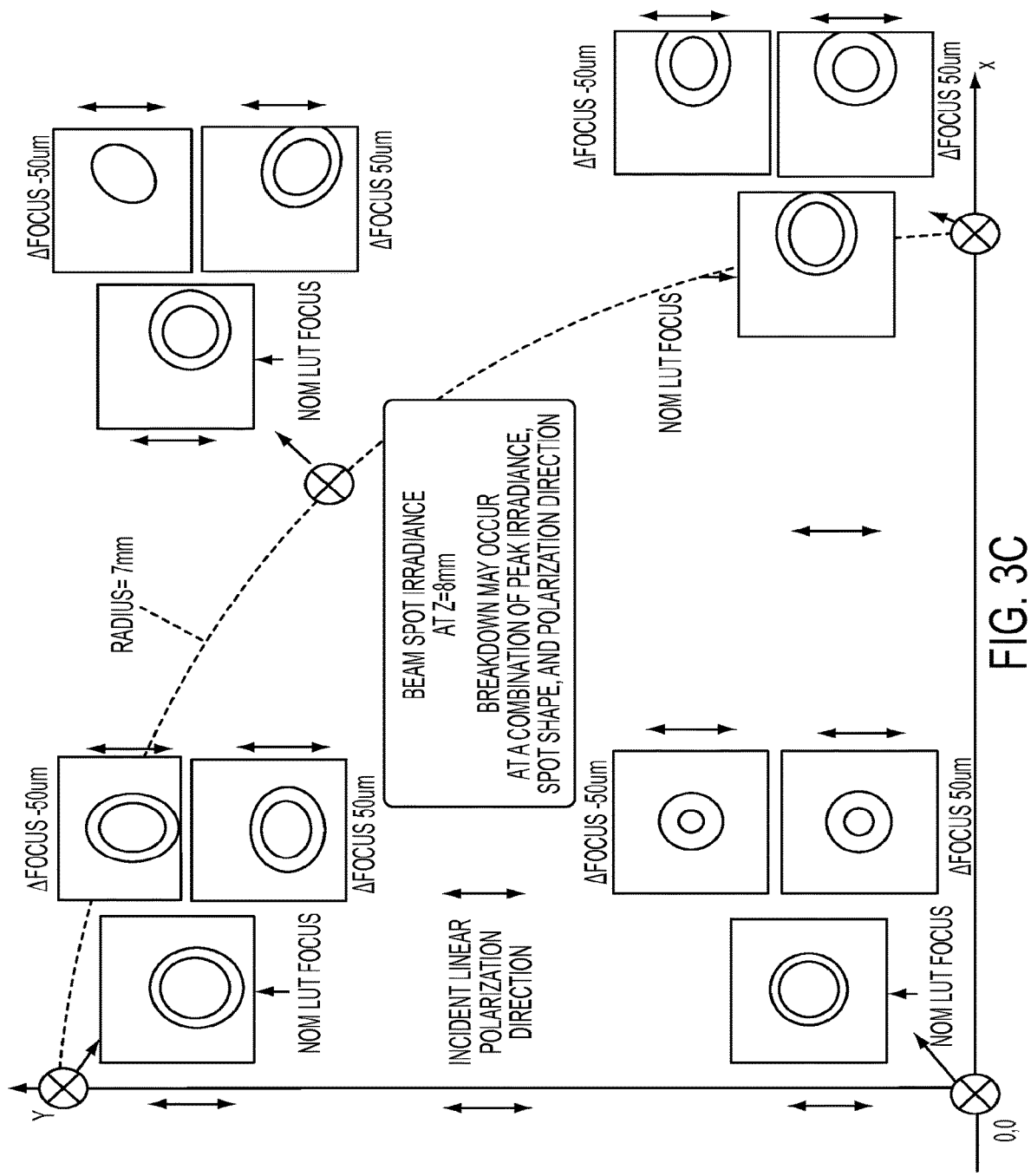
FIG. 3C shows mapped changes in beam focus for locations of the mapped treatment region, in accordance with many embodiments.

FIG. 3C shows mapped changes in beam focus for locations of the mapped treatment region. The locations of optical breakdown can be mapped at a plurality of depths and lateral locations so as to map the location of optical breakdown over the treatment volume. The laser beam spot irradiance can be determined with computer modeling software, for example. The location of optical breakdown can be determined based on the laser beam spot irradiance pattern, such that the location of optical breakdown along the laser beam path can be determined. The optical breakdown for a given set of laser parameters such as beam quality and pulse width can occur at a combination of one or more of peak irradiance, spot shape, or polarization direction, for example. The mapped beam shape can be at planes of a treatment volume, for example. The mapped focus can be determined with commercially available optical modeling software based on the teachings described herein. The mapped changes in beam focus may comprise a mapped focus at a depth of 8 mm on the axis of the coordinate reference system, for example. Similar mapping can be performed at additional depths as described herein. The focused beam profile can be determined for the nominal location and +50 um and −50 um, so as to evaluate the irradiance pattern to determine the location of optical breakdown. The focused beam profile can be determined at several locations along the plane away from the axis. For example, the beam profile can be determined at locations along a radius of the treatment volume, such as at the 0, 45 and 90 degree locations along a 7 mm circle, for example.

In many embodiments, the laser beam output energy comprises a value substantially above the amount required near the center of the treatment volume, for example four times the amount required at the center, so as to provide optical breakdown near the edges of the treatment volume, and the location of optical breakdown can be determined based on the beam spot irradiance profile and the output energy of the laser. This mapping can be performed initially in software, and may optionally be further refined based on mapping measurements of a constructed system as described herein.

Figure 4A:
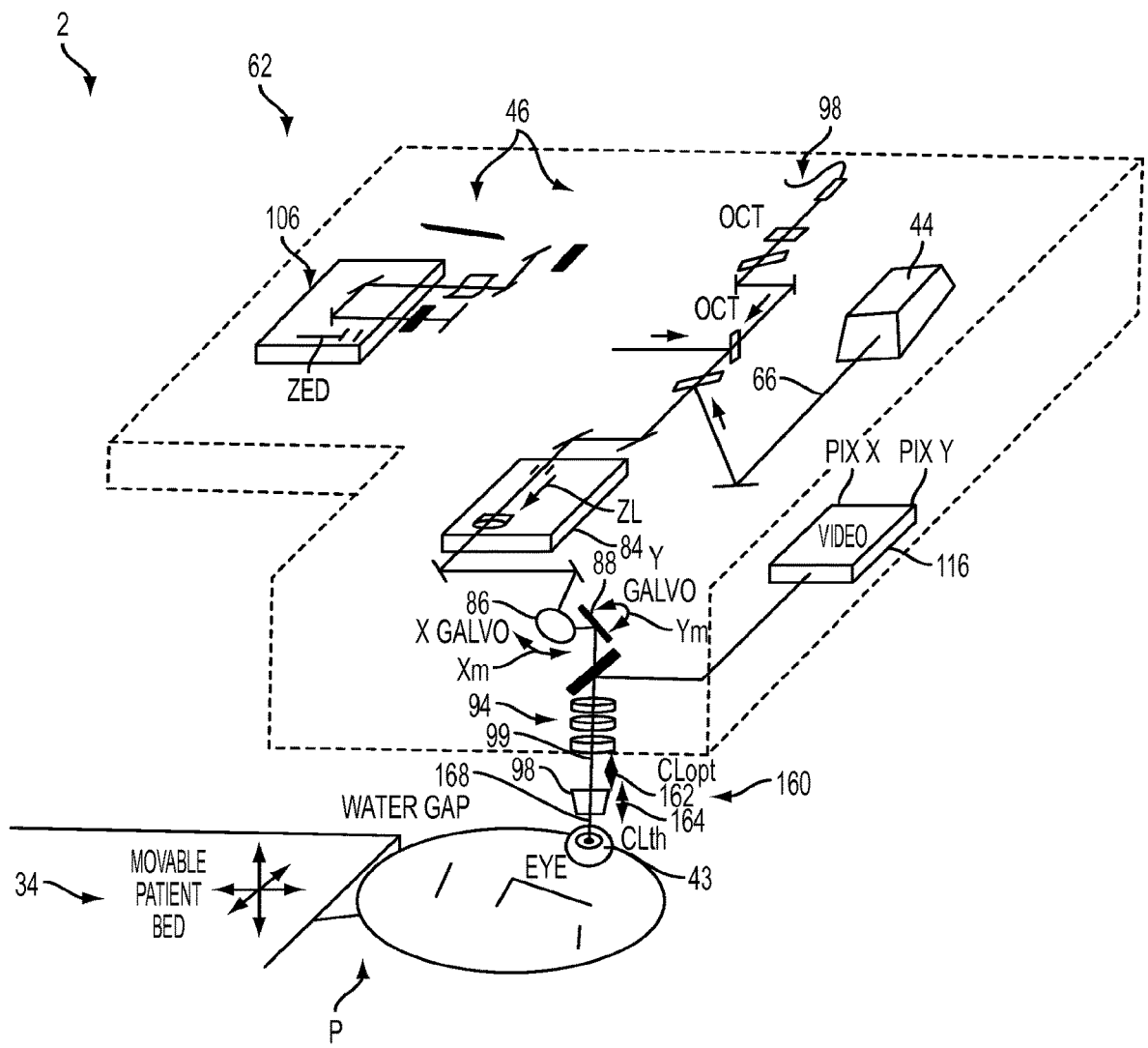
FIG. 4A shows correspondence among movable and sensor components of the laser delivery system, in accordance with many embodiments.

FIG. 4A shows correspondence among movable and sensor components of the laser delivery system 2. The movable components may comprise one or more components of the laser delivery system 2 as described herein. The movable components of the laser delivery system may comprise the zoom lens capable of moving distance ZL, the X galvo mirror 96 capable of moving an angular amount Xm, and the Y galvo mirror 88 capable of moving an angular amount Ym. The movable components of the OCT system may comprise the movable OCT reference arm configured to move the reference path 106 a distance ZED. The sensor components of the laser system may comprise the video camera having X and Y pixels, Pix X and Pix Y, respectively, and sensor components of the OCT system such as the spectral domain detection as described herein. The patient support which may comprise a bed is movable in three dimensions so as to align the eye 43 of the patient P with laser system 2 and axis 99 of the system. The patient interface assembly comprises an optically transmissive structure which may comprise an interface lens 96, for example, configured to be aligned with system 2 and an axis of eye 43. The patient interface lens can be placed on the patient eye 43 for surgery, and the optically transmissive structure can be placed at a distance 162 from the objective lens 94. In many embodiments, the optically transmissive structure comprises lens 96 placed a contact lens optical distance 162 (hereinafter "CLopt"). The optically transmissive structure comprises a thickness 164, and the thickness 164 may comprise a thickness of the contact lens 96, for example. Although the optically transmissive structure comprising contact lens 96 may contact the eye 2, in many embodiments the contact lens 168 is separated from the cornea with gap 168 extending between the lens and the vertex of the cornea, such that the posterior surface of the contact lens 168 contacts a solution comprising saline or a viscoelastic solution, for example.

Figure 4B:
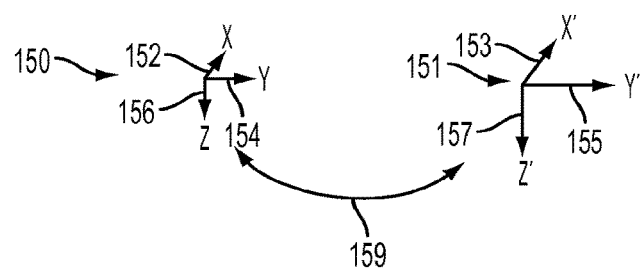
FIG. 4B shows mapping of coordinate references from an eye space coordinate reference system to a machine coordinate reference system, in accordance with many embodiments.

FIG. 4B shows mapping of coordinate references from an eye space coordinate reference system 150 to a machine coordinate reference system 151 so as to coordinate the machine components with the physical locations of the eye. The laser system 2 can map physical coordinates of the eye 43 to machine coordinates of the components as described herein. The eye space coordinate reference system 150 comprises a first X dimension 152, for example an X axis, a second Y dimension 154, for example a Y axis, and a third Z dimension 156, for example a Z axis, and the coordinate reference system of the eye may comprise one or more of many known coordinate systems such as polar, cylindrical or Cartesian, for example.

In many embodiments, the eye coordinate reference system corresponds to physical dimensions of the eye, which can be determined based on the tomography, video, and other measurements of the eye corrected with the refraction of the eye and the index of refraction of the eye as described herein, for example. For a targeted physical location of the eye having eye coordinate references based on the coordinate reference system 150, the processor can determine the machine coordinates of the machine coordinate reference system in one or more of many ways as described herein.

In many embodiments the reference system 150 comprises a right handed triple with the X axis oriented in a nasal temporal direction on the patient, the Y axis oriented superiorly on the patient and the Z axis oriented posteriorly on the patient. In many embodiments, the corresponding machine coordinate reference system 151 comprises a first X' dimension 153, a second Y' dimension 155, and a third Z' dimension 157 generally corresponding to machine actuators, and the coordinate reference system of the machine may comprise one or more of many known coordinate systems such as polar, cylindrical or Cartesian, and combinations thereof, for example.

The machine coordinate reference 151 may correspond to locations of one or more components of system 2. The machine coordinate reference system 151 may comprise a plurality of machine coordinate reference systems. The plurality of machine coordinate reference systems may comprise a coordinate reference system for each subsystem, for example. For example, dimension 157 may correspond to movement of the z-telescope lens capable of moving distance ZL. The dimension 153 may correspond to movement of the X galvo mirror 86 capable of moving an angular amount Xm, and the dimension 153 may correspond to movement of the Y galvo mirror 88 capable of moving an angular amount Ym. Alternatively or in combination, the dimension 157 may correspond to movable OCT reference arm configured to move the reference path 106 a distance ZED, along with dimension 157 corresponding to a movement of the z-telescope for the OCT beam, and the dimension 153 and the dimension 155 may correspond to movement of the X galvo mirror 86 and the Y galvo mirror 88, respectively, for the OCT beam. The dimension 151 may correspond to X pixels of the video camera and dimension 153 may correspond to Y pixels of the video camera. The axes of the machine coordinate reference system may be combined in one or more of many ways, for example the OCT reference arm movement of the reference path 106 the distance ZED can be combined with movement of the z-telescope lens capable of moving the distance ZL, for example. In many embodiments, the locations of the components of the laser system 2 are combined when in order to map the plurality of machine coordinate reference systems to the coordinate reference system 150 of eye 43.

In many embodiments, the eye coordinate reference system is mapped from an optical path length coordinate system to physical coordinates of the eye based on the index of refraction of the tissues of the eye. An example is the OCT ranging system where measurements are based on optical thicknesses. The physical distance can be obtained by dividing the optical path length by the index of refraction of the material through which the light beam passes. Preferable the group refractive index is used and takes into account the group velocity of the light with a center wavelength and bandwidth and dispersion characteristics of the beam train. When the beam has passed through more than one material, the physical distance can be determined based on the optical path length through each material, for example. The tissue structures of the eye and corresponding index of refraction can be identified and the physical locations of the tissue structures along the optical path determined based on the optical path length and the indices of refraction. When the optical path length extends along more than one tissue, the optical path length for each tissue can be determined and divided by the corresponding index of refraction so as to determine the physical distance through each tissue, and the distances along the optical path can be combined, for example with addition, so as to determine the physical location of a tissue structure along the optical path length. Additionally, optical train characteristics may be taken into account. As the OCT beam is scanned in the X and Y directions and departure from the telecentric condition occurs due to the axial location of the galvo mirrors, a distortion of the optical path length is realized. This is commonly known as fan error and can be corrected for either through modeling or measurement.

As one or more optical components and light sources as described herein may have different path lengths, wavelengths, and spectral bandwidths, in many embodiments the group index of refraction used depends on the material and the wavelength and spectral bandwidth of the light beam. In many embodiments, the index of refraction along the optical path may change with material. For example, the saline solution may comprise a first index of refraction, the cornea may comprise a second index of refraction, the anterior chamber of the eye may comprise a third index of refraction, and the eye may comprise gradient index lens having a plurality of indices of refraction. While optical path length through these materials is governed by the group index of refraction, refraction or bending of the beam is governed by the phase index of the material. Both the phase and group index can be taken into account to accurately determine the X, Y, and Z location of a structure. While the index of refraction of tissue such as eye 43 can vary with wavelength as described herein, approximate values include: aqueous humor 1.33; cornea 1.38; vitreous humor 1.34; and lens 1.36 to 1.41, in which the index of the lens can differ for the capsule, the cortex and the nucleus, for example. The phase index of refraction of water and saline can be about 1.325 for the ultrafast laser at 1030 nm and about 1.328 for the OCT system at 830 nm. The group refractive index of 1.339 differs on the order of 1% for the OCT beam wavelength and spectral bandwidth. A person of ordinary skill in the art can determine the indices of refraction and group indices of refraction of the tissues of the eye for the wavelengths of the measurement and treatment systems as described herein. The index of refraction of the other components of the system can be readily determined by a person of ordinary skill in the art based on the teachings described herein.

Figure 4C:
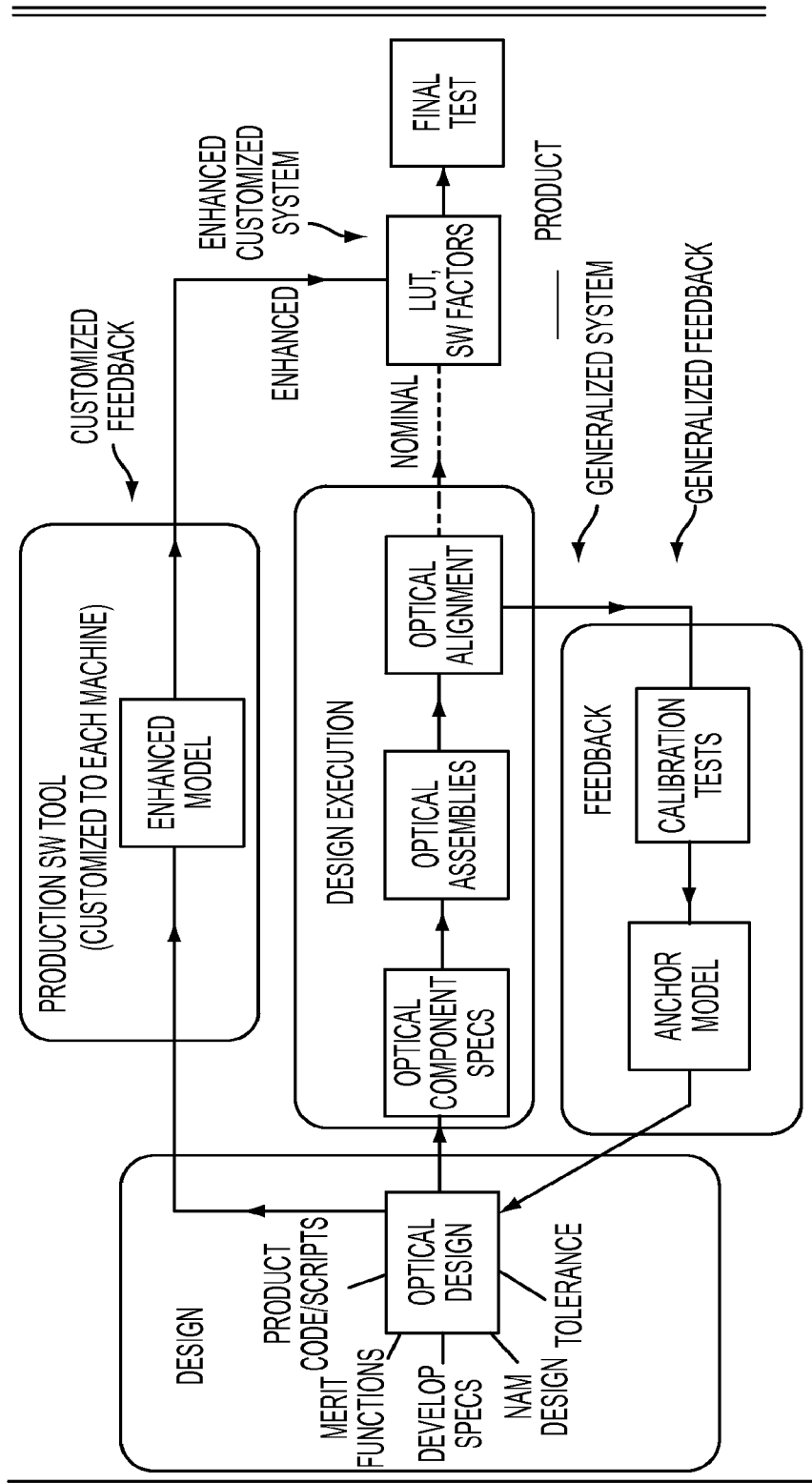
FIG. 4C shows a feedback loop to adjust look up table calibration mapping from a generalized system to a specific individual constructed system based on measurements of the individual constructed system, in accordance with many embodiments.

FIG. 4C shows a feedback loop to adjust look up table calibration mapping from a generalized system having nominal values to a specific individual constructed system based on measurements of the individual constructed system. The system 2 may comprise a generalized system based on optical schematics and components. The generalized system may comprise an optical design as described herein, which can be associated with one or more of product code and scripts, merit functions, optical specifications, a nominal system design of the components and locations, and tolerances associated with the nominal system design components and locations. In the execution of the system design, the optical design is output as optical components and specifications, which can be used to configured optical assemblies. The optical assemblies and components are aligned. The generalized system design can be further improved with feedback. The feedback of the generalized system design may comprise calibration tests and optical modeling that are used to further improve and modify the optical design. For example, a system can be constructed based on the nominal design and information from the nominal design fed back to the optical design based on calibration and testing, such as tolerances of components and range of treatment. The nominal design of the general system can be used to generate a generalized look up table based on the nominal design. The nominal LUTS and SW factors can be used to produce a final production system, and the final production system can undergo final test procedures.

In accordance with many embodiments, an enhanced customized system 2 can be constructed based on the customized feedback path so as to provide a customized system. While the customized system can be provided in many ways, in many embodiments a production SW tool is used to customize the parameters of individual system so as to provide an enhanced model of system behavior and improved accuracy of the mapping as described herein. The production SW tool can be used to determine customized look up tables of the system 2, and to provide enhanced calibration of system 2. The nominal values output from the generalized nominal system at design execution stage can be output to the LUTs and software factors, which can be combined with the customized feedback to provide an enhanced product. The modification to the LUTs to transform the system 2 from the generalized nominal system to the constructed system with customized parameters can be provided with calibration of the constructed system as described herein.

Figure 5:
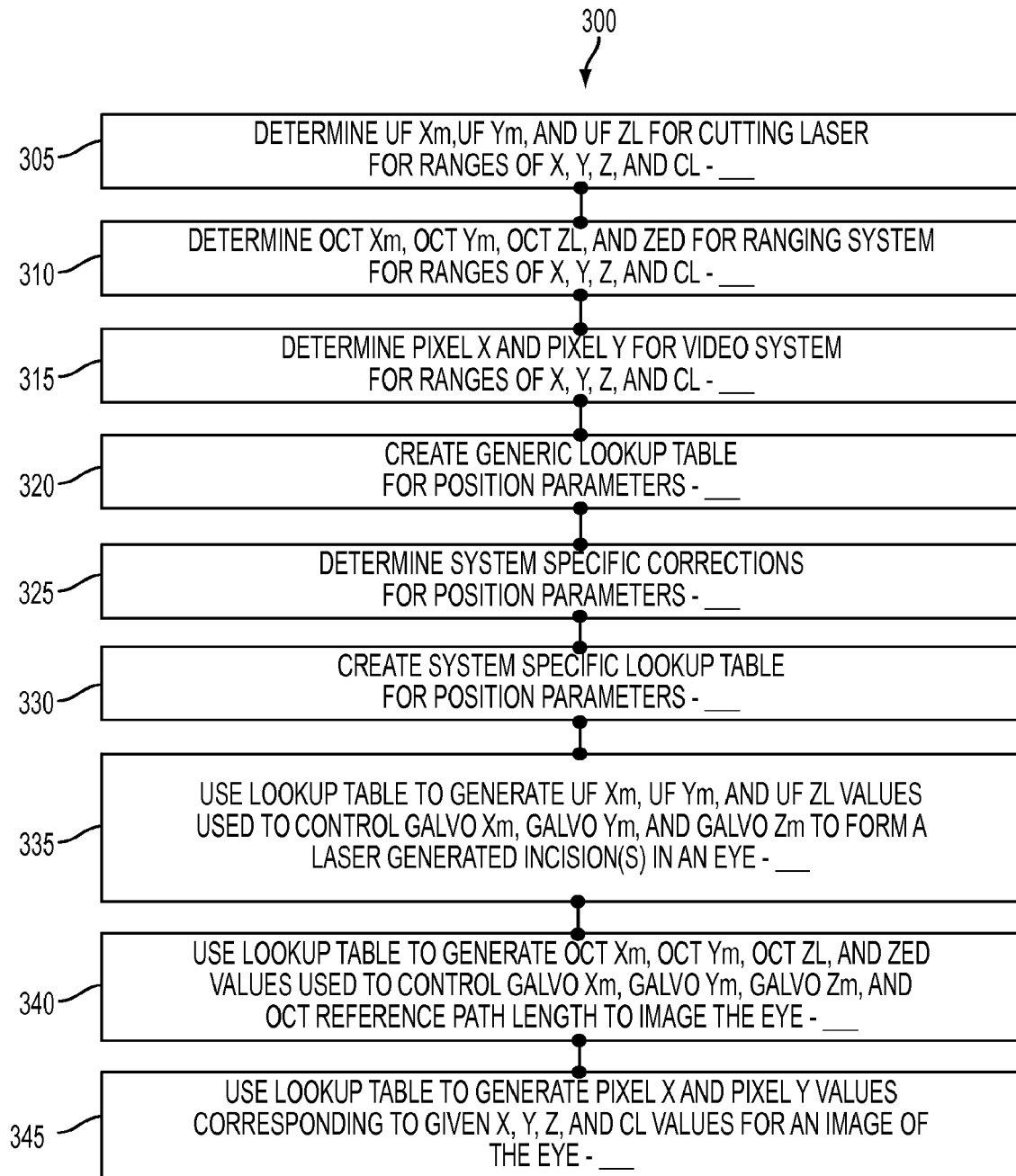
FIG. 5 shows a method of calibration a laser system, in accordance with many embodiments.

FIG. 5 shows a method 300 of calibration for laser system 2. The laser system 2 can be calibrated such that positions and angles of the components and actuators of the laser system are mapped onto locations of the eye 43. The method 300 can be performed on each build of a laser system, and can be used to improve the accuracy of a specific laser system. In many embodiments, the system specific calibration can be used to improve the correspondence between the treatment locations of the eye and the machine coordinates as described herein. Although reference is made to Z-axis alignment, similar methods and apparatus can be used to improve the accuracy of the system along other dimensions, such as X and Y dimensions, for example. Method 300 can be combined with optical breakdown threshold energy mapping as described herein, for example. Method 300 can be particularly well suited for calibration of the system with a first lens of the patient interface, in order to use a second lens of the patient interface to treat the patient accurately. A plurality of many additional patient interface lenses can be used based on the alignment with the first lens, for example. The methods and apparatus can be used to determine specific laser treatment parameters for a specific patient interface lens placed in the system for a specific eye, for example.

At a step 305, values of Xm, Ym, and ZL (where Xm corresponds to the angle of the X galvo mirror, Ym corresponds to the angle of the Y galvo mirror, and ZL corresponds to the movement of the lens in the z-telescope) are determined within a treatment volume for the ultrafast femto second laser so as to provide corresponding X, Y and Z locations of the eye. The locations can be determined based on mapping and look up tables (herein after "LUT"), for example. The mapped locations can depend on the location and shape of the optically transmissive structure such as lens 168, the distance 162, distance 164, and the distance 168, for example. The mapping locations may also depend on the laser characteristics such as beam quality, pulse width, polarization, and energy per pulse. The mapping locations may also depend on the characteristics of the optical system such as axial magnification, lateral magnification, numerical aperture, degree of telecentricity, aberration, and alignment.

At a step 310, values of Xm, Ym, ZL and ZED (where Xm, Ym, and ZL are defined as before and ZED corresponds to the position of the OCT reference path length stage) are determined within a measurement volume for the tomography system (such as the OCT system) so as to provide corresponding X, Y and Z locations of the eye or patient interface. The locations can be determined based on mapping and look up tables, for example. The tomography system may comprise one or more of an OCT system, a confocal system, or a Scheimpflug system, an ultrasound system, a high frequency ultrasound system, for example. The mapped locations can depend on the location and shape of the optically transmissive structure such as lens 168, the distance 162, distance 164, and the distance 168, for example. The mapping locations may also depend on the light source characteristics such as wavelength, spectral bandwidth, and polarization. The mapping locations may also depend on the characteristics of the optical system such as axial magnification, lateral magnification, numerical aperture, degree of telecentricity, aberration, and alignment.

At a step 315, values pixel X and pixel Y are determined within a measurement volume for the video system so as to provide corresponding X, Y, and Z locations of the eye or patient interface. The locations can be determined based on mapping and look up tables, for example. The video is primarily a two-dimensional mapping of Xm, Ym to X, Y. Because of the large depth of field of the imaging path and the telecentric form, the Z location remains unchanged for the range of Z for which the image is in focus. Accurate Z location can be determined using the OCT ranging system or a priori knowledge. The mapped locations can depend on the location and shape of the optically transmissive structure such as lens 168, the distance 162, distance 164, and the distance 168, for example. The mapping locations may depend on the characteristics of the optical system such as axial magnification, lateral magnification, numerical aperture, degree of telecentricity, aberration, and alignment.

At a step 320, a generic look up table is determined for the position parameters of the system in response to targeted locations of the eye. The generic look up table can combine the above mapped values of Xm, Ym, ZL, & ZED based on one or more of distance 162, distance 164, distance 168, dimension 152, dimension 154 or dimension 156, and combinations thereof for example. The generic look up table can be constructed based on ray tracing or other optically based analysis such as diffraction or wave based or gaussian beam propagation of the nominal optical components of the system and the movable components of the system to include the X galvo, the Y galvo, the Z-telescope, the attenuator, and the chair, for example. The generic values of the look up table can map each eye coordinate location to a specific location or angle of each of the values of Xm, Ym, ZL, & ZED and other machine controllable dimensions, for each of the UF laser, the OCT system and the video system and aim alignment, for example. Although a look up table is described, the mapping can be performed in one or more of many ways.

At a step 325, system specific corrections to the generic values are determined. The system specific look up table can be customized to the manufactured configuration of the system, and is capable of accommodating variation of the mapped components. The variation may occur with parts manufactured within specification but slightly different from the generic or nominal system. For example, the optical power, placement and dimensions of the manufactured components may differ slightly from the generic system. The system specific LUT can be generated based on the teachings described herein.

At a step 330, a system specific look up table (or tables) is determined based on the system specific corrections. The system specific look up table can be combined with the generic look up table in many ways, for example with corrections or adjustments comprising subtractions or additions and scalings to the generic look up table.

At a step 335, the system specific look up table is used to generate a laser treatment of the eye so as to form laser generated incisions of the eye. The system specific look up table can be combined with a treatment table comprising a plurality of eye coordinate references, so as to provide specific instructions to components of the laser system for each location of the eye treatment given variations in known dependencies such as from patient interface variations. The system specific look up table can be used to generate values of UF Xm, UF Ym, and UF ZL in order to control the positions of the corresponding components.

At a step 340, At a step 335, the system specific look up table is used to generate tomography values, such as values of OCT Xm, OCT Ym, OCT ZL and ZED values, so as to control Galvo Xm, Galvo Ym, Galvo Zm, and the OCT reference path length in order to image the eye and patient interface given variations in known dependencies such as from patient interface variations. The system specific look up table can be used to generate values of OCT Xm, OCT Ym, OCT ZL in order to control the positions of the corresponding components and ensure that the physical locations of the eye structures and patient interface are accurately mapped.

At a step 345, the system specific look up table is used to generate the Pixel X and Pixel Y values corresponding to the given X, Y, Z, and CL thickness and displacement values used to form an image of the eye and patient interface on the camera sensor array, and so as to accurately map the eye structures to three dimensional space in accordance with eye coordinate reference system 150.

Although the above steps show method 300 of calibrating in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as if beneficial to the treatment.

One or more of the steps of the method 300 may be performed with the circuitry as described herein, for example one or more of the processor or logic circuitry such as the programmable array logic for field programmable gate array. The circuitry may be programmed to provide one or more of the steps of method 300, and the program may comprise program instructions stored on a computer readable memory or programmed steps of the logic circuitry such as the programmable array logic or the field programmable gate array, for example.

Figure 6A:
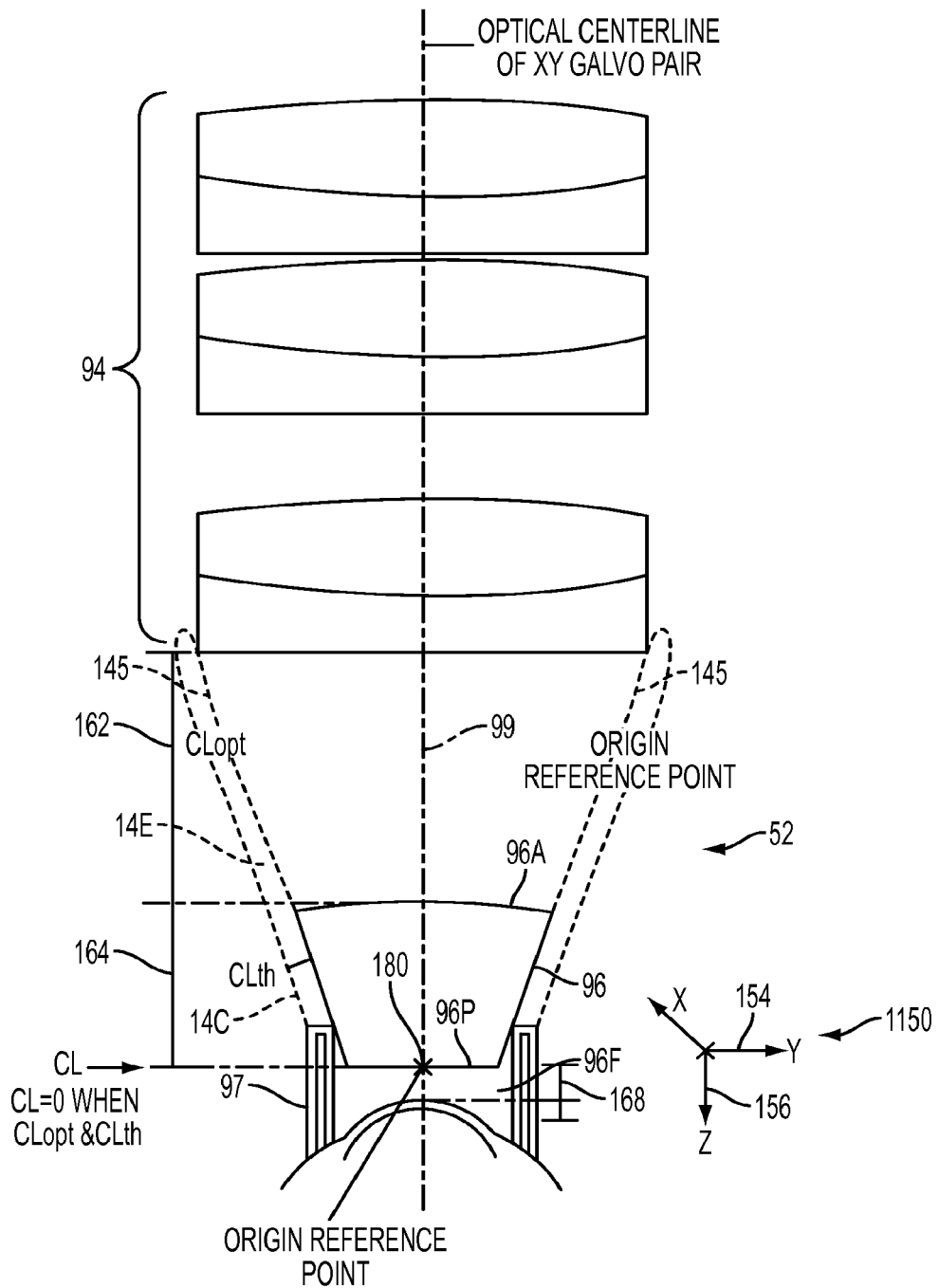
FIG. 6A shows an eye coordinate reference system referenced to a lower surface of an optically transmissive structure of a patient interface, in accordance with many embodiments.

FIG. 6A shows an eye coordinate reference system 150 referenced to a lower surface of an optically transmissive structure as part of a patient interface. The eye coordinate reference system can be mapped to the machine coordinate reference system 151 as described herein.

The optically transmissive structure may comprise a flat plate, or a lens having one or more curved surfaces. In many embodiments, the optically transmissive structure comprises lens 96. The objective lens 94 may comprise a plurality of achromatic infrared doubles, for example three achromatic infrared doublets.

The reference location 180 may comprise the origin of the coordinate system 150, and can be located in one or more of many places, such as the posterior surface 96P of the optically transmissive structure, located opposite an anterior surface 96A of lens 96. The gap distance 168 between the cornea and posterior surface 96P can be within a range from about 1 to 10 mm, for example. The thickness 164 of the optically transmissive structure can be within a range from about 1 to 20 mm, for example about 12 mm. A distance 162 from the distal lower surface of the objective lens to the anterior surface 96A can be any suitable distance, for example within a range from about 10 mm to about 200 mm, for example about 20 mm. In many embodiments, the patient interface assembly comprises single use disposable structures to couple the optically transmissive structure comprising lens 96 to objective lens 94 and retention ring 97 of the patient interface assembly 14.

The patient interface assembly may comprise a support structure 14S in order to place the optically transmissive structure to provide distance 162 and distance 168 in combination with thickness 164. The support structure 14S may comprise a stiff support so as to resist movement of the optically transmissive structure and patient ring 97 when the patient moves, for example. The support structure 14S may comprise an assembly of user combinable components such as retention ring 97, and a docking cone 14C, and an extension 14E, for example. The docking cone 14C can receive the lens 96 of the conic extension section 14E, for example.

Reference 180 location can be determined in one or more of many ways. In many embodiments, location 180 comprises an intersection of axis 99 with the posterior surface 96P of the optically transmissive structure as described herein. The location 180 may comprise a reference point determined with axis 99. For example a location 180 can be located along axis 99 that intersects the posterior surface 96P based on the measured system, and the location 180 may correspond to a distance of the posterior surface of the specific system lens as compared to the lower surface of the generalized system. Alternatively, the location 180 may comprise a distance from an internal structure of laser system 2 such as a mirror of the OCT system, or a distance from the surface of one of the objective lenses such as the posterior surface of the achromatic objective lens closest to the eye. The location of axis 99 can be determined based on system calibration, and the calibration may comprise determining a location of axis 99 that retro reflects the laser beam to a point of origin within system 2, for example. The axis 99 may comprise the origin of the patient reference system 150, for example.

The deviation of the lower surface of a constructed system from the location of the generalized system can be determined and the values of the look up table determined accordingly.

The lens 96 may comprise a convexly curved posterior surface so as to urge gas bubbles to the periphery and away from the optical beam path when the posterior surface 96P contacts a liquid interface fluid 96F, such one or more of water, saline, viscous fluid, or a viscoelastic fluid. The anterior surface 96A can be provided with a curved shape or a flat shape, for example. In many embodiments, the convexly curved lower surface can extend the working range of the laser system so as to provide optical breakdown over an increased range within the eye, for example with combined corneal and cataract surgery. The dimensions of lens 96 can be determined so as to provide the extended range when spaced apart from the cornea and combined with one or more doublet lenses by a person of ordinary skill in the art based on the teachings described herein. The negative lens of the z-telescope optics may comprise radii of curvature to provide the extended range of optical breakdown when combined with the lens 96 and the one or more achromatic objective lenses. The aberrations can be controlled over the intended imaging and cutting volume of the eye and patient interface due to the balancing of contributions from the z-telescope, the objective, and the contact lens as a function of positions of the z-telescope, the X & Y galvos, and the variation of placement and thickness of the contact lens by a person of ordinary skill in the art of lens design.

The lens 96 can be configured to provide a different change in the numerical aperture of the beam focus than a flat plate, for example. In many embodiments, the lens 96 contributes a relatively small amount of focusing power when the laser beam is scanned near the cornea. However, when the laser beam is scanned at locations deeper in the eye, for example near the lens capsule, the lens 96 can provide a greater effect on the beam focus than when the beam is focused near the cornea, so as to further change the numerical aperture of the laser beam, for example.

Figure 6B:
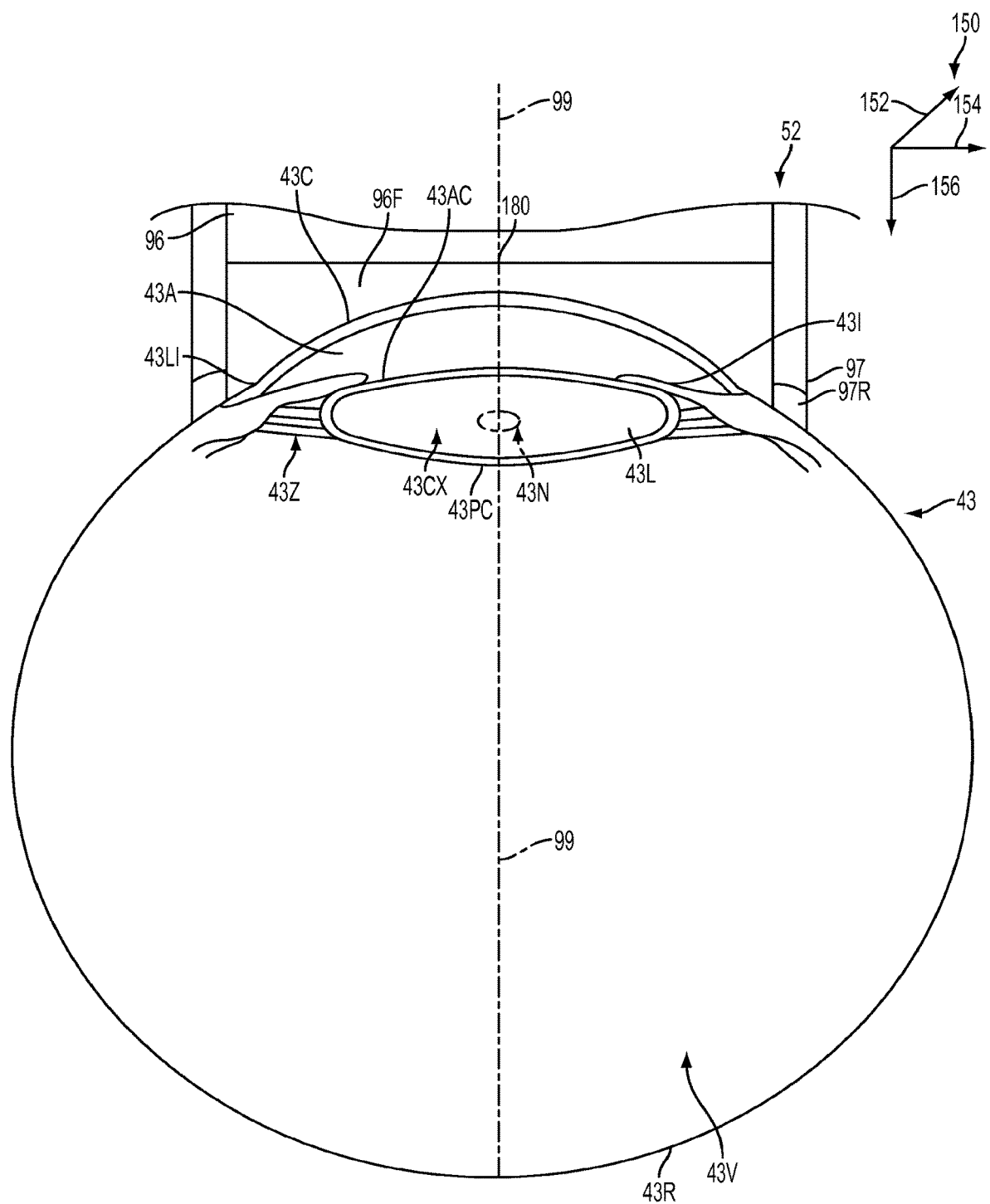
FIGS. 6B and 6C show side views and front views of structures of the eye as in FIG. 6A coupled to the patient interface and the eye coordinate reference frame for mapping to the machine coordinate reference frame, in accordance with many embodiments.
Figure 6C:
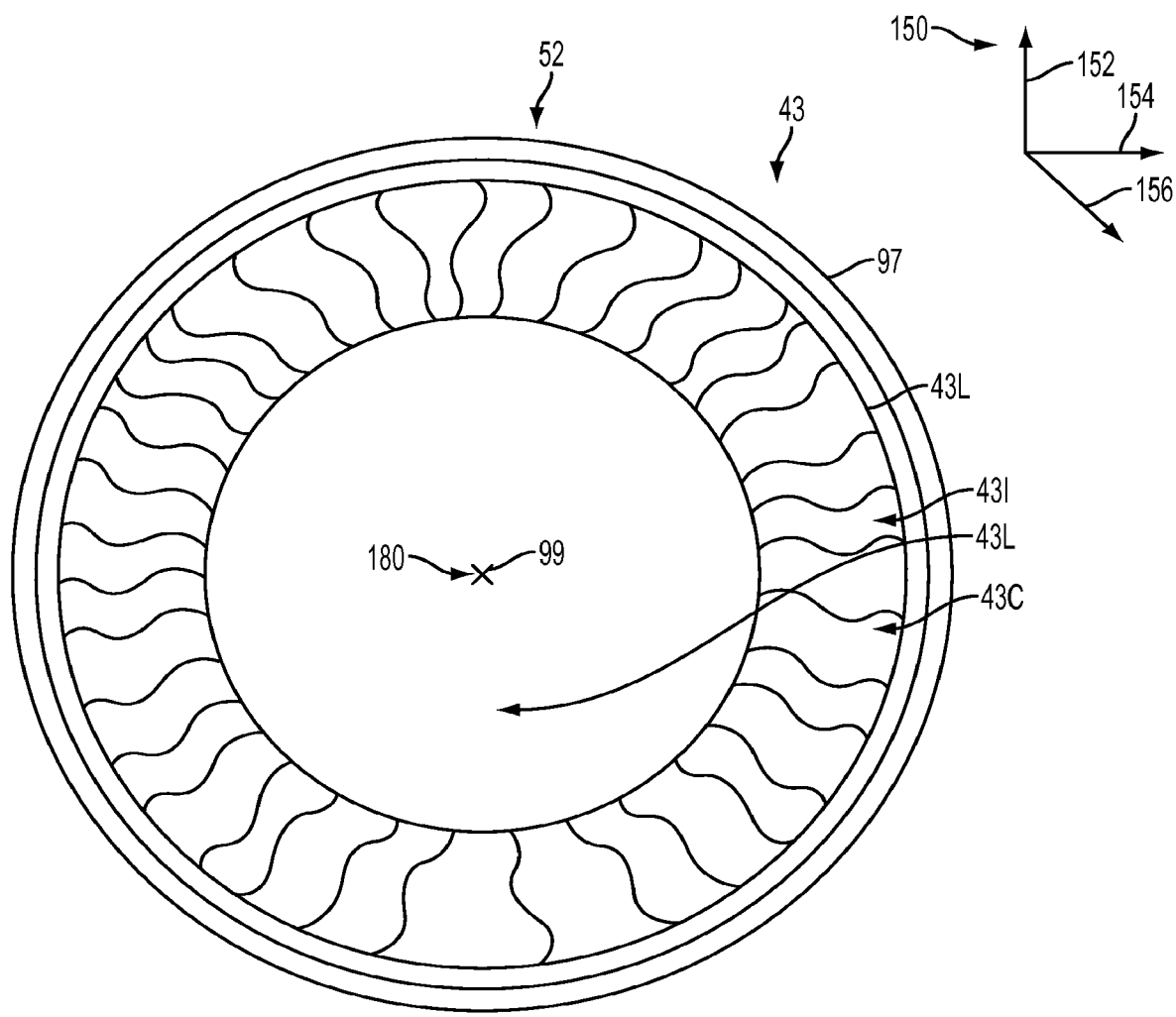

FIGS. 6B and 6C show side views and front views of structures of the eye 43 as in FIG. 6A. The structures of the eye can be coupled to the patient interface 52 for measurement and mapping with reference to the eye coordinate reference frame 150. The structures of the eye can be mapped from the eye coordinate reference system 150 to the machine coordinate reference system 151 as described herein, for example. The axis 99 can be positioned in relation to one or more of many known axis of the eye such as the visual axis of the eye or the optical axis of the eye, for example.

The structures of the eye 43 that can be measured and mapped with respect to eye coordinate reference system 150 include a cornea 43C, anterior chamber 43A, lens 43L, an iris 43I that defines a pupil of the eye, vitreous humor 43V and retina 43R. The lens 43L comprises a capsule, a cortex 43CX and a nucleus 43N. The capsule comprises an anterior capsule 43AC and a posterior capsule 43PC. Zonules 43Z of the eye 43 are coupled to the capsule of the eye. The structures of the eye can be marked with the laser beam in order to calibrate the laser system with in situ calibration as described herein. Alternatively or in combination, the structures of the eye can be marked in order to track the eye and align the eye with the laser beam as described herein.

Figure 7A:
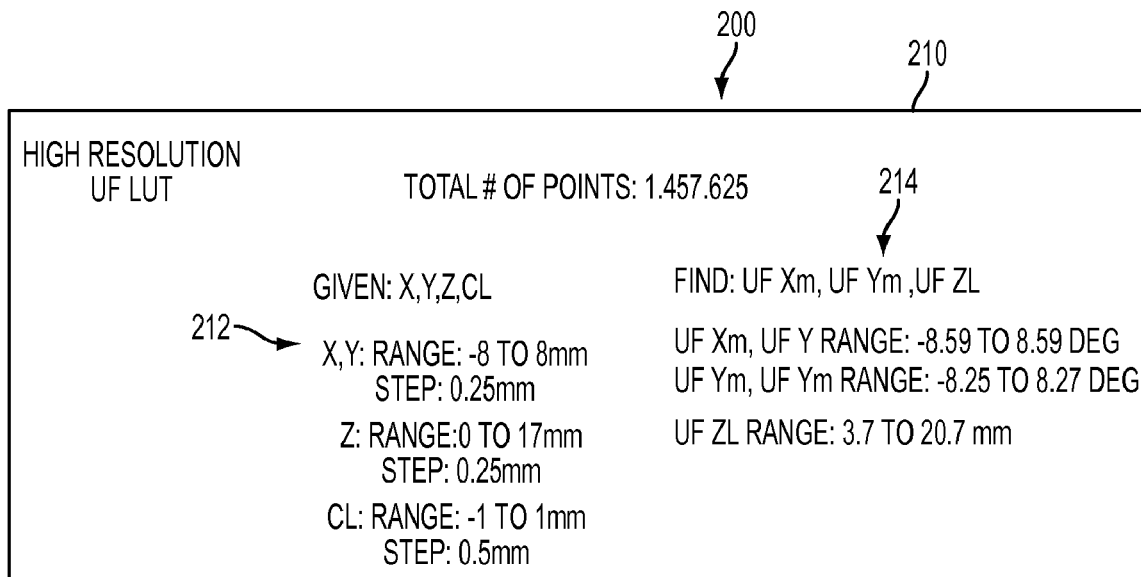
FIG. 7A shows a look up table summary for an ultrafast laser, in accordance with many embodiments.

FIG. 7A shows a look up table 210 for an ultrafast (hereinafter "UF") laser as described herein. The look up table 210 may comprise a plurality of discrete input values 212 over a range, for example four values such as X, Y, Z of patient coordinate reference system and distance CL of the lower surface of the lens, and a plurality of output values 214. The X and Y values of the eye can range from −8 to 8 mm, in 0.25 mm increments, for example. The Z value can range from 0 to 17 mm in 0.25 mm increments, for example. The CL value can range from −1 to 1 mm in 0.5 mm increments, for example. These four dimensional input values can be input into processor system and an output machine value provide for each combined input. The output values 214 of the look up table can be provided as Xm, Ym and ZL for each combined input value combination. The output of Xm and Ym can each be within a range from −8.59 degrees to 8.59 degrees of the corresponding galvanometer mirror. The output value for ZL can be within a range from 3.7 to 20.7 mm, for example. The total number of input and values of the LUT can be about 1,457,625 for each input comprising (X, Y, Z, CL) and each output comprising (Xm, Ym, ZL), for example.

FIG. 7A1 shows an optical schematic of the components corresponding to the look up table of FIG. 7A. The optical schematic shows the components as described herein used to determine the look up table for the UF pulsed laser, for example with reference to FIG. 4A. The laser beam can be transmitted through zoom optics to a limiting aperture to determine beam size. The limited beam proceeds to relay lenses and then to the optical z-telescope lens. The distance ZL is varied, and ZL can be programmed into optical modeling software as described herein. The beam is then transmitted to X and Y galvos to deflect the beam passed to the objective lenses (hereinafter "OBJ"). The objective lens focuses the laser beam toward the optically transmissive structure, which may comprise a plate or lens as described herein, for example. The distance from the objective lens to the optically transmissive structure (hereinafter "CLopt") and be used to determine the location of the optical breakdown, and the thickness of the optically transmissive structure (hereinafter "WCL") can be used to determine the location of optical breakdown.

FIG. 7A2 shows input and output of the look up table as in FIGS. 7A and 7A1. The input parameters are the X, Y and Z locations of the optical breakdown within the mapped treatment volume, the distance from the objective lens to the anterior surface of the optically transmissive structure, and the thickness of the optically transmissive structure of the patient interface. The output of the look up table comprises the X mirror position for the ultrafast laser (hereinafter "Xm(UF)"), the Y mirror position for the ultrafast laser (hereinafter "Ym(UF)"), and the position of the z-telescope lens (hereinafter "ZL(UF)").

FIG. 7A3 shows structure of the look up table via an excerpt of the look up table as in FIGS. 7A and 7A1. The look up table comprises a header, a body and columns corresponding to the mapped coordinates of the system as described herein. Although a low resolution is shown the table may comprise a high resolution table readily constructed by a person of ordinary skill in the art based on the teachings described herein.

The header may comprise a description of the table and laser system components, for example. The header may comprise the input and output parameters such as the output parameters Xm(UF) in degrees, Ym(UF) in degrees, ZL(UF) in mm, for the UF laser wavelength, and the header may comprise the input parameters such as the X, Y and Z coordinates of treatment in the eye in millimeters, the thickness of the optically transmissive structure CLth, and the position of the posterior surface of the optically transmissive structure CLopt, The header may comprise baseline expected locations and coordinate references of identifiable structures, such as reference locations of the origin of the coordinate reference system, the location of the cornea along the Z axis, the location of the limbus along the X-axis and the location of the limbus along the Y-axis. The mapped positions of the system components can be provided for each of these input locations, such as the X and Y mirror positions, Xm(UF), Ym(UF). Also included in the header are the z-telescope position ZL(UF), The ZED(UF) position as shown in the figures, the delta Z value (hereinafter "Dz") which may comprise a correction, and the Strehl ratio which can be used to determine the quality of beam focus and adjustment to the location of optical breakdown. One of the purposes of the header is to provide a sample of key points within the look up table. These key points may be compared to multiple executions of the model to generate the look up table. These key points can be used as watch points to gain an overview of the performance of the model run and can be used to determine the health or veracity of the look up table.

The delta Z can be determined in one or more of many ways, and can be determined based on the computer modeling as described herein. Alternatively or in combination, the value of Delta Z can be determine based on measurements of a constructed system as described herein, for example.

The body of the look up table may contain the values of the look up table. The values can be determined based on optical modeling as described herein. Each value of the table may comprise Step comprising a location of the record of the table, ZL, X, Y and Z coordinate, CLopt, CLth, Xm(UF), Ym (UF), ZL (UF), a value Dz at the location, the Strehl ratio, and a flag. The flag may be indicative of the stability of the model run in generating the look up table. Dz for example can be used as a metric as to whether the model adequately converges to a solution. In general, the generic look up table is automatically generated using an optical program using a merit function and a set of variables to reduce a custom designed error function. Dz is then calculated by the program using a different mode or definition of best focus. Ideally these would arrive at the same solution but as the beam becomes more aberrated as a function of position these two methods may differ as expressed in Dz. The flag can then be toggled to a set the value of Dz. For example, the flag may equal 1 when the Dz is with 10 um or 0.010 in the table of FIG. 7A3 and set to 0 when outside this value. In this way, the automatic reading by system software of the look up table can using this value as an indication of the acceptable cut zone.

Figure 7B:
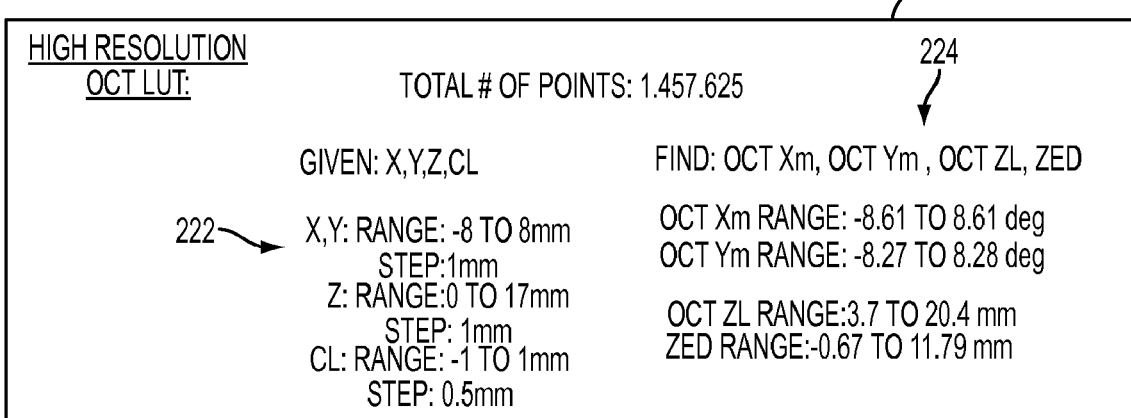
FIG. 7B shows a look up table summary for an optical coherence tomography system, in accordance with many embodiments.

FIG. 7B shows a look up table 220 for an optical coherence tomography system. The look up table 220 may comprise a plurality of discrete input values 222 over a range, for example four values such as X, Y, Z of patient coordinate reference system and distance CL of the lower surface of the lens, and a plurality of discrete output values 224. The X and Y values of the eye can range from −8 to 8 mm, in 0.25 mm increments, for example. The Z value can range from 0 to 17 mm in 0.25 mm increments, for example. The CL value can range from −1 to 1 mm in 0.5 mm increments, for example. These four dimensional input values can be input into processor system and an output machine value provide for each combined input. The output values 224 of the look up table can be provided as Xm, Ym and ZL for each combined input value combination. The output of Xm and Ym can each be within a range from −8.59 degrees to 8.59 degrees of the corresponding galvanometer mirror. The output value for ZL can be within a range from 3.7 to 20.7 mm, for example. The output value of ZED of the OCT arm can be provided based on the teaching described herein. The output value ZED can be configured to provide adjustment to the OCT arm over the full range of motion of the z-telescope moving lens in order to provide coherence to the OCT system, for example. The total number of input of the LUT can be about 1,457,625 for each input comprising (X, Y, Z, CL) and each output comprising (Xm, Ym, ZL, ZED), for example. The output and input mapping process can be switched. The OCT ranging system is a measurement device used to find intended surfaces. In this way, the values of OCT Xm, OCT Ym, OCT Zl, and ZED are determined once the targeted surface is located. These are used as input values to generate output values for X, Y, and Z for the location of the intended targeted structure. These output values for X, Y, Z along with measured values for CL can then be used as input to the UF LUT 212 to determine the output UF Xm, UF Ym, UF ZL for placing cuts.

FIG. 7B1 shows an optical schematic of the components corresponding to the look up table of FIG. 7B. The optical schematic shows the components as described herein used to determine the look up table for the OCT system, for example with reference to FIG. 4A. The measurement beam can be transmitted to a reference arm with a beam splitter. The portion of the beam transmitted through the beam splitter is transmitted to the optical z-telescope lens. The distance ZL is varied, and ZL can be programmed into optical modeling software as described herein. The beam is then transmitted to X and Y galvos to deflect the beam passed to the objective lenses OBJ. The objective lens focuses the laser beam toward the optically transmissive structure, which may comprise a plate or lens as described herein, for example. The distance from the objective lens to the optically transmissive structure CLopt can be used to determine the location of the measurement location corresponding to optical breakdown, and the thickness of the optically transmissive structure WCL can be used similarly.

The OCT measurement may comprise an optical path length hereinafter (OPL) that can be referenced from one or more of many locations of the OCT measurement system, such as the output aperture from the light source of the OCT measurement beam.

FIG. 7B2 shows input and output of the look up table as in FIGS. 7B and 7B1. The input parameters are the Xm, Ym and ZL locations of the OCT measurement beam within the mapped treatment volume, the distance from the objective lens to the anterior surface of the optically transmissive structure CLopt, the thickness of the optically transmissive structure of the patient interface, CLth, and the location of measurement arm ZED(OCT). The output of the look up table comprises the X position for the OCT measurement beam (hereinafter "X(OCT)"), the Y position for the OCT measurement beam (hereinafter "Y(OCT)"), and the Z position (hereinafter "Z(OCT)") for the OCT measurement beam.

FIG. 7B3 shows structure of the look up table as in FIGS. 7B and 7B1. The look up table comprises a header, a body and columns corresponding to the mapped coordinates of the system as described herein. Although a low resolution is shown the table may comprise a high resolution table readily constructed by a person of ordinary skill in the art based on the teachings described herein.

The header may comprise a description of the table and laser system components, for example. The header may comprise parameters such as Xm(OCT) in degrees, Ym(OCT) in degrees, ZL(OCT) in mm, for the OCT laser wavelength, and the header may comprise the parameters such as the X, Y and Z coordinates of the measurement beam in the eye in millimeters, the thickness of the optically transmissive structure CLth, and the position of the posterior surface of the optically transmissive structure CLopt from the posterior surface of the objective lens. One of the purposes of the header is to provide a sample of key points within the look up table. These key points may be compared to multiple executions of the model to generate the look up table. These key points can be used as watch points to gain an overview of the performance of the model run and can be used to determine the health or veracity of the look up table.

The header may comprise baseline locations and coordinate references of identifiable structures, such as reference locations of the origin of the coordinate reference system, the location of the cornea along the Z axis, the location of the limbus along the X-axis and the location of the limbus along the Y-axis. The mapped positions of the system components can be provided for each of these locations, such as the X and Y mirror positions, Xm(OCT), Ym(OCT). Also included in the header are the z-telescope position ZL(OCT), the ZED(OCT) position as shown in the figures, the delta Z value (hereinafter "Dz") which may comprise a correction, and the Strehl ratio which can be used to determine the quality of measurement beam focus.

The OCT delta Z can be determined in one or more of many ways, and can be determined based on the computer modeling as described herein. Alternatively or in combination, the value of Delta Z can be determine based on measurements of a constructed system as described herein, for example. The value of the OCT delta Z may comprise a map from the measured OCT location to the optical breakdown location, for example.

The body of the look up table may contain the values of the look up table. The values can be determined based on optical modeling as described herein. Each value of the table may comprise Step comprising a location of the record of the table, ZL, X, Y and Z coordinate, CLopt, CLth, Xm(OCT), Ym (OCT), ZL (OCT), a value Dz at the location, the Strehl ratio, and a flag. The flag may be indicative of the stability of the model run in generating the look up table. Dz for example can be used as a metric as to whether the model adequately converges to a solution. In general, the generic look up table is automatically generated using an optical program using a merit function and a set of variables to reduce a custom designed error function. Dz is then calculated by the program using a different mode or definition of best focus. Ideally these would arrive at the same solution but as the beam becomes more aberrated as a function of position these two methods may differ as expressed in Dz. A flag can then be toggled to a set the value of Dz. For example, the flag may equal 1 when the Dz is with 10 um or 0.010 in the table of FIG. 7A3 and set to 0 when outside this value. In this way, the automatic reading by system software of the look up table can using this value as an indication of the acceptable cut zone.

Figure 7C:
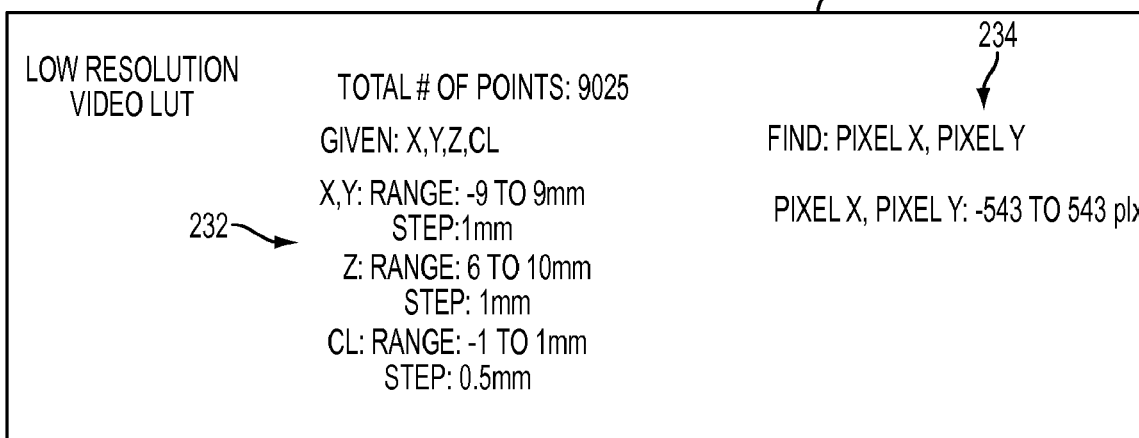
FIG. 7C shows a look up table summary for a video camera, in accordance with many embodiments.

FIG. 7C shows a look up table 230 for a video camera. The look up table 230 may comprise a plurality of discrete input values 232 over a range, for example four values such as X, Y, Z of patient coordinate reference system and distance CL of the lower surface of the lens, and a plurality of discrete output values 234. The X and Y values of the eye can range from −9 to 9 mm, in 1 mm increments, for example. The Z value can range from 6 to 10 mm in 1 mm increments, for example. The CL value can range from −1 to 1 mm in 0.5 mm increments, for example. These four dimensional input values can be input into processor system and an output machine value provide for each combined input. The output values 234 of the look up table can be provided as Pixel X, Pixel Y, and the range of Pixel X and Pixel Y can each be from about −543 pixels to about 543 pixels. The output and input mapping process can be switched. The video system is a measurement device used to find intended surfaces. The video system is also used as target aid for the user to place cuts. In these ways, the values of Pixel X and Pixel Y are determined using the video image. The values of Pixel X and Pixel Y along with either assumptions or measurements made for Z and CL are used as input values to generate output values for X, Y, and Z for the location of the intended targeted structure. The output values for X, Y, Z along with measured values for CL can then be used as input to the UF LUT 212 to determine the output UF Xm, UF Ym, UF ZL for placing cuts.

The look up table 210, the look up table 220, the look up table 230 can be combined in one or more of many ways to treat the patient. Further, inverse look up tables can be determined so as to map from machine parameters to parameter of the eye. In many embodiments, the OCT look up table 220 is used to image the eye and patient interface with OCT at a series of discrete OCT locations based on commands to the laser system to in order to scan a target region of the eye. The scan data for the locations of the eye can then be input into the look up table 210 for treatment table generation and planning, and the patient treated with the output 214 from treatment table 210.

The data for each look up table can be interpolated, for example with known interpolation methods. For example, the interpolation may comprise linear interpolation based on values of closest neighbors provided to the look up table. The look up table can be extrapolated to extend the ranges.

The look up tables as described herein are provided in accordance with examples, and a person of ordinary skill in the art will recognize many alternatives and variations.

FIG. 7C1 shows an optical schematic of the components corresponding to the look up table of FIG. 7C. The optical system forms an image on the camera array comprising x pixels at x pixel locations (hereinafter "Pix X") and y pixels at y pixel locations (hereinafter Pix Y). The image is formed with a plurality of fixed focus lenses. The image beam passes through an aperture stop located between the fixed focus lenses to arrive at the sensor array. A field stop is provided along with another fixed focus lens optically coupled to the objective lenses. The patient interface and distances are described herein.

FIG. 7C2 shows input and output of the look up table as in FIGS. 7C and 7C1. The input comprises the measured Pix X and Pix Y coordinate references of the CCD array. The input may also comprise the Z focus location of the eye, and the CLopt and CLth parameters. The output comprises the X and Y coordinate references of the eye at the input Z depth.

FIG. 7C3 shows the structure of the look up table as in FIGS. 7C to 7C2. Although a low resolution table is shown, the high resolution table can readily be constructed by a person of ordinary skill in the art based on the teachings described herein. The structure of the table comprises a header and a body comprising columns of the table.

The header may comprise the input and output parameters for the wavelength of the video imaging system. The parameters may comprise the X, Y and Z locations of the imaging system within the eye and the parameters may comprise the corresponding X pixels (Pix X) and Y pixels (Pix Y). The header may comprise coordinate reference locations corresponding to tissue structures of the eye, such as the iris or the limbus, for example. The coordinate reference locations may comprise a location within the eye along the axis of the system at coordinates X=0, Y=0 and Z=8 mm, for example. The corresponding mapped X and Y pixel coordinates for X=5 mm and Y=5 mm can be provided at pixel coordinate locations of approximately 303 pixels, respectively, for example. One of the purposes of the header is to provide a sample of key points within the look up table. These key points may be compared to multiple executions of the model to generate the look up table. These key points can be used as watch points to gain an overview of the performance of the model run and can be used to determine the health or veracity of the look up table.

The body of the look up table may comprise the Pixel X, Pixel Y, Z, CLopt, Clth, input parameters. The output of the look up table may comprise the output X and Y locations for each input record, for example. The corresponding diameter of the spot can be provided at each location in pixels, and a logic flag can be provided for each location. The logic flag may comprise one or more of many logic signals, and may correspond to whether the image of tissue is to be provided at the location, or whether the focus of the treatment beam at the mapped X Pix and Y Pix location is suitable for treatment, for example.

Figure 8A:
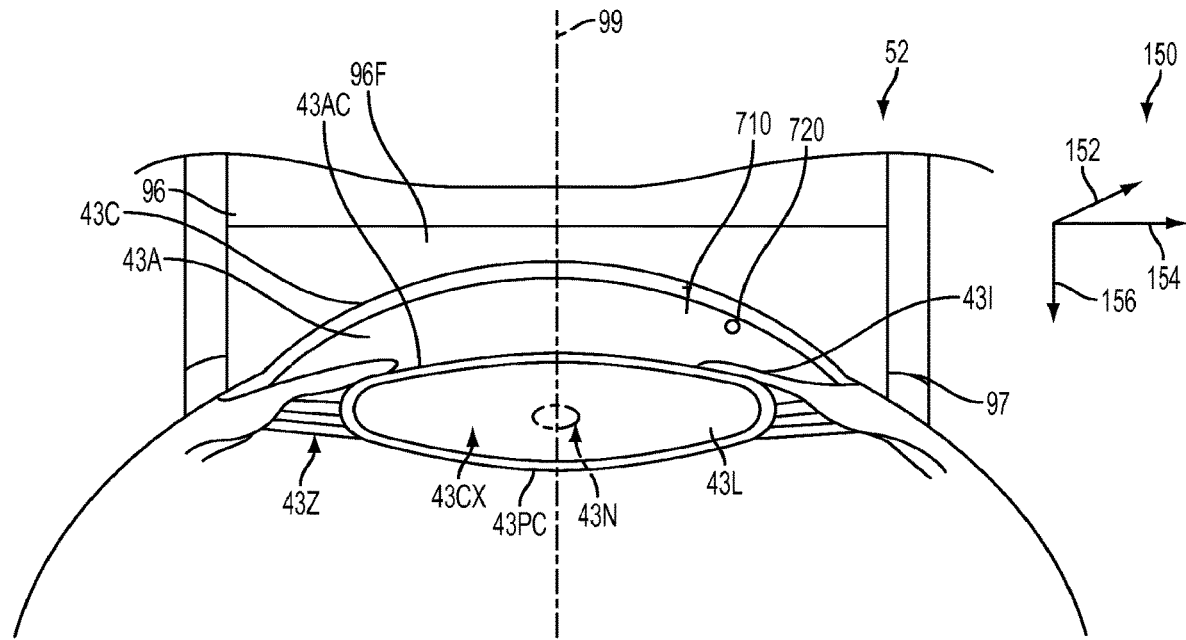
FIGS. 8A and 8B show side and front views of structures of the eye that have one or more markings for calibration, in accordance with many embodiments.
Figure 8B:
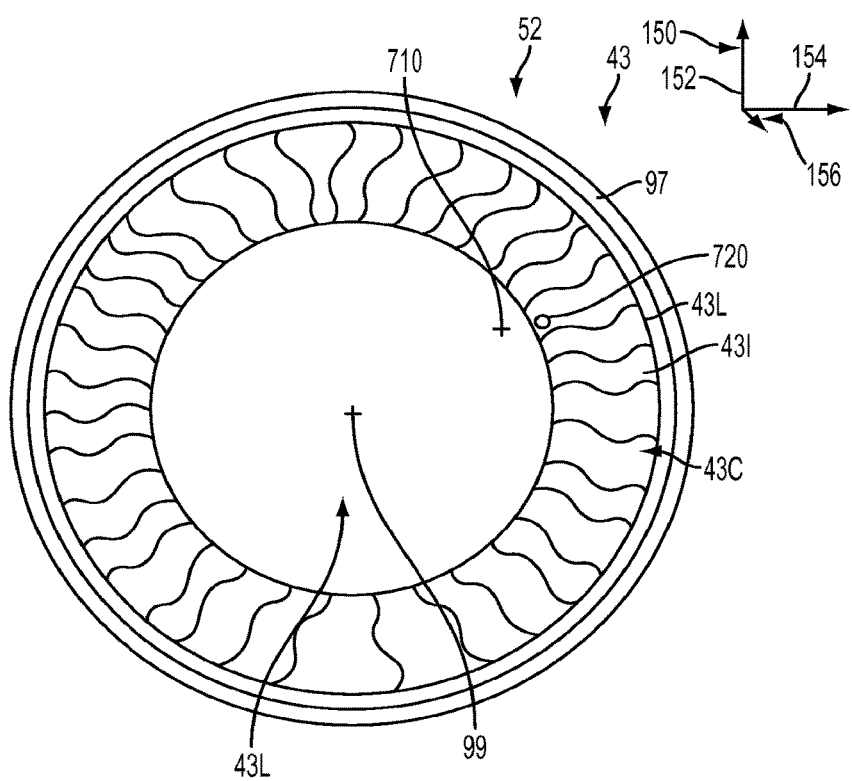

FIGS. 8A and 8B show marking of an eye in order to calibrate the eye in accordance with many embodiments. FIG. 8A shows a side view of the eye and FIG. 8B shows a front view of the eye. The eye is marked with reference to eye coordinate reference system 150 based on the machine coordinate reference system as described herein. A mark 720 is made on the eye with a laser beam. The eye is marked based on a targeted location 710. In many embodiments, the targeted location 710 differs from the marked location 720. The marked location 720 can be measured with the tomography system as described herein and compared to the targeted location 710. The response to the difference between the targeted location 710 and the marked location 720 the laser system can be calibrated. The laser can be calibrated with in situ NC2 calibration as described herein.

In many embodiments, the calibration of the mark with reference to the targeted location 710 comprises a three dimensional calibration. The eye coordinate reference system 150 comprises of three dimensional coordinate system and the difference between the targeted location 710 and the marked location 720 comprises of three dimensional difference. In many embodiments, a second targeted location can be identified and determined in a second marked location can be identified and measured with respect to the second location. The second location may comprise an updated, improved location based on the first measured targeted location and the first measured mark.

The targeted location may comprise of plurality of targeted locations and can be located in one or more of many places as described herein. For example, the targeted location may comprise a location of the optically transmissive structure such as the lens 43L. The targeted location may comprise a location of the fluid 96F. The fluid 96F may comprise a saline, a visco-elastic substance, or other viscous fluid as described herein. In many embodiments, the visco-elastic fluid can be marked and the visco-elastic fluid provides support so as to inhibit movement between marking and measurement as described herein. The targeted location 710 may comprise of location of the cornea 43C or may comprise a location of the interior chamber 43A. For example, the targeted location may comprise a location of the lens 43L. For example, a posterior capsule of the lens 43PC, a cortex of the lens 43CX, or an anterior capsule of the lens 43AC as described herein, for example. In many embodiments of plurality of locations are targeted and a plurality of marks are measured so as to provide three dimensional calibration over a range of locations in order to ensure that the laser system is accurately calibrated on the eye beam treated prior to initiating the treatment pulses. The treatment pulses may comprise incision pulses, for example, so as to incise an interior capsule of the lens 43L. The treatment pulses may comprise incision pulses so as to cut and reset tissue of the lens 43L, for example, so as to cut the lens tissue such as the cortex and the nucleus with a three dimensional profile that effectively provides cubes of the lens or other structures of the lens that can be readily removed. And in many embodiments, the plurality of targeted locations are defined so as to define a volume and a portion of the volume comprises the treatment of the eye. For example, in many embodiments, the calibration pulses may comprise targeted locations of the cornea or the anterior chamber or the viscous fluid 96F for example, and these anterior locations can be combined with posterior locations, for example, a portion of the lens so as to define a volume. And in many embodiments, the targeted location comprises a single pulse at a single location so as to define a mark with a single pulse. Alternatively or in combination, the marks may be defined with a plurality of laser beam pulses at a targeted location, for example.

The targeted location of the eye for treatment may comprise the cornea 43C. The cornea 43C can be treated in one or more of many ways, for example with an incision so as to provide a refractive correction of the cornea 43C and the incisions of the cornea may comprise access incisions, for example incisions to provide access for a phacoeemulsification probe, for example. And the incisions can be performed with a plurality of laser beam pulses. The calibration is described herein is particularly well-suited for incision of the posterior lens capsule and can provide improved accuracy so as to inhibit damage to structure posterior to the posterior capsule.

Figure 8C:
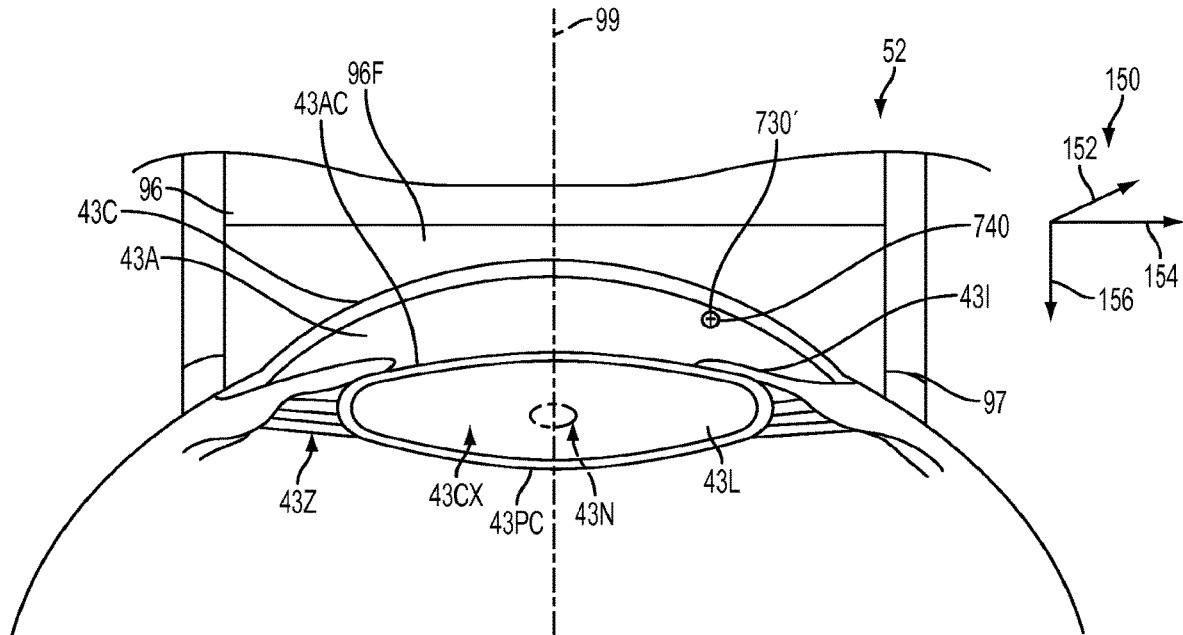
FIGS. 8C and 8D show side and front views of structures of the eye that have one or more markings for calibration corresponding to one or more target locations, in accordance with many embodiments.
Figure 8D:
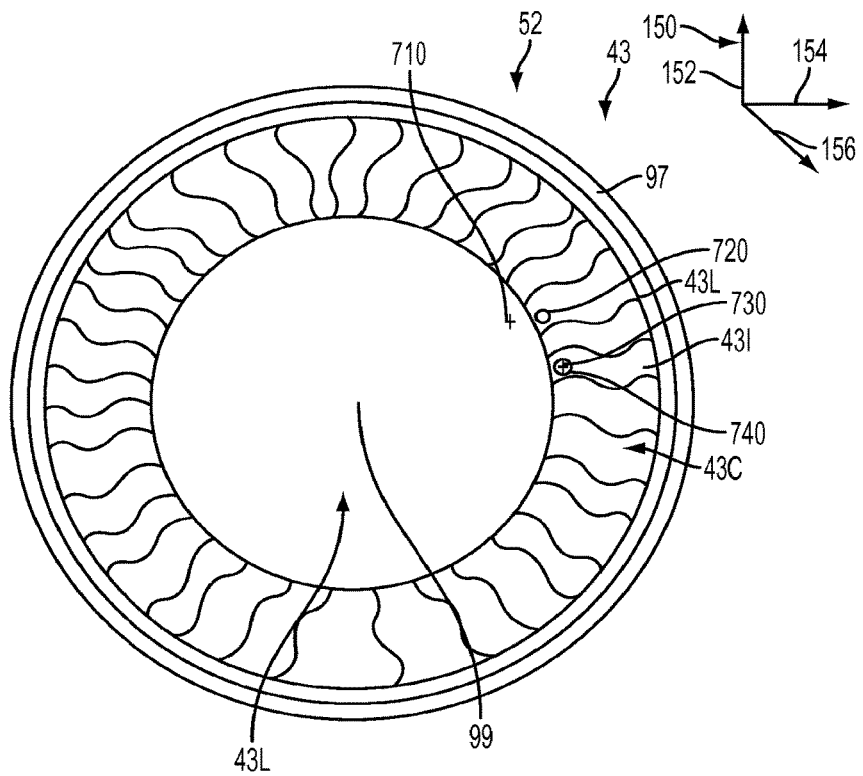

FIGS. 8C and 8D show a targeted location 730 and a mark 740 obtained with calibration as described herein. The targeted location 730 coincides with the mark 740. The mark 710 may comprise one or more marks such as a plurality of marks as described herein. The targeted location 710 may comprise one or more targeted locations such as a plurality of targeted locations as described herein. The mark 720 may comprise one or more marks such as a plurality of marks as described herein.

The targeted location subsequent to NC2 calibration 730 may comprise one or more targeted locations, for example a plurality of locations. The one or more mark 740 obtained subsequent to calibration may comprise one or more marks, for example a plurality of marks as described herein.

Figure 9A:
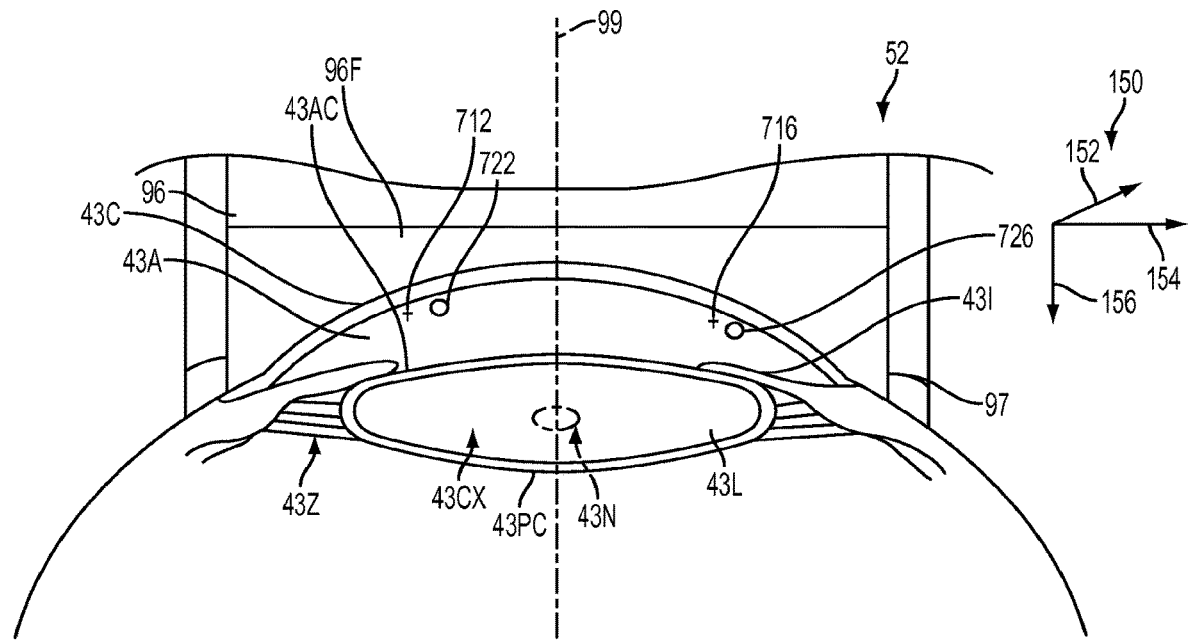
FIGS. 9A and 9B show side and front views of structures of the eye that have a plurality of markings for calibration, in accordance with many embodiments.
Figure 9B:
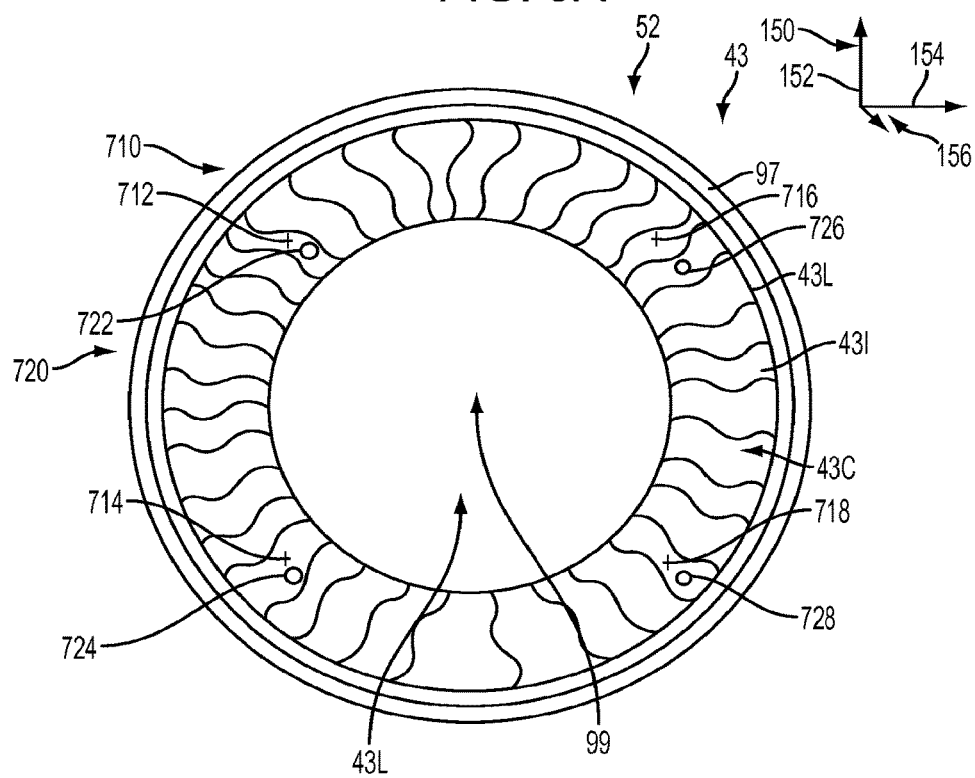
Figure 9C:
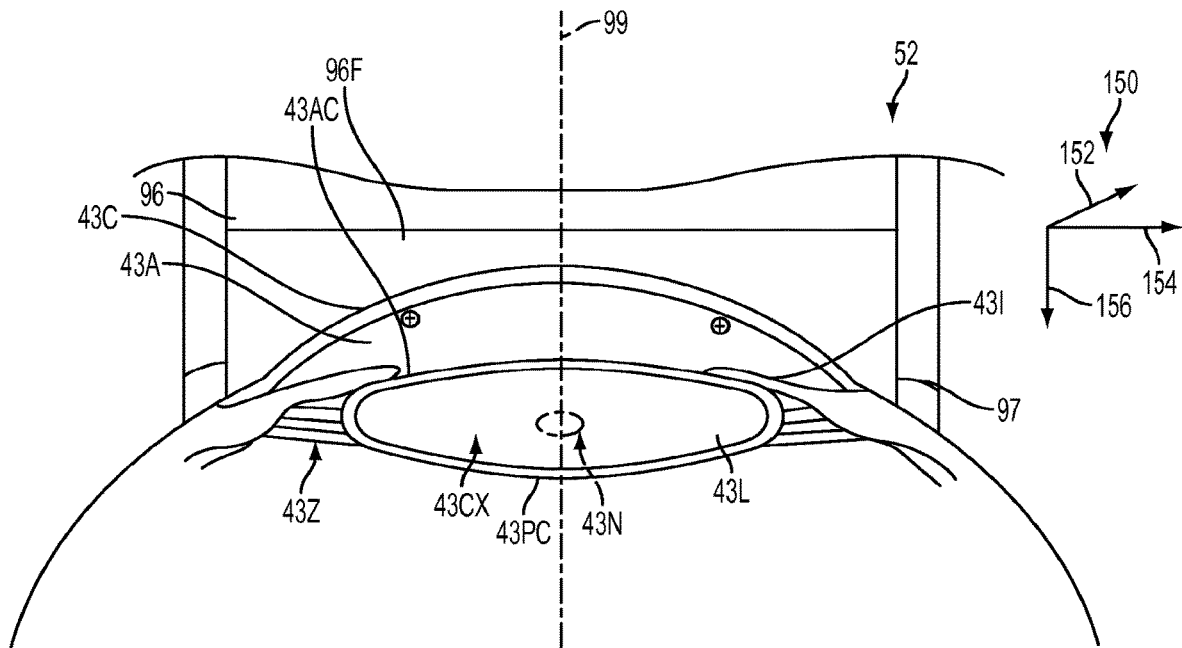
FIGS. 9C and 9D show side and front views of structures of the eye that have a plurality of markings for calibration corresponding to a plurality of target locations, in accordance with many embodiments.
Figure 9D:
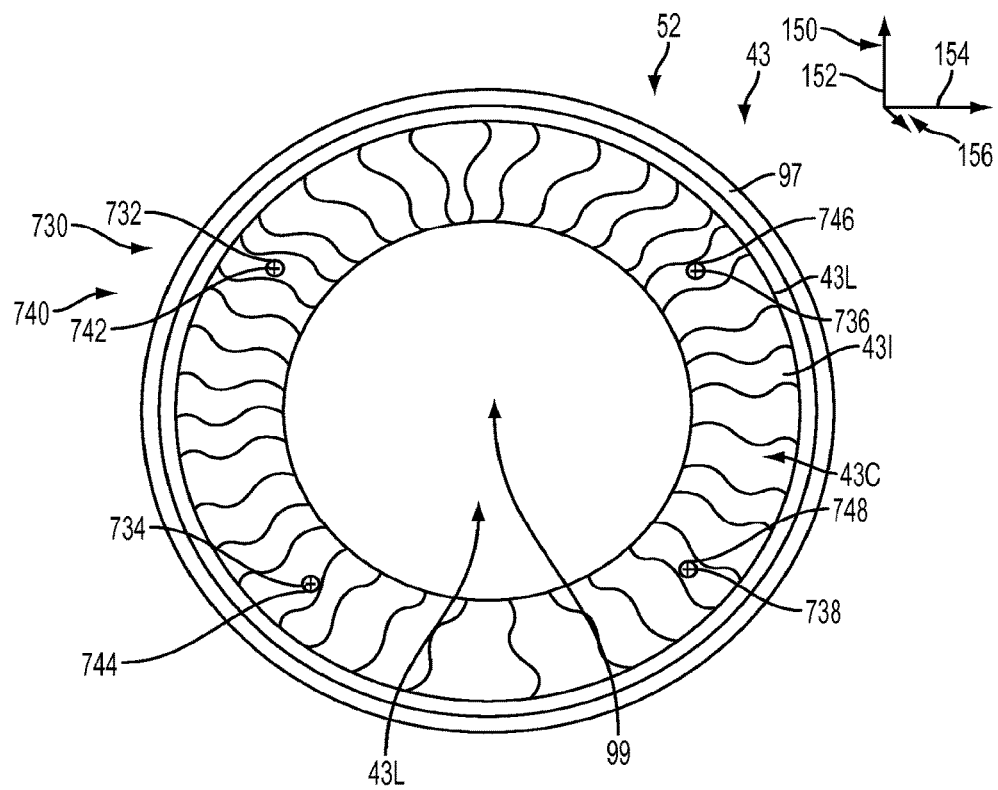

FIGS. 9A and 9B show a plurality of targeted locations on the eye and a plurality of corresponding on the eye for each of the plurality of targeted locations. The plurality of targeted locations may comprise a first targeted location 712, a second targeted location 714, a third targeted location 716, and a fourth targeted location 718. A person of ordinary skill in the art will recognize that one or more of many targeted locations can be used as described herein in one or more of many patterns. For example, square, circular, or other patterns can be used on the to provide the targeted location for the calibration and tracking as described herein. A plurality of marked locations corresponding to the plurality of targeted locations can be identified and measured as described herein based on the difference between the targeted locations and the measured locations of the marks, the laser system can be calibrated with NC2 calibration as described herein. As shown in FIGS. 9A and 9B, the plurality of marks comprises a first mark 722, a second mark 724, a third mark 726, and a fourth mark 728 in which each mark can be compared to each targeted location and the difference in the measured location of each mark compared to the measured location of each targeted location so as to provide three dimensional calibration over treatment volume as described herein. FIGS. 9C and 9D show respectively side and front views of the eye subsequent to NC2 calibration as described herein. The plurality of subsequent pulses can be performed in order to determine the accuracy of the calibration with respect to FIGS. 9A and 9B. For example, as shown in FIGS. 9C and 9D, the plurality of marks correspond quite closely to the plurality of targeted locations. The acceptable tolerance can be defined in one or more of many ways as described herein and can depend upon the tissue being treated with the laser beam. In many embodiments, the laser beam calibration can be accurate to within about 10 microns, for example, and in many embodiments, to within about 100 microns for example. The plurality of targeted locations comprises a first targeted location 732, a second targeted 734, a third targeted location 736, and a fourth targeted location 738. A first plurality of marks comprises a first mark 742, a second mark 744, a third mark 746, and a fourth mark 748. The plurality of marks corresponds closely to the plurality targeted locations and confirms the accuracy of the calibration.

The plurality of targeted locations can be defined in one or more of many ways. For example, the plurality of targeted locations subsequent to NC2 calibration as described herein, may comprise the original targeted locations. For example, the plurality of targeted locations 710 comprising first targeted location 712, second targeted location 714, third targeted location 716, and fourth targeted location 718, may comprise the targeted location subsequent to calibration, for example first targeted location 732, second targeted location 734, third targeted location 736, and fourth targeted location 738. In many embodiments, the marks subsequent to NC2 calibration can be observed and measured to shift in relation to the marks prior to calibration of the laser system.

Figure 10A:
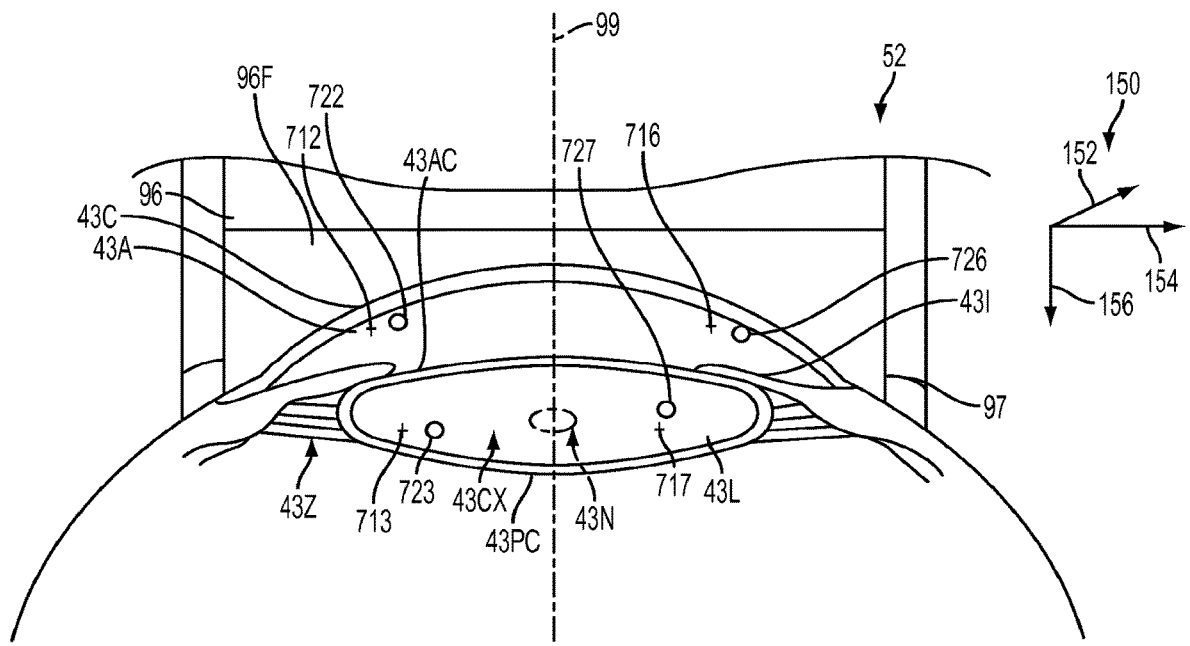
FIGS. 10A and 10B show side and front views of structures of the eye that have a plurality of markings that define a calibration volume, in accordance with many embodiments.
Figure 10B:
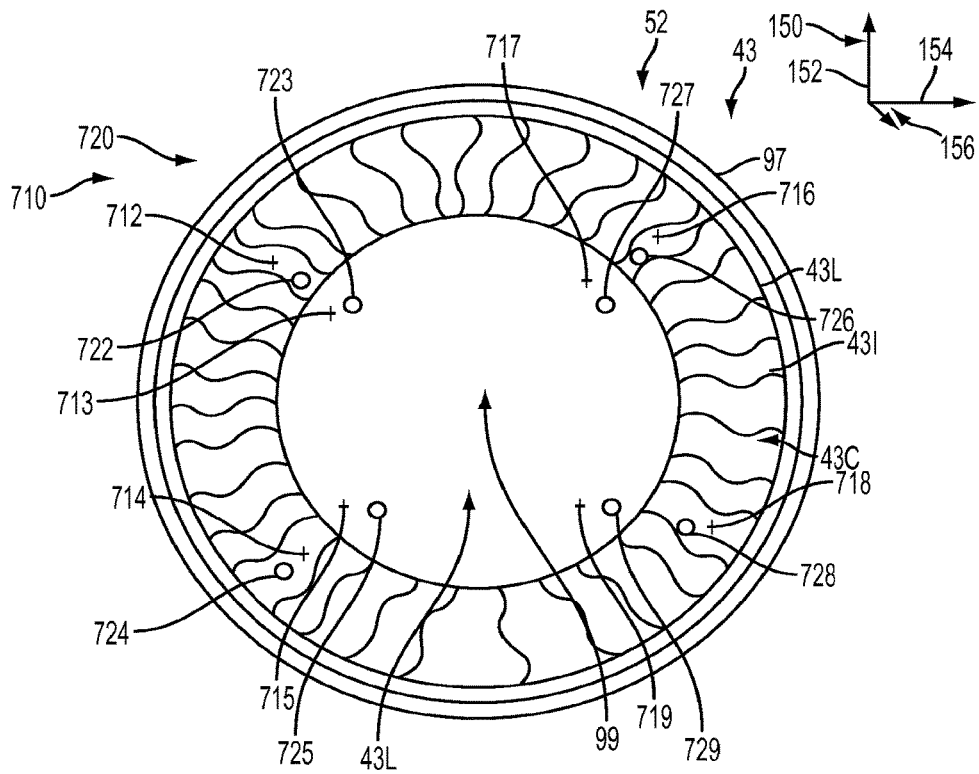

FIGS. 10A and 10B show NC2 calibration of an eye at a plurality of depth so as to define a calibration volume in accordance with embodiments. The plurality of targeted locations may comprise first targeted locations of the first axial depth along axis 99 and the second plurality of locations along a second location of axis 99 so as to define a volume. A calibration volume may comprise one or more locations of the treatment so as to ensure the accuracy of the treatment in alignment of the tomography apparatus with the laser beam. The plurality of anterior targeted locations and the plurality posterior targeted locations and define the volume in one or more of many ways is described herein.

The plurality of anterior targeted locations comprises first anterior targeted location 712, second anterior targeted location 714, third anterior targeted location 716, fourth anterior targeted location 718. The plurality of posterior targeted locations comprises of first targeted location 713, a second targeted location 715, a third targeted location 717, and a fourth targeted location 719. The plurality of anterior marks comprises a first anterior mark 722, a second anterior mark 724, a third anterior mark 726, and a fourth anterior mark 728. The plurality of posterior marks comprises a first mark 723, a second mark 725, a third mark 727, and a fourth mark 729.

The differences between the targeted locations in the marks can be measured to determine the accuracy of the laser system and to calibrate the laser system as described herein. For example, each of the anterior marks can be compared to each of the anterior targeted locations and each of the posterior marks can be compared to each of the posterior targeted locations and the system calibrated in many embodiments the calibration comprises a calibration volume and the laser system comprises mapping coordinate references that can be adjusted as described herein so as to provide improved calibration. For example, the look-up table as described herein can be adjusted. Alternative combination calibration coefficients corresponding to the treatment volume can be adjusted.

The calibration can be tested based on the adjustments to the calibration as described herein and additional pulses of the laser beam can be used to form additional marks on the cornea. For example, the laser beam can be pulsed at similar or the same targeted locations and the motion of the laser beam marks can be observed and measured as described herein. Subsequent to verification of the accuracy of the calibration, the patient can be treated.

In many embodiments, the laser pulses can be measured in real time and compared with the targeted locations with the tomography system as described herein.

Figure 11A:
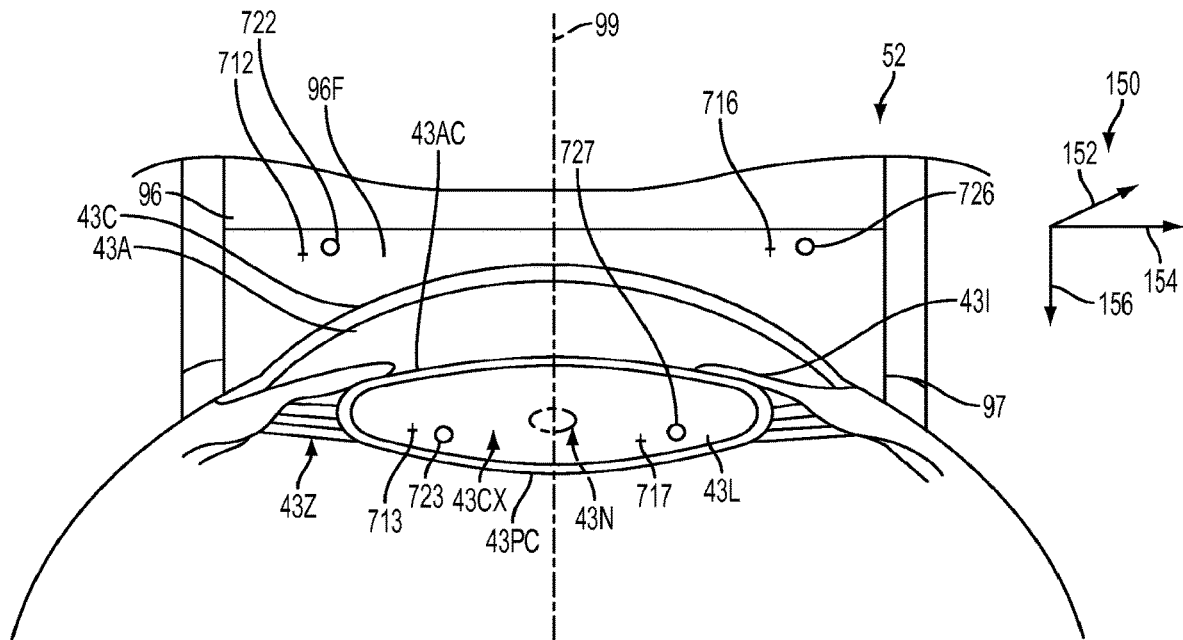
FIGS. 11A and 11B show side and front views of structures of the eye that have a plurality of markings in the viscous fluid in the eye, in accordance with many embodiments.
Figure 11B:
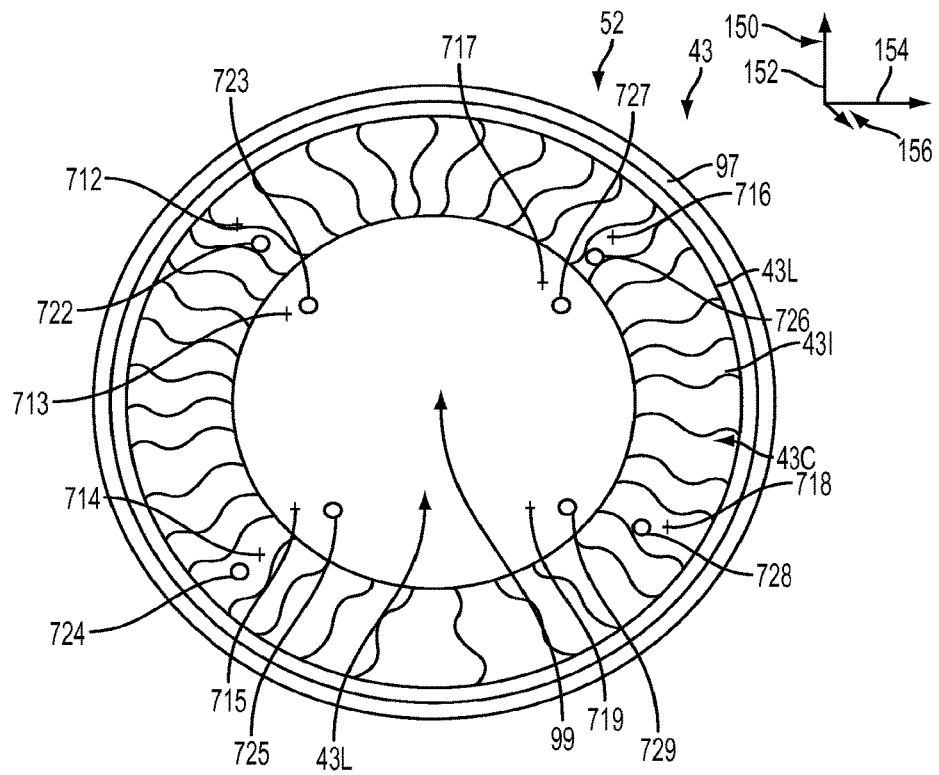

FIGS. 11A and 11B show targeted locations for calibration in the viscous fluid in the eye as described herein. In many embodiments, the anterior location may comprise locations of the viscous fluid 96F as described herein and the locations may comprise locations of a plurality of structures as described herein such as the visco-elastic fluid, the cornea, the anterior chamber, and the lens, for example. Work in relation to embodiments also suggest that in some embodiments it may be appropriate to calibrate the system with pulses to the vitreous humor of the eye. For example, with pulses away from the posterior capsule of the lens and away from the protective outer structures of the vitreous humor in order to calibrate the system for example with a plurality of individual pulses approximately 1 millimeter beneath the posterior capsule, or example.

The plurality of anterior pulses comprises a first pulse 712, a second pulse 714, a third pulse 716, and a fourth pulse 718. The plurality of anterior targeted locations comprises a first anterior targeted location 712, a second anterior targeted location 714, a third anterior targeted location 716, and a fourth anterior targeted location 718. The plurality of posterior targeted locations comprises a first posterior targeted location 713, a second posterior targeted location 715, a third posterior targeted location 717, and a fourth posterior targeted location 719. The plurality of anterior marks comprises a first interior mark 722, a second interior mark 724, a third interior mark 726, and a fourth interior 728. The plurality of posterior marks corresponding to the plurality of posterior targeted locations comprises a first posterior mark 723, a second posterior mark 725, a third posterior mark 727, and a fourth posterior mark 729. The locations of each of the marks can be measured and compared with the targeted location and the calibration co-efficient suggested as described herein. Alternatively or in combination, a treatment table may be adjusted in accordance with embodiments so as to provide improved accuracy.

Figure 12A:
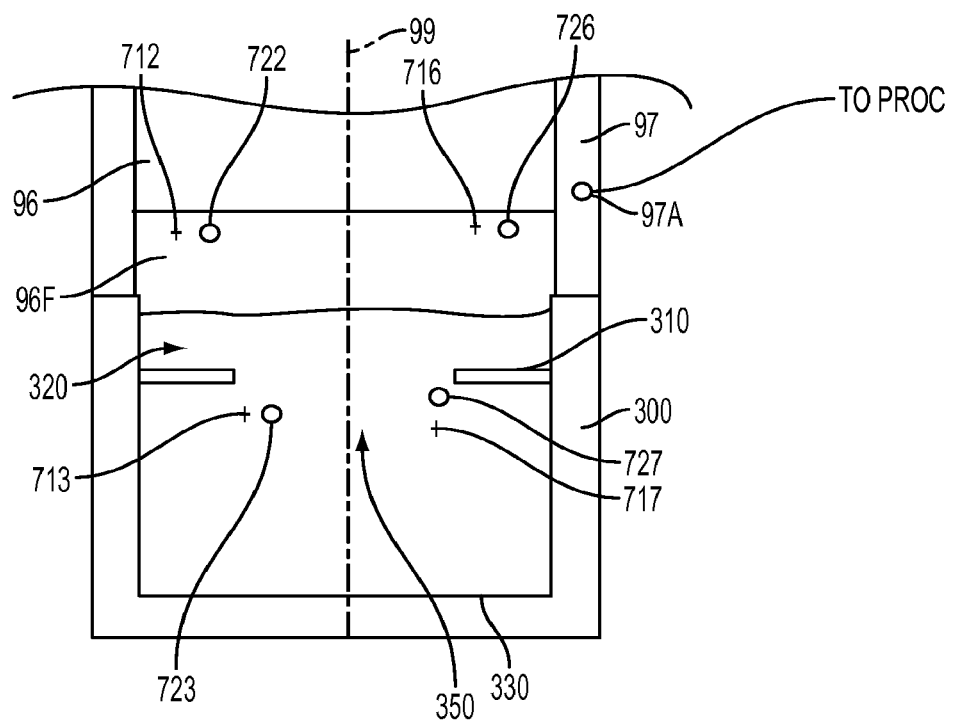
FIGS. 12A and 12B show side and front views of a calibration apparatus, in accordance with many embodiments.
Figure 12B:
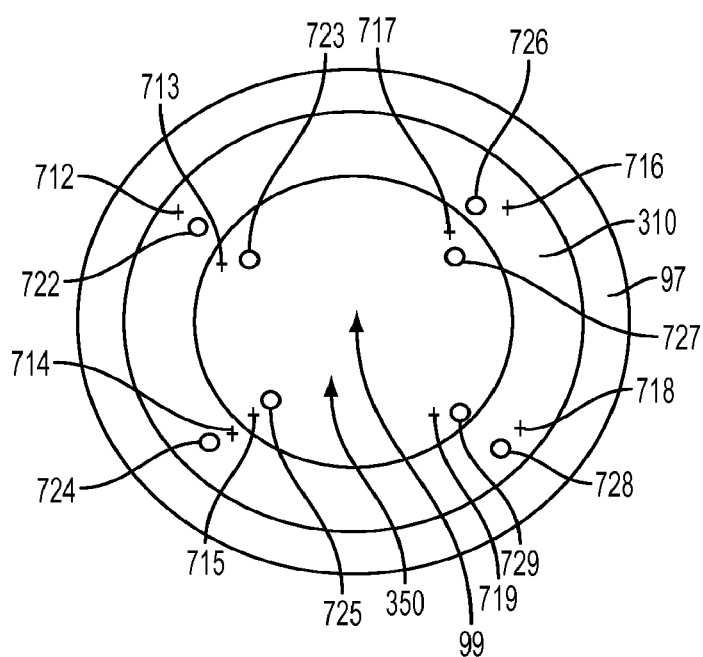

Subsequent to calibration of the laser system, additional marks can be provided as described herein for example, and the marks compared to the calibration co-efficient in the targeted locations as described herein. FIGS. 12A and 12B show a calibration apparatus in accordance with embodiment. The calibration apparatus 300 comprises structures similar to structures of an eye. For example, the calibration apparatus 300 comprises a container 350, the container 350 comprises of viscous substance similar viscous or solid substance that is optically transmissive similar to the structures of the eye. The material 320 may comprise of visco-elastic fluid, a gel or other optically transmissive structure and material, for example. The calibration apparatus 300 comprises an iris structure 310, the iris structure comprises components similar to an iris of an eye and can provide calibration with respect to a reference. In many embodiments the material 320 comprises a known index of refraction in order to calibrate the system, for example, the index for refraction may comprise of a viscous material having a known index of refraction or a gel having a known index of refraction, for example. Here, a structure or property is "similar" if it is within 10%, preferably within 5% and more preferably within about 1% of a typical measurement of that structure or property in an adult human eye.

The calibration structure 300 may connect to the patient interface as described herein and a fluid 96F can be provided above the calibration apparatus, for example. The fluid 96F may comprise visco-elastic fluid, for example. A plurality of anterior marks can be made on the calibration apparatus and a plurality of posterior marks can be made on the calibration apparatus. For example, the anterior marks can be made in the fluid 96F, for example, a first targeted location, and a second targeted location, and a plurality of targeted locations as described herein. A plurality of posterior marks can be made on the calibration apparatus as described here.

In many embodiments, the calibration apparatus comprises an acoustic transducer 97A. The acoustic transducer 97A can be provided to measure the energy required to provide optical breakdown and the laser system can be adjusted at a plurality of energy levels and swept and scanned throughout the calibration volume to determine the energy required for optical breakdown and the energy required for optical breakdown mapped across the targeted treatment volume and calibration volume, for example. In many embodiments, the treatment laser is adjusted to a volume substantially above the threshold energy in order to ensure that optical breakdown will occur at the targeted tissue. For example, a safety factor of a multiplier of 2× at least 1.5× and for example, 3× can be provided.

The calibration apparatus can be calibrated in manner and be used for calibration in a manner similarly to that described above with reference to the NC2 calibration of the eye as described herein. The calibration apparatus maybe used daily for example, or monthly, or for example, prior to the treatment of each patient, depending on the amount of accuracy required, for example.

The plurality of anterior locations comprises a first targeted location 712, a second targeted location 714, a third targeted location 716, and a fourth targeted location 718. The plurality of posterior targeted locations comprises a first targeted location 713, a second targeted location 715, a third targeted location 717, and a fourth targeted location 719. The plurality of anterior marks comprises a first anterior mark 722, a second anterior mark 724, a third anterior mark 726, and a fourth anterior 728. The plurality of posterior targeted locations and corresponding marks comprises a first posterior mark 723, a second posterior mark 725, a fourth posterior mark 727, and a fifth posterior mark 729.

The plurality of targeted locations can be compared to the corresponding marks and the calibration adjusted based on the marks of the calibration apparatus as described herein.

Subsequent to calibration with the calibration apparatus, the laser can be programmed to provide additional targeted locations and to provide the additional targeted locations and marks at the targeted locations to verify the calibration for example describe with reference to the NC2 calibration of the eye as described herein. When the accuracy of the treatment has been determined based on a suitable tolerance for the treatment, the calibration apparatus can be removed from the patient interface and the patient interface configured for surgery with the patient.

Figure 13A:
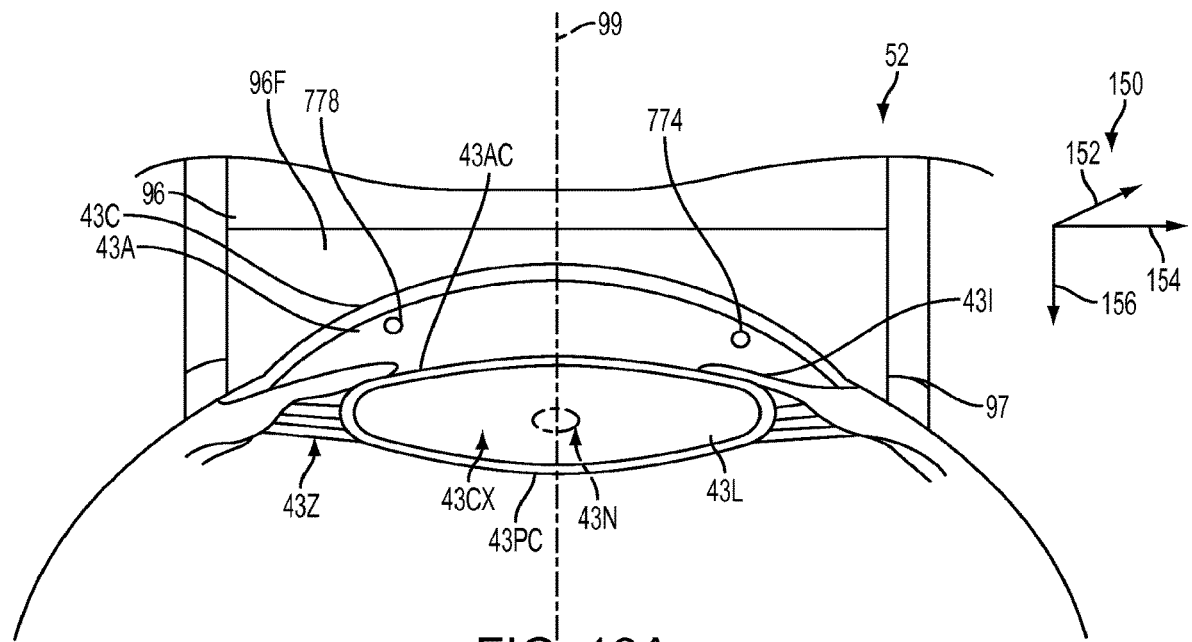
FIGS. 13A and 13B show side and front views of structures of the eye including markings for tracking, in accordance with many embodiments.
Figure 13B:
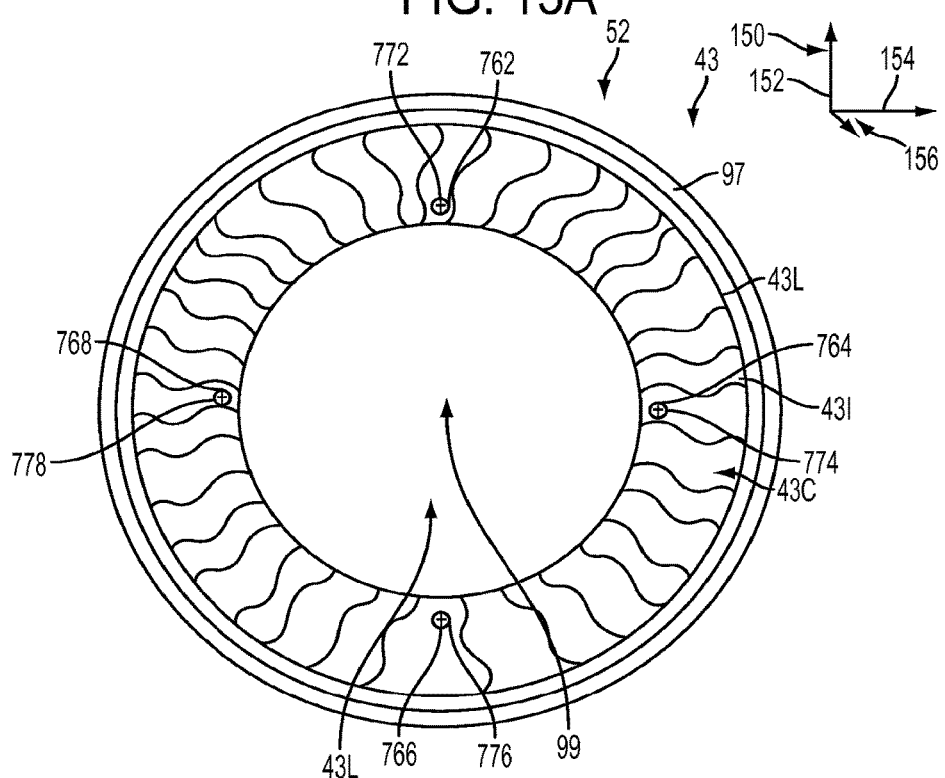

FIGS. 13A and 13B show eye tracking in accordance with embodiments. FIG. 13A shows a side view of the eye, FIG. 13B shows a front view of the eye. A plurality of marks 750 can be provided to track the eye during surgery in accordance with embodiments. The marks may comprise marks used for NC2 calibration, for example. Alternatively, the marks may comprise marks provided specifically for calibration. A person of ordinary skill in the art will recognize many variations in accordance with the embodiments described herein.

A plurality of marks for eye tracking may comprise a plurality of bubbles and with respect to eye tracking a first location is shown and a second location is shown of the mark in which the eye has moved. In many embodiments, the location of the mark is measured and determined at one or more locations for example, in the one or more locations can be stored in the processor memory and the tomography apparatus used to measure locations of the marks when the marks have moved, the laser system treatment can be adjusted accordingly and the adjustment may comprise one or more of six degrees of freedom for example.

In many embodiments, the eye comprises six degrees of freedom, for example three translational degrees of freedom and three rotational degrees of freedom. In many embodiments a plurality of marks can be used so as to define an eye coordinate reference system that can be movable and adjusted with respect to the eye coordinate reference system 150 and the treatment can be adjusted accordingly based on new coordinate references provided with the eye tracking system.

In many embodiments the eye tracker provides reference measurements that can be used to determine the position and orientation of the eye.

A first plurality of measured locations comprises a first measured location 762, a second measured location 764, a third measured location 766, and a fourth measured location 768. These measured locations correspond to a first position of the eye and a first orientation of the eye. These locations can be measured with the marks as described herein, when the eye comprises of first configuration. When the eye moves, and subsequent to eye movement, as shown in FIGS. 13A and 13B, the measured locations of the marks changes, and the marks comprise a second plurality of marked locations for example, a first measured mark location 770, a second marked of plurality of marked locations. The measured locations for a particular measurement and location of the eye comprises a marked location 770, a first marked location 772, a marked location 774, a marked location 776, and a marked location 778. Each of the marked locations can be compared to the plurality of measured locations and locations sorted in memory in the system.

The marked locations may comprise bubbles for example, or micro-bubbles from individual pulses of the laser beam and the pulses and the locations of the pulses can be measured. When the eye moves, the treatment can be adjusted in accordance with embodiments.

Figure 13C:
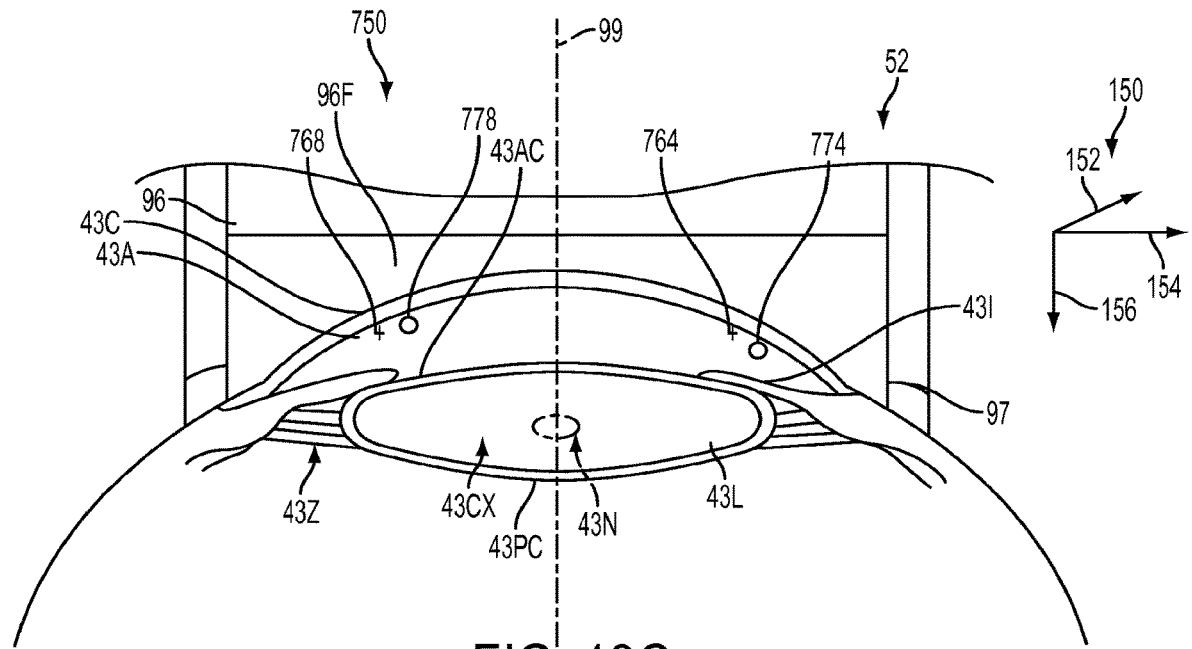
FIGS. 13C and 13D show side and front views of structures of the eye including markings that are tracked for movement, in accordance with many embodiments.
Figure 13D:
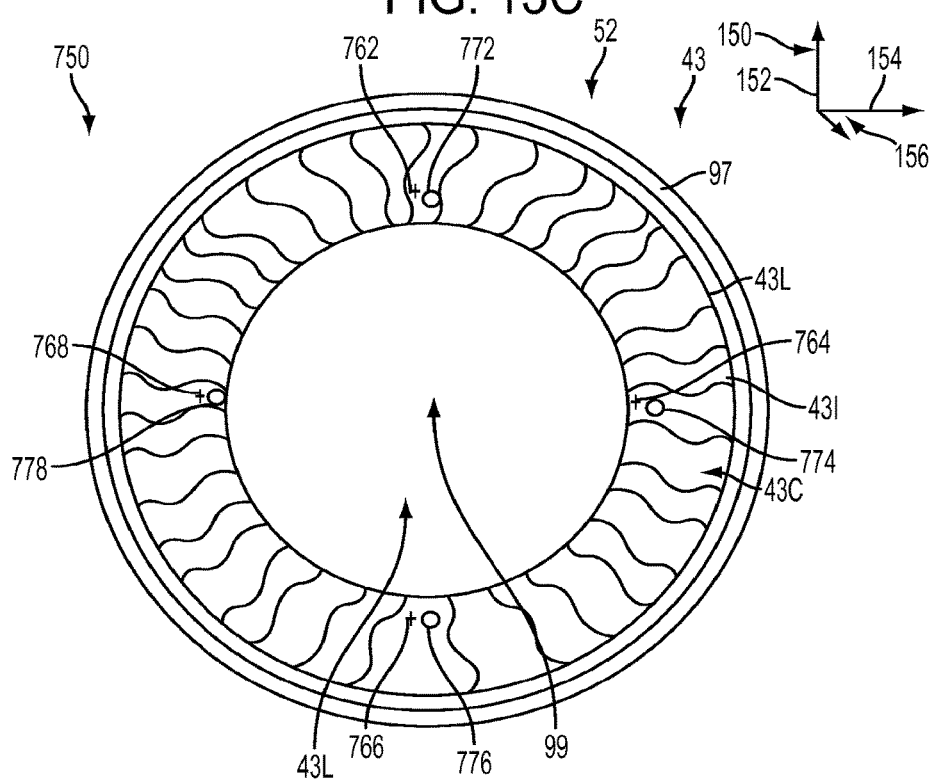
Figure 13E:
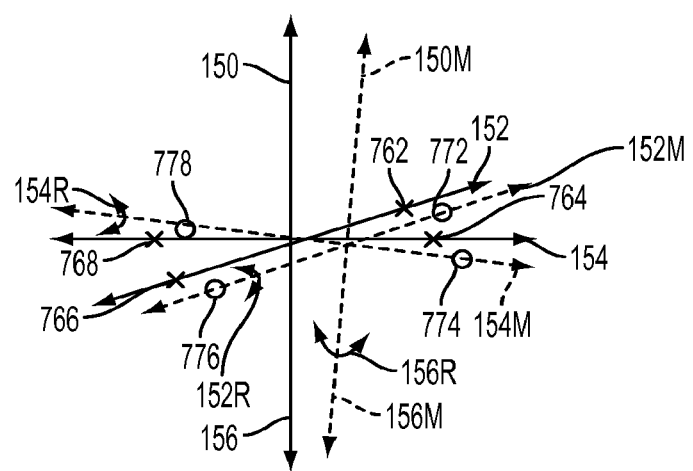
FIG. 13E shows an coordinate reference system, in accordance with many embodiments.

FIGS. 13A thru 13E show eye tracking in accordance with embodiments. FIGS. 13A and 13B show initial location of marks on the eye in accordance with embodiments. FIGS. 13C and 13D show movement of the marks on the eye in relation to reference location in accordance with embodiments. FIG. 13E shows movement of eye reference frame 150 in accordance with embodiments.

As shown in FIGS. 13A and 13B the eye can be marked with one or more marks such as a plurality of marks, for example. The plurality of marks may comprise a first mark 772, a second mark 774, a third mark 776 and a fourth mark 778. The one or more marks may comprise one or more of the many marks and many locations as described herein. The marks are placed with reference to eye coordinate reference system 150 and the marks may be calibrated in accordance with the embodiments described herein. The initial location of the marks may comprise reference location so as to allow eye tracking.

The eye tracking as described herein can be used to track movement of the eye. The movement of the eye may correspond to at least one degree of freedom, for example, as many as 6 degrees of freedom. In many embodiments, the eye comprises 3 rotational degrees of freedom and 3 translational degrees of freedom and the eye tracking embodiment as described herein allow tracking of the eye for both movement and translation in many embodiments. FIGS. 13C and 13D show movement of the plurality of marks and the initial locations as described herein.

The plurality of locations generally comprises one or more locations and each location corresponds to one or more marks. The plurality of locations may comprise a first location 762, a second location 764, a third location 766 and a fourth location 768. The first location 762 corresponds to the first mark 772, the second location 764 corresponds to the second mark 774, the third location 766 corresponds to the third mark 776, and the fourth location 768 corresponds to the fourth mark 778.

Referring now to FIGS. 13C and 13D movement of the marks with respect to the reference locations as shown in accordance with embodiments. The first mark 772 has moved in relation to the first reference location 762. The second mark 774 has moved in relation to the second reference location 764. The third mark 776 has moved in relation to the third reference location 766. And the fourth mark 778 has moved in relation to the fourth reference location 768.

A relation to embodiments indicates that the number of marks and reference locations can be related to the number of degrees of freedom for which eye tracking is provided. For example, a single mark can provide translational references with respect to an X-Y plane, for example, with relation to a pupil camera. Alternatively, 2 reference points can provide a rotation about an axis and 3 reference points can provide 6 degrees of freedom—3 rotationally and 3 translationally. The tomography apparatus can be used to measure the locations of the marks as described herein and the response to a measured location the treatment can be adjusted.

FIG. 13E shows the eye coordinate reference system 150 and the moved eye coordinate reference system 150M. In many embodiments, the eye can be modeled as a substantially rigid body in which the movement of the plurality of marks can be used to determine movement of the eye. The coordinate reference system 150 comprises a first dimension 152, a second dimension 154, and third dimension 156 as described herein. The moved reference system 150M comprises a first dimension 152M, a second dimension 154M, and a third reference dimension 156M. Dimension 152 corresponds to dimension 152M which is moved. Dimension 154 corresponds to dimension 154M which is moved. Dimension 156 corresponds to Dimension 156M of the moved reference frame. In addition to movement of the eye translationally about the 3 dimensions, the marks can be measured and used to determine rotations about one or more of the dimensions. Rotation about the first dimension 152 may comprise rotation 152R, rotation about the second dimension 154 may comprise rotation 154R, and rotation about the third dimension 156 may comprise rotation 156R. The movements can be provided as vectors both rotationally and translationally about one or more degrees of freedom, for example, 6 degrees of freedom and the coordinate references can be transformed to determine new locations for laser treatment.

The plurality of reference locations is shown in relation to the plurality of marks. For example, first mark 772 is shown in relation to the first reference location 762. The second mark 774 is shown in relation to the second reference location 764. The third mark 776 is shown in relation to the third reference location 766. The fourth mark 778 is shown in relation to the fourth reference location 768. The relationship of the reference locations to the marks can be used to determine movement of the eye and the movement of the eye can be used to determine movement of target locations of the eye for example rotationally at a distance from the one or more marks. This determination of rotational and translational movement of the eye relative to the marks will allow rotational and translational corrections of the targeted locations of the eye away from the marks, for example.

Figure 14:
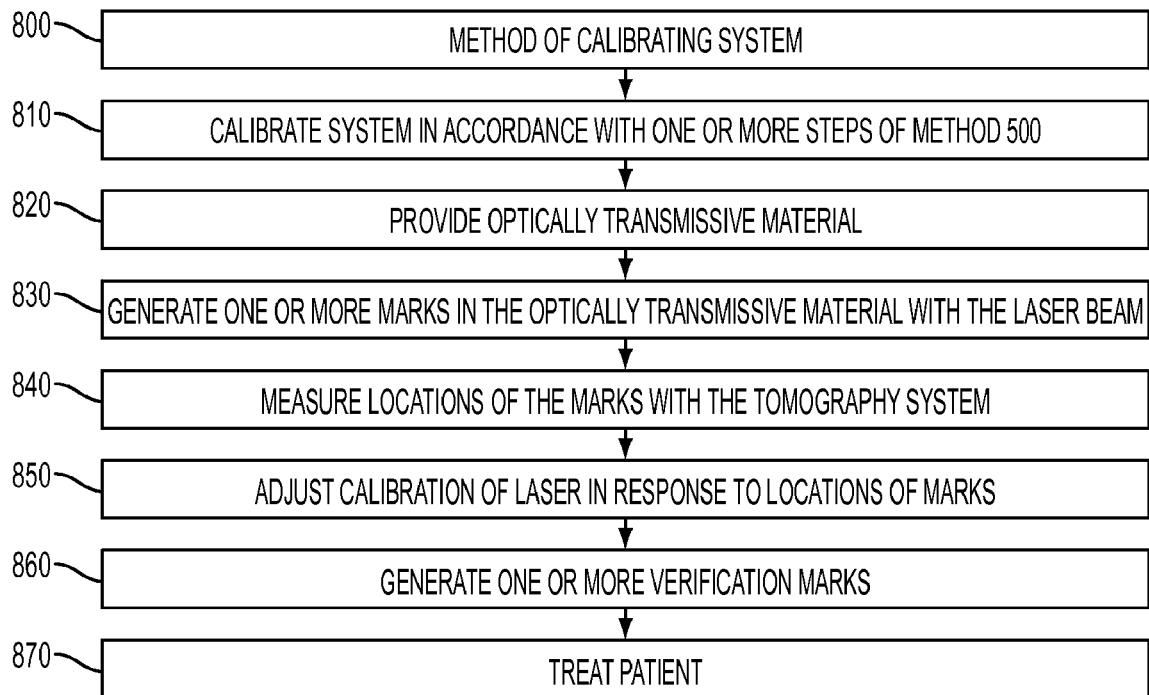
FIG. 14 shows a method of calibration a laser eye surgery system, in accordance with many embodiments.

FIG. 14 shows a method of calibrating the system in accordance with embodiment. As a step 810, the system is calibrated in accordance with one or more steps of method 500 as described herein and a step 820, an optically transmissive material is provided. The optically transmissive material may comprise an optically transmissive material of the eye or the optically transmissive material may comprise an optically transmissive material of the calibration structure as described herein. At a step 830, one or more marks are generated and the optically transmissive material with the laser beam and one or more marks may comprise a plurality of marks as described herein. At a step 840, locations of the marks are measured with the demography system as described herein. At a step 850, the calibration of the laser is adjusted in response to locations of the mark for example with in situ calibration of an eye, the laser beam can be adjusted so that the target locations more closely match the intended location based on the targeted locations. At a step 860, one or more verification marks are generated as described herein. At a step 870, a patient is treated as described herein.

Figure 15:
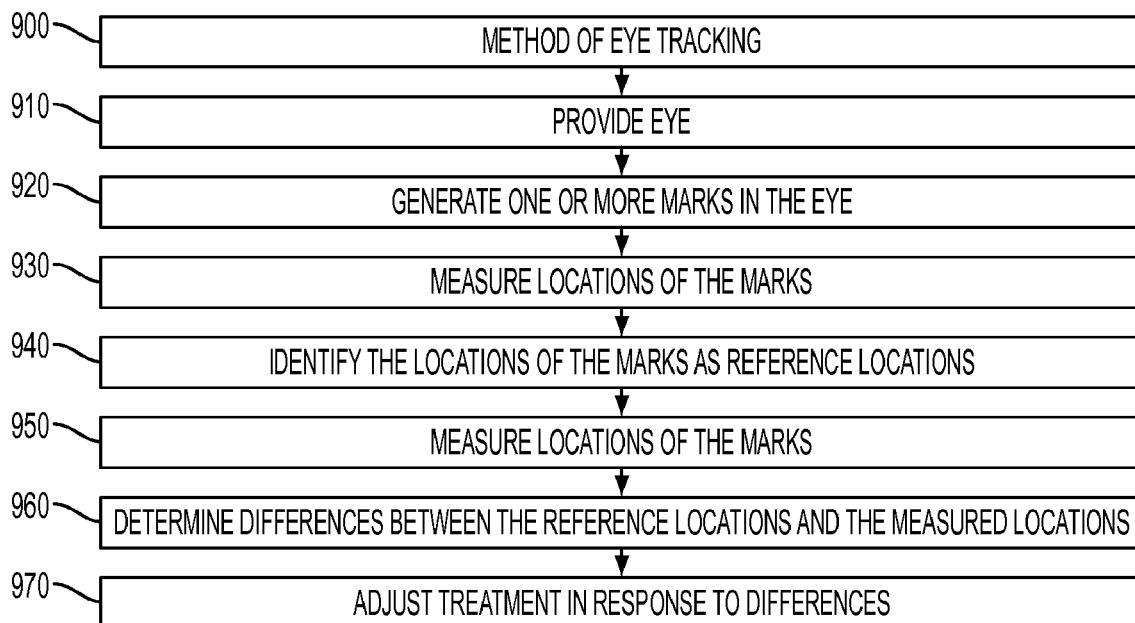
FIG. 15 shows a method of tracking the eye, in accordance with many embodiments.

FIG. 15 shows a method of eye tracking in accordance with embodiment. In a step 910, an eye is provided. In a step 920, one or more marks are created on the eye as described herein. At a step 930, locations of the marks are measured as described herein. At a step 940, the locations of the marks are identified as reference locations. At a step 950, the locations of the marks are measured as described herein. At a step 960, differences between the reference locations and the measured locations are determined. At a step 970, the treatment is adjusted in response to the differences between the reference locations and the locations of the marks as measured.

Figure 16:
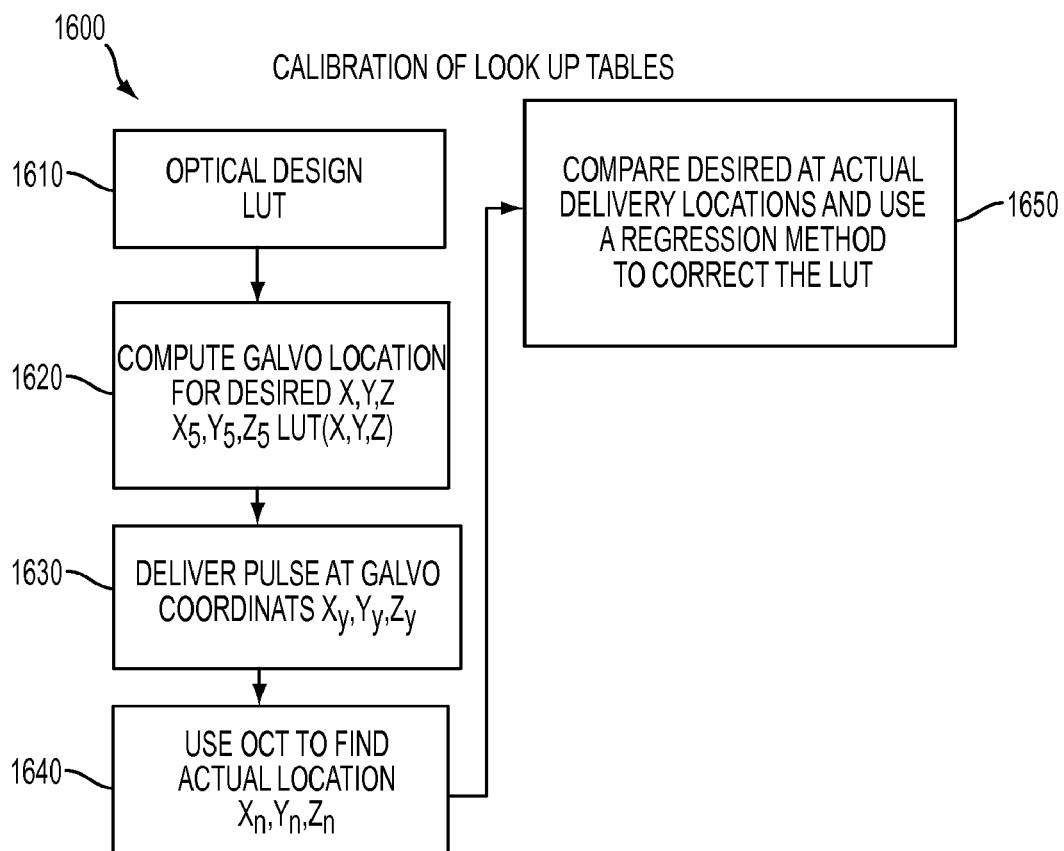
FIG. 16 shows an empirical example of a method of calibration of a laser eye surgery system, in accordance with many embodiments.

Examples of use of calibration methods described herein are presented as follows. As shown in FIG. 16, an empirical approach for calibration 1600, in accordance with many embodiments, may comprise the use of the optics, including shared optics 50, of the system 2 to generate an initial set of look up tables in a step 1610, linking real space points and their corresponding galvo parameters. In a step 1620, a galvo location may be computed for a desired point. An example of a line in that look up table may prescribe instructions to deliver a laser pulse at x=2 mm, y=3 mm and z=6 mm. In correspondence with these instructions, the x galvo may be rotated 1.8 deg, the y galvo may be rotated 3.1 deg, and the z galvo may be located at 13.6 mm, for instance. FIG. 7C3 shows further examples.

The calibration of initial look up tables may be performed by delivering a laser pulse to a desired location (in a computed/desired XYZ coordinate system, for example) in a step 1630. Then, the interferometer can be used to locate where the point go in reality (i.e., the actual location in a real XYZ coordinate system) in a step 1640. Repeating this operation with a plurality of points, the initial look up table may be warped to better match real and desired coordinates in a step 1650.

In very simple terms, the example calibration approach corrects for depth in the look up table. For instance, if all the points are deep by 10 μm, the initial look up tables may be adjusted so that the commanded z galvo location will be correspondingly shallower.

In another example a 3d warp is applied to the look up tables defined by a 3-dimensional polynomial that may move, stretch, and rotate the look up table. This may be a first degree polynomial warp but polynomials of other degrees may be appropriate in at least some instances. In exemplary embodiments, up to 16th degree polynomial warps may be used. Even greater degree polynomials may be used in further embodiments.

The above example calibration methods and steps may typically be done in a media with a similar index of refraction as that of an eye, such as gelatin. Then, an additional correction for the human lens index may be used.

Examples of use of motion tracking methods described herein are presented as follows. Interferometer (OCT) images comprising information of eye surfaces (e.g., cornea anterior and posterior, lens anterior and posterior, iris, limbus, etc.) may be analyzed and a mathematical model of the eye may be constructed. This model may comprise one or more of ellipsoidal fits (e.g., with 9 parameters) for the cornea anterior and posterior, spherical fits (e.g., with 4 parameters) for the lens anterior and posterior, or 3-dimensionally oriented elliptical fits for the iris and the limbus. In addition, the surface of the iris may be fitted by a toroidal fit.

A plurality of locations (e.g., initial locations) in the eye may be selected for marking with micro incisions performed with the laser. Subsequent interferometer (OCT) readings of the marked areas may be analyzed and the new location of the marks may be determined (new locations). If some "eye motion" has occurred during the acquisition of the "initial locations" and the "new locations", the two location may not be the same.

The "eye motion" may be computed by assuming a mechanical model of the eye (e.g., viscoelastic material, elastic material, or rigid) and deriving the "eye motion" based on the "initial location" and "new location". For example, a rigid eye model may be used. This model may indicate that deformations of the eyeball may be neglected, so that any two points in the eye may always have the same distance under this idealization. This idealization may be applicable to cases that the deformations are expected to be small, such as ours.

Under the rigid body eye assumption, the mathematical eye model composed by the ellipsoids, spheres, 3-dimensional ellipses, and/or torus can be translated and rotated according to the rigid body motion that may be described as:

$$X\text{new}_i = DX_i + \Sigma_j Rot_{ij} X_j$$

An "initial location" (X=x, y, z) may be rotated by the 3×3 rotation matrix "Rot". The resultant location may have added a translation vector (DX=dx, dy, dz) to provide the "new location".

In the above expression, a set of "initial locations" may be known and as may be the corresponding set of "new locations." The three parameters (i.e., Euler angles) that form the rotation matrix (Rot) and the three parameters that are in the translation vector (DX) may need to be found. The solution can be performed by a regression method and the rigid body motion (translation-rotation transformation) may be defined.

This rigid body transformation may keep track of the current motion of the eye by means of performing the above process sequentially. A treatment comprising a plurality of points that define a trajectory may then be adjusted with the above formula to accurately target the new location.

In view of the above, a laser system to treat an object with a laser beam in one embodiment comprises a laser to generate the laser beam, a tomography system to generate a measurement beam and measure an optically transmissive material of the object; an optical delivery system coupled to the laser and the tomography system to deliver the laser beam and the measurement beam to the object; and a processor coupled to the laser, the tomography system, and the optical delivery system, the processor comprising a tangible medium embodying instructions to: (1) place a mark on the object with the laser beam in response to a target location and, (2) measure a location of the mark with the measurement beam. The object may comprise one or more of an eye, an optically transmissive material, a gel, a liquid, a viscous material, a solid optically transmissive material, or a fluid of a patient interface above the eye. The fluid of the patient interface may comprise one or more of saline or viscoelastic fluid and wherein the fluid is marked with the laser beam.

The processor may comprise instructions to mark the eye at a plurality of locations corresponding to a plurality of target locations, the plurality of locations comprising locations of one or more of a cornea, an aqueous humor, an iris, an anterior lens capsule, an anterior lens capsule, a posterior lens capsule, a cortex, or a nucleus.

The processor may comprise instructions to mark the eye at the plurality of locations prior to incising the eye with a plurality of laser beam pulses to one or more of incise or treat the eye with the laser beam pulses.

The plurality of marks may define a volume and the laser beam may be pulsed to incise the tissue are delivered at a plurality of locations within the volume. The volume may comprises at least a portion of a tissue structure of the eye comprising one or more of a tear film, a cornea, an aqueous humor, an iris, an anterior lens capsule, the posterior lens capsule, a lens cortex, a lens nucleus, a vitreous humor, a Berger's space, or an anterior hyaloid membrane of the vitreous humor.

The processor may comprise instructions to identify a corresponding target location for each of the plurality of marks measured with the tomography system and compare the corresponding target location with the measured location for each of the plurality of marks in order to determine one or more of calibration or eye position.

The tissue structure of the eye may comprise a plurality of tissue structures, each of the plurality of tissue structures having a different index of refraction for the laser beam than another of the plurality of tissue structures, and wherein each tissue structure comprises a first index of refraction for the laser beam and a second index of refraction for a measurement beam of the tomography system, the first index of refraction different from the second index of refraction, and wherein the laser beam and measurement beam comprise one or more wavelengths of light different from each other.

The processor may comprise instructions to compare the location of the mark with the target location and calibrate the laser in response to the location of the mark and the targeted location of the mark.

The processor may comprise instructions to perform in situ calibration to correct for drift of an optical delivery system to deliver the laser beam to the object.

The processor may comprise instructions to perform a daily calibration to correct for drift of an optical delivery system to deliver the laser beam to the object.

The processor may comprise instructions to adjust one or more machine parameters related to one or more of the laser, the optical delivery system, or the tomography system in response to a comparison of the corresponding target location with measured location for said each of the plurality of marks in order to calibrate the laser system.

The processor may comprise instructions to track the object in response to the measured location of the mark.

The processor may comprise instructions to adjust positions of the laser beam pulses in response to a comparison of the corresponding target location with measured location for said each of the plurality of marks in order to track and correct for eye movement with the laser system.

The location of each of the plurality of marks may be compared with a prior location of said each of the plurality of marks in order to determine movement of the eye.

The plurality of marks may comprise three or more marks and wherein the movement of the eye comprises rotation of the eye around one or more dimensions of a coordinate reference system of the eye, and wherein the treatment is adjusted in response to translation along the one or more dimensions, and wherein the movement of the eye comprises translation of the eye along one or more dimensions of the coordinate reference system of the eye and wherein the treatment is adjusted in response to translation along the one or more dimensions.

The one or more dimensions may comprise three dimensions, wherein the treatment is adjusted in response to rotation around the three dimensions and translation along the three dimensions and the optically transmissive material may comprise a plurality of optically transmissive structures having a plurality of indices of refraction, and the positions of laser beam pulses to treat one or more of the optically transmissive structures may be adjusted in response to locations of the optically transmissive structures having the plurality of indices of refraction.

The processor may comprise instructions to mark the material in each of the optically transmissive structures to define a volume comprising the plurality of optically transmissive structures having the plurality of indices of refraction.

The processor may comprise instructions to mark the material in a first of the optically transmissive structures and to adjust positions of the laser beam pulses for treatment in a second of the optically transmissive structures without placing marks for tracking in the second of the optically transmissive structures, the second of the plurality of optically transmissive structures comprising an index of refraction different than the index of refraction of the first of the optically transmissive structures.

The processor may comprise instructions to mark the material with one or more bubbles, and the processor may comprise instructions to correct for optical aberrations in response to locations of the one or more bubbles.

The tomography system may comprise one or more of an optical coherence tomography system, a spectral domain optical coherence tomography system, a time domain optical coherence tomography system, a Scheimpflug tomography system, a confocal tomography system, or a low coherence reflectometry system.

The laser system may further comprise an acoustic transducer to detect optical breakdown in response to an amount of energy of the laser beam.

A method of treating an object with a laser beam comprises placing a mark on the object in response to a target location; and measuring a location of the mark with a measurement beam. The method may further comprise incising the eye with a plurality of laser beam pulses to one or more of incise or treat the eye with the laser beam pulses subsequent to placing the mark on the object. The method may further comprise identifying a corresponding target location for each of the plurality of marks measured with the tomography system and comparing the corresponding target location with the measured location for each of the plurality of marks in order to determine one or more of calibration or eye position. The method may further comprise comparing the location of the mark with the target location and calibrating the laser in response to the location of the mark and the targeted location of the mark.

The laser beam is generated by a laser. The laser beam and the measurement beam are delivered by an optical delivery system. The object may comprise one or more of an eye, an optically, a calibration apparatus comprising transmissive material, a gel, a liquid, a viscous material, a solid optically transmissive material, or a fluid of a patient interface above the eye. The fluid of the patient interface may comprise one or more of saline or viscoelastic fluid and wherein the fluid is marked with the laser beam.

The measurement beam may be generated by a tomography system. The tomography system may comprise one or more of an optical coherence tomography system, a spectral domain optical coherence tomography system, a time domain optical coherence tomography system, a Scheimpflug tomography system, a confocal tomography system, or a low coherence reflectometry system.

Placing the mark on the object in response to a target location may comprise marking the eye at a plurality of locations corresponding to a plurality of target locations, the plurality of locations comprising locations of one or more of a cornea, an aqueous humor, an iris, an anterior lens capsule, an anterior lens capsule, a posterior lens capsule, a cortex or a nucleus.

Marking the eye at the plurality of locations may comprise defining a volume, and wherein laser beam pulses to incise the tissue are delivered at a plurality of locations within the volume. The volume may comprise at least a portion of a tissue structure of the eye comprising one or more of a tear film, a cornea, an aqueous humor, an iris, an anterior lens capsule, the posterior lens capsule, a lens cortex, a lens nucleus, a vitreous humor, a Berger's space, or an anterior hyaloid membrane of the vitreous humor.

The tissue structure of the eye may comprise a plurality of tissue structures, each of the plurality of tissue structures having a different index of refraction for the laser beam than another of the plurality of tissue structures and wherein each tissue structure comprises a first index of refraction for the laser beam and a second index of refraction for a measurement beam of the tomography system, the first index of refraction different from the second index of refraction, and wherein the laser beam and measurement beam comprise one or more wavelengths of light different from each other.

The method may further comprise performing in situ calibration to correct for drift of an optical delivery system to deliver the laser beam to the object.

The method may further comprise performing a daily calibration to correct for drift of an optical delivery system to deliver the laser beam to the object.

The method may further comprise adjusting one or more machine parameters related to one or more of the laser, the optical delivery system, or the tomography system in response to a comparison of the corresponding target location with measured location for said each of the plurality of marks in order to calibrate the laser system.

The method may further comprise tracking the object in response to the measured location of the mark.

The method may further comprise adjusting positions of the laser beam pulses in response to a comparison of the corresponding target location with measured location for said each of the plurality of marks in order to track and correct for eye movement with the laser system.

The location of each of the plurality of marks may be compared with a prior location of said each of the plurality of marks in order to determine movement of the eye. The plurality of marks may comprise three or more marks. The movement of the eye may comprise rotation of the eye around one or more dimensions of a coordinate reference system of the eye, and wherein the treatment is adjusted in response to translation along the one or more dimensions, and the movement of the eye may comprise translation of the eye along one or more dimensions of the coordinate reference system of the eye and wherein the treatment is adjusted in response to translation along the one or more dimensions. The one or more dimensions may comprise three dimensions, and the treatment may be adjusted in response to rotation around the three dimensions and translation along the three dimensions. The optically transmissive material may comprise a plurality of optically transmissive structures having a plurality of indices of refraction and wherein positions of laser beam pulses to treat one or more of the optically transmissive structures are adjusted in response to locations of the optically transmissive structures having the plurality of indices of refraction.

The method may further comprise marking the material in each of the optically transmissive structures to define a volume comprising the plurality of optically transmissive structures having the plurality of indices of refraction.

The method may further comprise marking the material in a first of the optically transmissive structures and adjusting positions of the laser beam pulses for treatment in a second of the optically transmissive structures without placing marks for tracking in the second of the optically transmissive structures, the second of the plurality of optically transmissive structures comprising an index of refraction different than the index of refraction of the first of the optically transmissive structures.

The method may further comprise marking the material with one or more bubbles and correcting for optical aberrations in response to locations of the one or more bubbles.

The method may further comprise detecting optical breakdown in response to an amount of energy of the laser beam with an acoustic transducer.

A system to treat an eye with a laser beam, the system comprises a laser to generate the laser beam, a measurement system configured to measure first and second optically transmissive materials having differing indices of refraction;

an optical delivery system coupled to the laser to deliver the laser beam to the material second material through the first material; and a processor coupled to the measurement system and the optical delivery system, the processor configured to form a mark in the material with the laser beam per a target location, to measure a location of the mark with the measurement system, to calibrate the system by comparing the target location and the measured location of the mark using the indices of refraction, and to direct the beam toward a treatment target within the eye with the calibrated system.

While preferred embodiments of the present disclosure have been shown and described herein, it will be obvious to those skilled in the art that such embodiments are provided by way of example only. Numerous variations, changes, and substitutions will be apparent to those skilled in the art without departing from the scope of the present disclosure. It should be understood that various alternatives to the embodiments of the present disclosure described herein may be employed without departing from the scope of the present invention. Therefore, the scope of the present invention shall be defined solely by the scope of the appended claims and the equivalents thereof.

What is claimed is:

1. A system to treat an eye with a laser beam, the system comprising:

a laser configured to generate the laser beam;

a measurement system configured to measure first and second optically transmissive materials of the eye having differing indices of refraction;

an optical delivery system coupled to the laser to deliver the laser beam to the second material through the first material; and a processor coupled to the measurement system and the optical delivery system, the processor configured to form a plurality of marks in both the first material and the second material with the laser beam per a plurality of target locations, wherein the marks in the first material and the second material together define a three dimensional calibration volume in the eye that includes both the first material and the second material, to measure a plurality of locations of the marks with the measurement system, to calibrate the system for the calibration volume by comparing the target locations and the measured locations of the marks using the indices of refraction, and to direct the beam toward a treatment target located within the calibration volume within the eye with the calibrated system.

2. The system of claim 1, wherein the processor is configured to calibrate the system by adjusting one or more machine parameters related to one or more of the laser, the optical delivery system, or the measurement system in response to comparison of the target locations with measured locations of the marks.

3. The system of claim 1, wherein the processor is configured to adjust positions of the laser beam in response to a comparison of the corresponding target location with measured location for each of the plurality of marks in order to track and correct for eye movement with the laser system.

4. The system of claim 3, wherein the location of each of the plurality of marks is compared with a prior location of each of the plurality of marks in order to determine movement of the eye.

5. The system of claim 4, wherein the plurality of marks comprises three or more marks and wherein the movement of the eye comprises rotation of the eye around one or more dimensions of a coordinate reference system of the eye, and wherein the treatment is adjusted in response to translation along the one or more dimensions, and wherein the movement of the eye comprises translation of the eye along one or more dimensions of the coordinate reference system of the eye and wherein the treatment is adjusted in response to translation along the one or more dimensions.

6. The system of claim 5, wherein the one or more dimensions comprises three dimensions, and wherein the treatment is adjusted in response to rotation around the three dimensions and translation along the three dimensions.

7. The system of claim 1, wherein the marks are bubbles formed in the first material and the second material.

8. The system of claim 1, wherein the measurement system comprises one or more of an optical coherence tomography system, a spectral domain optical coherence tomography system, a time domain optical coherence tomography system, a Scheimpflug tomography system, a confocal tomography system, or a low coherence reflectometry system.

9. The system of claim 1, further comprising an acoustic transducer to detect optical breakdown in response to an amount of energy of the laser beam.

* * * * *